US010252291B2

United States Patent
Madsen et al.

(10) Patent No.: US 10,252,291 B2
(45) Date of Patent: *Apr. 9, 2019

(54) PHOTO-CURING OF THERMOPLASTIC COATINGS

(71) Applicant: Coloplast A/S, Humlebaek (DK)

(72) Inventors: Niels Jorgen Madsen, Allerod (DK); Egon Triel, Golden Valley, MN (US); Bo Rud Nielsen, Allerod (DK); Carsten Hoj, Vanlose (DK)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/723,679

(22) Filed: Dec. 21, 2012

(65) Prior Publication Data

US 2013/0115466 A1 May 9, 2013

Related U.S. Application Data

(62) Division of application No. 12/309,641, filed as application No. PCT/EP2007/005766 on Jul. 25, 2007, now abandoned.

(Continued)

(30) Foreign Application Priority Data

Jul. 25, 2006 (DK) .................................. 2006 01013
Dec. 15, 2006 (WO) ................ PCT/DK2006/000715

(51) Int. Cl.
- *B05D 5/08* (2006.01)
- *B05D 3/06* (2006.01)

(Continued)

(52) U.S. Cl.
CPC .............. *B05D 3/067* (2013.01); *A61L 27/34* (2013.01); *A61L 29/085* (2013.01); *A61L 31/10* (2013.01);

(Continued)

(58) Field of Classification Search
CPC .. B05D 5/08; B05D 3/067; B05D 3/00; B29C 45/0053; B29C 45/14; B32B 27/38;

(Continued)

(56) References Cited

U.S. PATENT DOCUMENTS 5,061,424 A 10/1991 Karimi et al.
5,084,315 A 1/1992 Karimi et al.
(Continued)

FOREIGN PATENT DOCUMENTS

EP 0 769 306 4/1997
EP 0 860 213 8/1998
(Continued)

OTHER PUBLICATIONS

Charraher et al. Polymer Chemistry, Sixth Edition, pp. 299-230: Mechanism for Free Radical Chain Polymerization, 2005. http://books.google.com/books?id=Jg_I8B7.
(Continued)

*Primary Examiner* — Dah-Wei D. Yuan
*Assistant Examiner* — Hai Yan Zhang
(74) *Attorney, Agent, or Firm* — Coloplast Corp., Coloplast A/S; Nick Baumann

(57) ABSTRACT

The present invention relates to a method for the preparation of a medical device element by means of extrusion or injection molding and to medical devices comprising such extruded or injection molded medical device elements. The medical device elements (e.g. tubes, wires, lines, stents, catheters, guides, endodontic instruments, needles, trocars for e.g. laparoscopic surgery, laparoscopic accessories, surgical instruments, guide wires) are characterized by a prefabricated shaped article or a thermoplastic substrate polymer having thereon a layer of a covalently cross-linked coating composition of a thermoplastic matrix polymer and a hydrophilic polymer. The method involves a coating composition comprising a thermoplastic matrix polymer, a hydrophilic polymer, and one or more photo-initiator(s), e.g. covalently linked to molecules of the thermoplastic matrix polymer and/or to molecules of the hydrophilic polymer. The coating composition is irradiated with UV or visible light so as to covalently cross-link said coating composition.

8 Claims, 5 Drawing Sheets

Related U.S. Application Data

(60) Provisional application No. 60/832,945, filed on Jul. 25, 2006.

(51) Int. Cl.

| A61L 27/34 | (2006.01) |
|---|---|
| A61L 29/08 | (2006.01) |
| A61L 31/10 | (2006.01) |
| B29C 45/00 | (2006.01) |
| B29C 45/14 | (2006.01) |
| B29C 45/16 | (2006.01) |
| B29C 47/00 | (2006.01) |
| B29C 47/02 | (2006.01) |
| C08G 18/48 | (2006.01) |
| C08G 18/83 | (2006.01) |
| C08G 65/331 | (2006.01) |
| C08G 65/332 | (2006.01) |
| A61L 31/14 | (2006.01) |
| B29C 71/04 | (2006.01) |
| B29C 35/08 | (2006.01) |
| B29K 23/00 | (2006.01) |
| B29K 75/00 | (2006.01) |
| B29K 77/00 | (2006.01) |
| B29L 31/00 | (2006.01) |

(52) U.S. Cl.
CPC .............. *A61L 31/14* (2013.01); *B05D 5/08* (2013.01); *B29C 45/0053* (2013.01); *B29C 45/14* (2013.01); *B29C 45/1679* (2013.01); *B29C 47/0023* (2013.01); *B29C 47/021* (2013.01); *C08G 18/4833* (2013.01); *C08G 18/83* (2013.01); *C08G 65/331* (2013.01); *C08G 65/3324* (2013.01); *B05D 2201/00* (2013.01); *B29C 71/04* (2013.01); *B29C 2035/0827* (2013.01); *B29C 2045/0075* (2013.01); *B29K 2023/06* (2013.01); *B29K 2023/083* (2013.01); *B29K 2023/086* (2013.01); *B29K 2075/00* (2013.01); *B29K 2077/00* (2013.01); *B29K 2995/0092* (2013.01); *B29L 2031/753* (2013.01); *B29L 2031/7542* (2013.01); *C08G 2210/00* (2013.01); *Y10T 428/31511* (2015.04); *Y10T 428/31551* (2015.04); *Y10T 428/31786* (2015.04)

(58) Field of Classification Search
CPC ......... B32B 27/40; B32B 27/18; A61L 27/34; A61L 29/085; A61L 31/10; A61L 31/14
USPC ........... 427/2.1; 428/413; 523/423; 525/123; 600/585; 604/525; 623/1.21, 66.1, 1.19
See application file for complete search history.

(56) References Cited

U.S. PATENT DOCUMENTS

| 5,263,992 | A | * | 11/1993 | Guire | ............ A61F 2/0077 436/501 |
| 5,722,424 | A | * | 3/1998 | Engelson | ............ A61L 31/10 600/585 |
| 6,139,510 | A | | 10/2000 | Palermo | |
| 6,248,811 | B1 | | 6/2001 | Otterbach et al. | |
| 6,447,835 | B1 | | 9/2002 | Wang et al. | |
| 6,632,446 | B1 | * | 10/2003 | Hubbell | ............ C08B 37/0084 424/423 |
| 7,318,944 | B2 | * | 1/2008 | Neary | ............ A61F 2/07 427/2.24 |
| 2002/0127266 | A1 | | 9/2002 | Sawhney et al. | |
| 2004/0062793 | A1 | * | 4/2004 | Dyke | ............ 424/445 |
| 2004/0098110 | A1 | | 5/2004 | Williams et al. | |
| 2005/0043752 | A1 | * | 2/2005 | Phan et al. | ............ 606/155 |
| 2005/0049574 | A1 | | 3/2005 | Petrick et al. | |
| 2005/0054774 | A1 | * | 3/2005 | Kangas | ............ 525/123 |
| 2005/0070688 | A1 | * | 3/2005 | Lewandowski et al. | ...... 528/425 |
| 2006/0240072 | A1 | * | 10/2006 | Chudzik | ................ A61L 27/34 424/426 |
| 2006/0287710 | A1 | | 12/2006 | Lendlein et al. | |
| 2008/0306455 | A1 | * | 12/2008 | Dias | ................ A61L 27/34 604/265 |

FOREIGN PATENT DOCUMENTS

| WO | WO 89/09246 | 10/1989 | | |
| WO | WO-8909246 A1 | * | 10/1989 | ............ A61L 29/085 |
| WO | WO 03/042724 | 5/2003 | | |
| WO | WO 2004/110515 | 12/2004 | | |
| WO | WO 2005/035607 | 4/2005 | | |
| WO | WO-2005035607 A1 | * | 4/2005 | ............ A61L 15/22 |
| WO | WO 2006056482 A1 | * | 6/2006 | |

OTHER PUBLICATIONS

Pebax 7233 SA 01 data sheet, http://www.pebax.com/pdg/pebax/en/tds_pebax_7233sa01_2010.pdf. Retrieved on Apr. 30, 2012.

Hydrophilic Monomers for Research Applications, http://www.polysciences.com/SiteData/docs/wb_2011_hy/565679bf937caed7/wb_2011_hydrophilic.pdf. Retrieved on Apr. 30, 2012.

Gould, et al. "Novel Self-Initiating UV-Curable Resins: Generation Three," Proceedings from RadTech Europe 05, Barcelona, Spain, Oct. 18-20, 2005, vol. 1, pp. 245-251.

Nguyen et al. "Maleimide Reactive Oligomers," Proceedings from RadTech Europe 03, Berlin, Germany, Nov. 3-5, 2003, vol. 1, pp. 589-594.

Fouassier. "Excited-State Reactivity in Radical Polymerisation Photo-Initiators," Radiation in Curing Polymer Science and Technology, vol. II, Ch. 1, Elsevier, London, 1993, pp. 1-61.

Kopeinig et al. "Further Covalently Bonded Photoinitiators," Proceedings from RadTech Europe 05, Barcelona, Spain, Oct. 18-20, 2005, vol. 2, pp. 375-381.

March, "Advanced Organic Chemistry. Reaction, Mechanisms, and Structure," $3^{rd}$ edition, Wiley-Interscience, New York, 1985, pp. 377-379.

Stevens, "Polymer Chemistry, An Introduction," $3^{rd}$ edition, Oxford University Press, New York, 1999, pp. 327-328.

March. "Advanced Organic Chemistry., Reaction, Mechanisms, and Structure," $3^{rd}$ edition, Wiley-Interscience, New York, 1985, p. 332.

March. "Advanced Organic Chemistry., Reaction, Mechanisms, and Structure," $3^{rd}$ edition, Wiley-Interscience, New York, 1985, pp. 484-487.

March. "Advanced Organic Chemistry., Reaction, Mechanisms, and Structure," $3^{rd}$ edition, Wiley-Interscience, New York, 1985, pp. 636-637.

Walling et al. "Free Radical Additions to Olefins to Form Carbon-Carbon Bonds," Organic Reactions, vol. 13, pp. 91-149.

Clinton et al. "Encyclopedia of Polymer Science and Engineering," $2^{nd}$ edition, H.F. Mark, N.M. Bikales, C.G. Overberger, vol. 6, 1986, p. 252.

Leon et al. "UV-Light Sensitive (LS®) Urethane Acrylate Oligomers," Proceedings from RadTech Europe 05, Barcelona, Spain, Oct. 18-20, 2005, vol. 2, pp. 359-364.

Kochi et al. "Catalytic Reactions of Peroxides, Direct Initiation by Curprous Species." Tetrahedron, vol. 24, 1968, pp. 5099-5113.

Rawlinson et al. "One-Step Substitute Acyloxylation at Carbon," Part I. Reactions Involving Peroxides, Synthesis, International Journal of Methods in Synthetic Organic Chemistry, vol. 1, 1972, pp. 1-28.

Newman et al. "Reactions Proceeding by the [3.2.1] Bicyclic Path," J. Am. Chem. Soc., vol. 88(4), 1966, pp. 781-784.

Thijs et al. "Photochemistry of Perester Initiators." J. Org. Chem., vol. 44(23), 1979, pp. 4123-4129.

Sosnovsky et al. "The Peroxyester Reaction." Angew. Chem., Int. Edition, vol. 3(4), 1964, pp. 269-276.

(56) References Cited

OTHER PUBLICATIONS

Lawesson et al. "Studies on Peroxy Compounds. XVII. The Preparation of Aldehydes and Ketones from Ethers," Arkiv for Kemi, vol. 17(45), 1961, pp. 465-473.
Gilbert et al. "Essentials of Molecular Photochemistry," Blackwell, London, 1991.
http://www.sanesters.com/download/BAC-PRESENTATION.PPT.

* cited by examiner

Figure 1
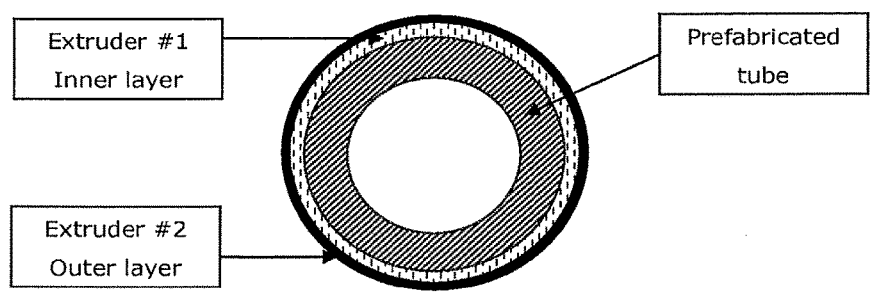
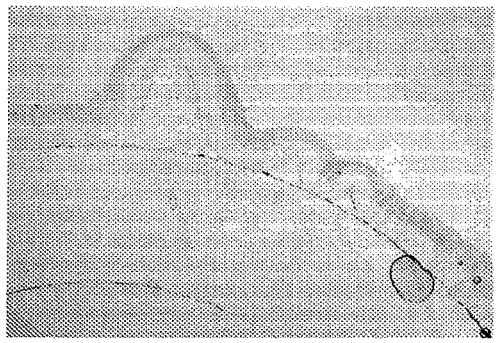
Figure 2
Figure 3

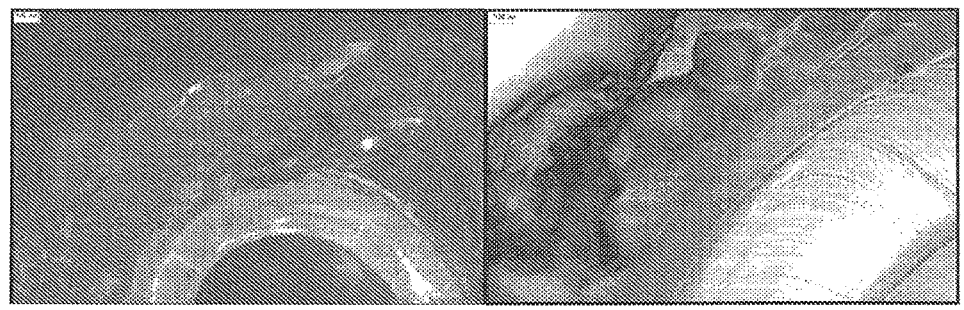
Figure 4  (a)  (b)
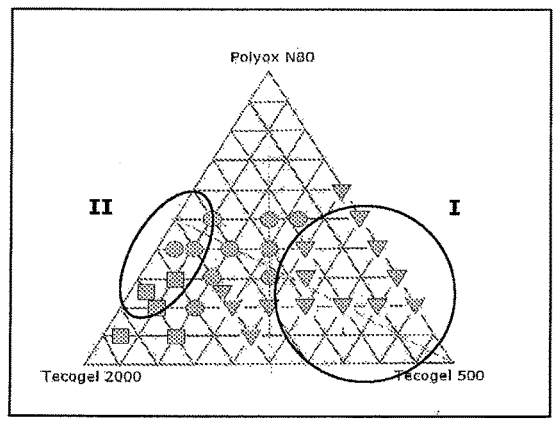
Figure 5

US 10,252,291 B2

PHOTO-CURING OF THERMOPLASTIC COATINGS

This is a divisional of application Ser. No. 12/309,641, filed Oct. 1, 2009, which is a 371 of PCT Application PCT/EP2007/057666, filed Jul. 25, 2007 which claims benefit from Application No. 60/832,945 filed Jul. 25, 2006 and Danish Application 2006 01013, filed Jul. 25, 2007 and Denmark PCT/DK2006/000715, filed Jul. 25, 2006, the disclosure of each of which is hereby incorporated by reference.

FIELD OF THE INVENTION

The present invention relates to a method for the preparation of a medical device element by means of extrusion, injection moulding or powder coating. The invention further relates to medical devices comprising such extruded, injection moulded or powder coated medical device elements. The medical device elements are characterized by a prefabricated shaped article or a thermoplastic substrate polymer having thereon a layer of a covalently cross-linked coating composition of a thermoplastic matrix polymer and a hydrophilic polymer.

BACKGROUND OF THE INVENTION

Many medical devices require a lubricated surface. In the medical field, simple devices such as, for example, catheters, guide wires, etc., must be inserted into a body cavity or through the skin and at a later time be withdrawn. Patient treatment often includes catheterization procedures or nutrition delivery systems, most of which involve invasive techniques. In all such cases, effective lubrication which is stable throughout both the insertion and withdrawal stages of the procedure contributes greatly to patient comfort.

U.S. Pat. No. 5,084,315 discloses a method for preparing a shaped article, e.g. by co-extrusion, utilizing a composition including PEO and a polyurethane, which is not covalently cross-linked. The surface of the article is said to be lubricious when contacted with water.

U.S. Pat. No. 5,061,424 discloses a method for preparing a shaped article, e.g. by co-extrusion, utilizing a composition including PVP and a polyurethane, which is not covalently cross-linked. The surface of the article is said to be lubricious when contacted with water.

U.S. Pat. No. 6,447,835 discloses a method of preparing a coated hollow polymeric tubular member for a medical device by co-extruding the tube together with a coating. The coating may comprise acrylic monomers which may be reacted to form a cross-linked acrylic polymer network after extrusion.

SUMMARY OF THE INVENTION

Although the shaped articles of U.S. Pat. No. 5,084,315 and U.S. Pat. No. 5,061,424 may have certain desirable and—for some applications—satisfactory properties with respect to reduced friction, the present inventors have found (see Reference Examples 1-3) that it was not possible to combine the exceptionally low friction required for certain medical devices, such as catheters and guide wires, with a sufficient cohesion of the coating and a sufficient adhesion of the coating to a substrate. Hence, the present inventors found it necessary to develop methods for the preparation of medical devices which provide advantages with respect to simplicity, exceptionally low friction, excellent cohesion and excellent adhesion.

Hence, the present invention provides a solution to the above-mentioned problems by providing a method for the preparation of medical devices, cf. the method defined in claim 1, which provides advantages with respect to simplicity, exceptionally low friction, excellent cohesion and excellent adhesion, and novel medical devices.

BRIEF DESCRIPTION OF THE DRAWINGS

FIG. 1 illustrates a medical device (e.g. a tube of catheter) of a prefabricated tube, a layer of a thermoplastic substrate polymer, and a covalently cross-linked coating composition (see Example 6).

FIG. 2 shows delamination from the tube after swelling due to insufficient photo-curing (see Example 6).

FIG. 3 shows swelled layers bonded to the tube due to proper photo-curing (see Example 6).

FIG. 4 shows non-cross-linked disintegration of a PVP coating composition (see Reference Example 2). a) 12.5× zoom; b) 40× zoom.

FIG. 5 shows the adhesion properties of different blends after hot-press lamination onto Estane 58212. ■-symbols represent blends that disintegrated when they were swelled in water: The water absorption was high but the gel strength was too low. The ●-symbols represent complete delamination, and separation of the layer from the substrate occurs. The ▼-symbols indicate good adhesion to the substrate with no or very few water blisters between the layers. See Reference Example 3 for details and an explanation of areas I and II.

DETAILED DESCRIPTION OF THE INVENTION

The Method of the Invention

Figure 6:
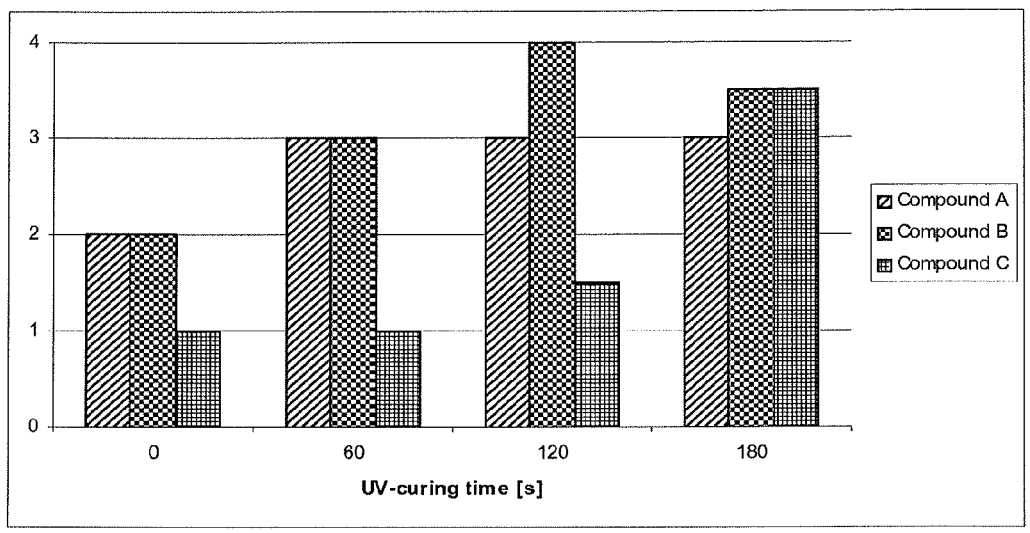
FIG. 6 shows the adhesion of extruded layers of compounds/compositions A, B and C, respectively, on a Estane 58212 polyurethane tube as a function of photo-curing time, as evaluated on a subjective scale from 1 to 4 (see Example 6 for details).

As mentioned above, the present invention relates to a method for the preparation of a medical device element, said method comprising the steps of:
(i) providing a prefabricated shaped article and/or a thermoplastic substrate polymer;
(ii) providing a coating composition comprising a thermoplastic matrix polymer, a hydrophilic polymer, and one or more photo-initiator(s);
(iii) extruding, injection moulding or powder coating the coating composition of step (ii) on the prefabricated shaped article and/or the thermoplastic substrate polymer of step (i) so as to provide the medical device element of said prefabricated shaped article and/or said substrate polymer having thereon a layer of said coating composition, wherein, when both of said prefabricated shaped article and said substrate polymer are present, said prefabricated shaped article has thereon a layer of said substrate polymer;

(iv) irradiating the coating composition with UV or visible light (wavelength in the range of 100-750 nm) so as to covalently cross-link said coating composition.

The invention is based on the finding that cross-linking of the coating composition subsequent to extrusion, injection moulding or powder coating by means of one or more photo-initiator(s) and UV or visible light provides medical device elements which have: good adhesion of the coating composition including the hydrophilic polymer to the prefabricated shaped article or the substrate polymer; good cohesion of the coating composition; and good water retention of the hydrophilic polymer in the wet state and thereby excellent properties with respect to low friction for an extended period of time.

The good properties with respect to good water retention of the hydrophilic polymer and excellent properties with respect to low friction for an extended period of time is somewhat contradictory to the fact the flexibility of the polymer chains will be restricted by means of the cross-linking of the polymer and anchoring to the substrate polymer or prefabricated shaped article.

In one important embodiment of the invention, the one or more photo-initiator(s) are covalently linked to a polymer or a scaffold, e.g. to molecules of the thermoplastic matrix polymer and/or to molecules of the hydrophilic polymer.

Medical Device

The term "medical device" should be interpreted in a fairly broad sense. Suitable examples of medical devices (including instruments) are catheters (such as urinary catheters), endoscopes, laryngoscopes, tubes for feeding, tubes for drainage, endotracheal tubes, guide wires, sutures, cannulas, needles, thermometers, condoms, urisheaths, barrier coatings e.g. for gloves, stents and other implants, contact lenses, extra corporeal blood conduits, membranes e.g. for dialysis, blood filters, devices for circulatory assistance, condoms, dressings for wound care, and ostomy bags. Most relevant are catheters, endoscopes, laryngoscopes, tubes for feeding, tubes for drainage, guide wires, sutures, and stents and other implants. Particularly interesting medical devices within the context of the present invention are catheters, such as urinary catheters.

It is also envisaged that the method of the invention is equally useful for the preparation of devices with low-friction surfaces for non-medical purposes, e.g. packaging for foodstuff, razor blades, fishermen's net, conduits for wiring, water pipes having a coating inside, sports articles, cosmetic additives, mould release agents, and fishing lines and nets.

Some medical devices may be constructed of one or more medical device elements which, when being assembled or rearranged, represent the ready-to-use medical device. Reference to a "medical device element" and "catheter element" means the medical device or catheter as such (i.e. one piece medical device or catheter) or a part of a "ready-to-use" medical device or catheter.

Medical device elements are in the present context formed from a prefabricated shaped article and/or a thermoplastic substrate polymer and a coating composition. Upon (co) extrusion or injection moulding of the prefabricated shaped article and/or the thermoplastic substrate polymer and the simultaneous or subsequent application of the coating composition by co-extrusion, injection moulding or powder coating, at least a part of the surface of the prefabricated shaped article or the substrate polymer becomes coated with the coating composition as will be explained in more detail in the following. In some embodiments, the coating composition (i.e. a hydrophilic coating) is covering the full (outer) surface of the prefabricated shaped article/substrate polymer, and in some other embodiments, only to a part of the surface thereof. In the most relevant embodiments, the coating composition covers at least a part of the surface (preferably the whole surface) of the medical device that—upon proper use—comes into direct contact with body parts for which the medical device is intended.

Prefabricated Shaped Articles

In the embodiments where a prefabricated shaped article is involved, the method is designed to provide a coating onto such as shaped article. A wide variety of shaped articles are envisaged (e.g. tubes, wires, lines, stents, catheters, guides, endodontic and orthodontic instruments, needles, trocars for e.g. laparoscopic surgery, laparoscopic accessories, surgical instruments, guide wires), just as a number of different materials may constitute such shaped articles, such as metals and alloys, e.g. stainless steel cores or typical guide-wire alloys, e.g. Ti alloys such as Nitinol and pseudoplastic Beta Ti—Mo—V—Nb—Al alloys. Glasses and ceramics just as thermoplastic polymers are also envisaged. Suitable materials also include: Thermoplastic polymers such as hydrophilic polyurethanes, hydrophobic polyurethanes, polyether block amides (e.g. Pebax™), PVC, polyamides, polyesters, biodegradable polyesters, polyacrylates, PS, silicones, latex rubber; block copolymers with the different structures diblock (A-B), multiblock $(A-B)_n$ or triblock (A-B-A) such as SEBS, SIS, SEPS, SBS, SEEPS (the block copolymers may be grafted with maleic anhydride onto the rubber block, typically the mid-block for triblock copolymers); thermoplastic polymers such as LDPE, LLDPE, VLDPE, PP, PE, and copolymers of ethylene and propylene, metallocene polymerized polyolefins, PS, EMA, EEA, EnBA, PE g-MAH, EVA, EVOH and vinyl acetate copolymer grafted with maleic anhydride (EVA g-MAH), or combinations thereof e.g. Orevac® ethylene-vinyl acetate-maleic anhydride terpolymers; and the functional polyolefins range, such as Lotader® ethylene-acrylic ester terpolymers with either MAH or GMA; and the maleic anhydride grafted polymers of PE, PP, PS, etc. The abbreviations are explained in the Table in Examples.

Thermoplastic Substrate Polymer

In the embodiments where a thermoplastic substrate polymer is involved, the method is designed to provide a coating onto this substrate. The thermoplastic substrate polymer is selected so as to provide the physical shape of the medical device element or so as to provide a suitable interface between the coating composition and the prefabricated shaped article. Hence, the substrate polymer is typically selected from polyurethanes, polyether block amides (e.g. Pebax™), PVC, polyamides, polyesters, polyacrylates, PS, silicones, latex rubber, SEBS, SIS, SEPS, SEEPS, EVA, PE, and copolymers of ethylene and propylene; thermoplastic polymers such as hydrophilic polyurethanes, hydrophobic polyurethanes, polyether block amides (e.g. Pebax™), PVC, polyamides, polyesters, polyacrylates, PS, silicones, latex rubber; block copolymers with the different structures diblock (A-B), multiblock (A-B), or triblock (A-B-A) such as SEBS, SIS, SEPS, SBS, SEEPS; the block copolymers maybe grafted with MAH onto the rubber block, typically the mid-block for triblock copolymers; thermoplastic polymers such as LDPE, LLDPE, VLDPE, PP, PE, and copolymers of ethylene and propylene, metallocene polymerized polyolefins, PS, EMA, EEA, EnBA, PE g-MAH, EVA, EVOH and EVA g-MAH, or combinations thereof, e.g. Orevac® ethylene-vinyl acetate-maleic anhydride terpolymers; the functional polyolefins range, such as Lotader® ethylene-acrylic ester terpolymers with either MAH or GMA; maleic anhydride grafted polymers of PE, PP, PS, etc.; and the EPOCROS K-series of reactive acrylate-oxazoline copolymers or the RPS/RAS-series of styrene-oxazoline copolymers, or styrene-acrylonitril-oxazoline copolymers.

Currently very relevant materials for use as the thermoplastic substrate polymer are polyurethanes and PVC, in particular polyurethanes, e.g. hydrophobic polyurethanes.

Coating Composition

The principal constituents of the coating composition are the thermoplastic matrix polymer, the hydrophilic polymer and the one or more photo-initiators. These constituents will be discussed in detail further below.

The matrix polymer and the hydrophilic polymer are preferably used in a relative weight ratio from 95:5 to 5:95, in particular from 80:20 to 20:80, or from 75:25 to 30:70.

Depending on the intended use, additives may be incorporated into the coating composition in order to achieve particular properties. For example one or more additives such as flow aids, flatting agents, heat stabilizers, surface cure modifiers, antibacterial agents, and osmolality increasing compounds may be added to the coating composition. Such additives and their use to modify polymer properties are conventional and well known to those skilled in the art. Such other components may be used in an amount of up to 10% by weight, e.g. up to 5% by weight, of the coating composition.

Antibacterial agent may be a silver salt, e.g. silver sulphadiazine; an acceptable iodine source such as povidone iodine (also called PVP iodine); chlorhexidine salts such as the gluconate, acetate, hydrochloride or the like; or salts or quaternary antibacterial agents such as benzalkonium chloride or other antiseptics or antibiotics. Antibacterial agents reduce the risk of infection, e.g. when urodynamic examinations are performed.

For medical devices or instruments suitable for introduction into human cavities, it may be advantageous to include an osmolality increasing compound, e.g. a water-soluble non-ionic compound such as glucose, sorbitol, glycerin, or urea; or ionic compounds such as halides, nitrates, acetates, citrates or benzoates of alkali metals or alkaline earth metals or silver; or carboxylic acids such as acetic acid, etc.

For some hydrophilic polymers, e.g. PVP, it may be necessary or desirable to include a plasticizer in order to facilitate the extrusion, injection moulding or powder coating. In such instances, a plasticizer may be included in an amount of up to 60% by weight of the coating composition.

In one embodiment, the coating composition preferably comprises:
20-80% by weight of the matrix polymer,
20-80% by weight of the hydrophilic polymer,
0-60% by weight of one or more plasticizers
0.0001-5.0% by weight of the one of more photo-initiators, and
0-5% by weight of other components.

In a more interesting embodiment, the coating composition comprises:
20-80% by weight of the matrix polymer,
20-80% by weight of the hydrophilic polymer,
0-5% by weight of one or more plasticizers,
0.0001-5.0% by weight of the one of more photo-initiators, and
0-5% by weight of other components.

In a particular embodiment, the coating composition comprises:
30-75% by weight of the matrix polymer being a hydrophilic polyurethane,
25-70% by weight of the hydrophilic polymer being a PEO,
0.001-2.5% by weight of the one of more photo-initiators, and
0-5% by weight of other components.

In another particular embodiment, the coating composition comprises:
30-75% by weight of the matrix polymer being a hydrophilic polyurethane,
25-50% by weight of the hydrophilic polymer being a PEO,
0-60% by weight of one or more plasticizers
0.001-2.5% by weight of the one of more photo-initiators, and
0-5% by weight of other components.

Thermoplastic Matrix Polymer

The main requirement to the matrix polymer is the thermoplasticity. Moreover, the thermoplastic polymers should preferably be limpid (i.e. clear, non-opaque) at the temperature of photo-curing. The thermoplastic matrix polymers as such should preferably have low absorbance in the UV-C part of the electromagnetic spectrum (i.e. wavelengths below 280 nm), which is where most photo-initiators have their maximum absorbance. Preferably, the absorbance of the thermoplastic polymers in UV-B (280-315 nm) and UV-A (315-380 nm) should also be low, since some photo-initiators absorb in that region.

Examples of suitable thermoplastic matrix polymers are those of the type defined for the thermoplastic substrate polymer (see the section "Thermoplastic Substrate polymer"). Suitable thermoplastic matrix polymers include MAH-modified PE (e.g. Orevac®) and MAH-modified PP (e.g. Fusabond®). Polyurethanes, in particular hydrophilic polyurethanes (including polyetherurethanes), are particularly useful. Furthermore, amphiphilic block copolymers can also be particularly useful for use as the thermoplastic matrix polymer.

A group of preferred thermoplastic matrix polymers are the hydrophilic polyurethanes Tecogel 500 and Tecogel 2000 from Noveon, or Hydromed TP from Cardiotech. The thermoplastic polymer should be able to swell at least 80% in water, so the medical device does not dry out during normal use. The main function of the thermoplastic matrix polymer(s) is to make the entire coating composition thermoplastic and hence suitable for (co)extrusion or injection moulding, even though the additionally added hydrophilic polymer(s) and photo-initiator(s) may not be thermoplastic per se.

Thermoplastic polyurethanes prepared from polyisocyanates, high molecular weight polyetherglycols, and low molecular weight diols and diamines as chain extenders are conventionally referred to as polyetherurethanes, and this term will be used herein for polyurethanes having a polyether backbone.

Polyetherurethane compositions develop micro-domains conventionally termed "hard segment domains" and "soft segment domains" and are often referred to as segmented polyurethanes. They are $(AB)_n$ type block copolymers, A being the hard segment and B the soft segment. The hard segment domains form by localization of the portions of the copolymer molecules which include the isocyanate and extender components whereas the soft segment domains form from the polyether glycol portions of the copolymer chains. The phase separated micro-domain structure forms if the hard segments of polyetherurethane chain have a certain size. A long hard segment promotes the phase separated micro-domain structure. Conversely, non-extended formulations (those lacking an extender) have very short hard segments and minimum phase separated micro-domain structure. The hard segment is crystalline and provides physical cross-linking and reinforcement. The polyether glycol soft segment is mostly in a rubbery state and provides elasticity. Therefore, polyetherurethanes are thermoplastic elastomeric materials. A wide range of physical properties can be obtained by altering the relative ratios of the hard and soft segments. The elasticity, toughness and other desirable properties of polyetherurethanes are the result of their phase separated microdomain structure.

Hydrophilic polyetherurethanes (HPEUs) suitable for use as the thermoplastic matrix polymer of the coating composition include three essential components, a diisocyanate, a polyether glycol and a chain extender. Suitable diisocyanates are aromatic diisocyanates such as MDI, alicyclic diisocyanates such as isophorone diisocyanate and methylene-4,4'-dicyclohexyldiisocyanate, and aliphatic diisocyanates, as, for example, hexamethylene diisocyanate. The most preferred diisocyanate is MDI.

The polyether glycol component may be PEG, alone or mixed with poly(1,2-propylene oxide) glycol or poly(tetramethylene oxide) glycol. The preferred polyol is PEG having a molecular weight of from about 600 to 8,000, or a mixture containing 50% or more by weight thereof. The most preferred polyether glycol is a PEG having an average molecular weight of 1000 to 1450. In order to reduce the crystallinity of the PEG domains, polyether polyols based on either random or block copolymers of ethylene oxide/1,2-propylene oxide or the Tegomer® D 3403, a polyether diol can be chosen.

The chain extender may be water and/or a low molecular weight branched or unbranched diol, diamine or aminoalcohol of up to 10 carbon atoms or mixtures thereof. Representative nonlimiting examples of chain extenders are BDO; ethylene glycol; diethylene glycol; triethylene glycol; 1,2-propanediol (propylene glycol); 1,3-propanediol; 1,6-hexanediol; 1,4-bis(hydroxymethyl)cyclohexane; hydroquinone dihydroxyethyl ether; ethanolamine; ethylenediamine; and hexamethylenediamine. Preferred chain extenders are 1,6-hexanediol; ethylenediamine; hexamethylenediamine and, most preferably, BDO.

The percentages of the components may be such that the hard and soft segments of the composition may be from 25% to 60% and from 40% to 75%, respectively, preferably from 30% to 50% and from 50% to 70%, respectively, of the total weight of the formulation. From these percentages and ratios, suitable proportions of the components may readily be calculated. Representative elastomeric segmented HPEU matrix polymers and their preparation are known from U.S. Pat. No. 5,061,424 (Example I). The HPEU matrix polymer may be prepared by solution or bulk synthesis methods. Alternatively, the HPEU may be prepared by conventional emulsion polymerization in water, to give an HPEU latex.

Amphiphilic block polymers consist of a non-polar polymeric chain coupled to a polar polymeric chain. More in particular the polar chain end of the polymer must be water-soluble or water swellable to at least a content of 300% water if taken alone. The non-polar chain preferably does not take up more than 10% of water when submersed in water.

The polymers are made from two or more monomers each of which are grouped in blocks. The polymers may for instance be a diblock from monomers A and B having a structure AAAAAABBBBBB or a triblock having a linear structure like AAAABBBBAAAA or alternatively in the form of a multiblock or a three- or multiarm star-shaped copolymer structure.

The incorporation of amphiphilic block copolymers having long hydrophobic end blocks as diblock, triblock, multiblock or star-shaped block copolymers improves the cohesion dramatically compared to the incorporation of conventionally used associative thickeners. Due to the physical cross-linking the amphiphilic block copolymers maintain the high cohesion in the coating during hydration and water absorption.

The hydrophobic block of the block copolymer will constitute separate physically cross-linked domains being incompatible with the continuous hydrophilic phase.

The hydrophobic part of the amphiphilic block copolymer may suitably be polystyrene; polyethylene; a poly($\alpha$-olefin) such as polypropylene, poly(1-butene) or polyisobutylene; a poly(meth)acrylate, a poly(vinyl ether), a poly(vinyl acetate), a polysiloxane, a hydrophobic polyester or similar polymer moieties conventionally used in pressure sensitive adhesive formulations.

The hydrophilic part of the amphiphilic block copolymer (B block) may suitably be any type of polymer that will be able to absorb significant amounts of water. If taken alone, the hydrophilic block is water-soluble or at least highly water absorbing. Suitable polymers for use in amphiphilic polymers for use in accordance with the present invention are PEG (poly(ethylene glycol)), PVP (poly(vinyl pyrrolidone)), poly(acrylic acid), salts of poly(acrylic acid), salts of polymers composed of other mono- and diacids such as maleic acid, fumaric acid, crotonic acid, tiglic acid, and itaconic acid; poly(vinyl alcohol), hydrophilic polyurethanes, carbohydrates or gelatins. The hydrophilic block preferably has a minimum molecular weight of about 500 g/mol in order to be able to form separate hydrophilic domains in the coating composition. Preferably the molecular weight is higher than 1000 g/mol in case of end-blocks and higher than 5000 g/mol in case of mid-blocks.

For use in accordance with the present invention it is suitable that the amphiphilic polymer contains polystyrene blocks. In a suitable alternative embodiment of the invention the amphiphilic polymer contains hydrophobic polyacrylate blocks.

In a further embodiment of the invention the amphiphilic polymer contains hydrophobic blocks from the polymer of a vinylic, unsaturated aliphatic hydrocarbon comprising from 1 to 6 carbon atoms, the 4 carbon vinylic, unsaturated hydrocarbons polybutylene and polyisobutylene being most preferred.

In the preferred amphiphilic block copolymers to be used in accordance with the present invention the hydrophobic A domain is a thermoplastic homopolymer with a number average molecular weight of about 1000 to about 50,000 g/mol of an aromatic monovinyl compound, and the hydrophilic B domain has a number average molecular weight of about 1000 to about 500,000 g/mol.

Hydrophobic monomers for use in the A block are aromatic monovinyl compounds, which typically contain from about 8 to about 18 carbon atoms, such as styrene, $\alpha$-methylstyrene, vinyltoluene, vinylpyridine, ethylstyrene, tert-butylstyrene, iso-propylstyrene, dimethylstyrene, and other alkylated styrenes. The A block could also suitably consist of acrylic esters or vinyl esters.

Alternatively, the A domain may comprise ethylenically unsaturated monomers chosen from butadiene, chloroprene, (meth)acrylic esters, vinyl halides such as vinyl chloride, vinyl nitriles, and vinyl esters such as vinyl acetate, vinyl versatate and vinyl propionate.

"(Meth)acrylic esters" is used in the present context to designate esters of acrylic acid or methacrylic acid with optionally halogenated, e.g. chlorinated or fluorinated, $C_1$-$C_{12}$ straight or branched alcohols, preferably $C_1$-$C_8$ alcohols. Examples of such esters are methyl acrylate, ethyl acrylate, propyl acrylate, n-butyl acrylate, isobutyl acrylate, 2-ethylhexyl acrylate, tert-butyl acrylate, methyl methacrylate, ethyl methacrylate, n-butyl methacrylate and isobutyl methacrylate.

Suitable vinyl nitriles are those having from 3 to 12 carbon atoms, such as, in particular, acrylonitrile and methacrylonitrile.

In another embodiment of the present invention styrene is completely or partly replaced by derivatives of styrene, such as α-methylstyrene or vinyltoluene.

The preferred hydrophilic B block for a diblock or triblock copolymer will be described in more detail below.

Hydrophilic monomers for use in the B block are e.g. ethylenically unsaturated monocarboxylic and dicarboxylic acids, such as acrylic acid, methacrylic acid, itaconic acid, maleic acid and fumaric acid; and monoalkyl esters of dicarboxylic acids of the type mentioned above with alkanols, preferably alkanols having from 1 to 4 carbon atoms, optionally with unalkylated or alkylated amino groups; amides of unsaturated carboxylic acids, such as acrylamide, methacrylamide, N-methylolacrylamide, N-methylolmethacrylamide, and N-alkylacrylamides; ethylenic monomers containing a sulphonic acid group and ammonium or alkali metal salts thereof, for example S-vinylsulphonic acid, vinylbenzenesulphonic acid, 2-acrylamido-2-methylpropanesulphonic acid (AMPS) and 2-sulphoethyl methacrylate; amides of vinylamine, especially N-vinylformamide or N-vinylacetamide; and unsaturated ethylenic monomers containing a secondary or tertiary amino group or a quaternary ammonium group, or a heterocyclic group containing nitrogen, such as, for example, vinylpyridines or vinylimidazole; aminoalkyl (meth)acrylates such as dimethylaminoethyl (meth)acrylate and di-tert-butylaminoethyl (meth)acrylate, N,N-dialkyl(meth)acrylamides such as N,N-dimethyl(meth)acrylamide. It is also possible to use zwitterionic monomers such as, for example, N,N-dimethyl-N-methacryloyloxyethyl-N-(3-sulphopropyl) ammonium betaine (SPE).

In the currently most preferred embodiments, the thermoplastic matrix polymer is selected from the group consisting of hydrophilic polyurethane polymers and amphiphilic block-copolymers.

It should be understood that the expression "a thermoplastic matrix polymer" and the like is intended to encompass a single thermoplastic polymer as well as a mixture of two or more thermoplastic polymers.

Hydrophilic Polymer

The main requirement to the hydrophilic polymer is to ensure that the covalently cross-linked coating composition becomes very slippery when it is swollen with hydrophilic liquids such as water or glycerol. Hence, the main function of the hydrophilic polymer(s) is to give the swollen coating low friction and high water retention.

The hydrophilic polymer is preferably also limpid at the temperature of photo-curing and has low absorbance in UV-C, UV-B and UV-A, so that it does not block the UV or visible light intended for the photo-initiator(s). The hydrophilic polymer may suitably be selected from one or more of the following materials:

Poly(vinyl lactams) such as PVP; and copolymers of NVP and DMAEMA, (meth)acrylic acid, (meth)acrylic esters including 2-sulfoethyl methacrylate, (meth)acrylic amides including N,N-dimethylacrylamide and N-vinylacetamide, MAH, maleic esters, P-vinylphosphonic acid, methyl vinyl ether, etc.

Slightly cross-linked PVP or PVP copolymers are preferred.

Linear or, preferably, cross-linked PEO with high molecular weight, and copolymers of EO and PO.

Superabsorbent homo- and copolymers of water-soluble α,β-ethylenically unsaturated carboxylic acids and derivatives, such as acrylic acid, methacrylic acid, fumaric acid, maleic acid, crotonic acid, tiglic acid, and itaconic acid; and their esters and amides.

Cellulosic superabsorbent polymers, e.g. hydroxypropyl methylcellulose or CMC, or starch-graft copolymers, such as starch-graft-polyacrylonitrile, starch-graft-poly (acrylic acid) and the like.

PVOH, homo- and copolymers of sulphonic acid group containing monomers, such as S-vinylsulphonic acid, sodium sulfoethyl methacrylate, 2-acrylamido-2-methylpropane-sulphonic acid or the sodium salt (AMPS) and the like.

A/t-copoly(methyl vinyl ether/maleic anhydride) (tradename Gantrez at ISP Corporation) which has been either hydrolyzed in basic solution (to form a polyanion), hydroxy-modified (to form an ester acid) or amino-modified (to form an amide acid).

Poly(vinyl methyl ether), polyethyleneimine, poly(2-ethyl-2-oxazoline), copoly(2-ethyl-2-oxazoline/2-phenyl-2-oxazoline) as random or block copolymers, or the hydrophilic EPOCROS WS-series, such as WS-500, WS-700.

The preferred hydrophilic polymers are those selected from the group consisting of poly(vinyl lactams) [e.g. PVP], PEO, polyoxazolines, PVOH, and polyacrylates. The currently most preferred hydrophilic polymer is PEO.

When PEO is used a hydrophilic polymer, it may be of any suitable weight average molecular weight ($M_w$), but preferably in the range of 100,000 to 8,000,000, most preferably 200,000 to 4,000,000. Suitable PEOs may be purchased from Dow under the trade name Polyox®.

When PVP is used as a hydrophilic polymer, it may be of any suitable weight average molecular weight ($M_w$), but preferably in the range of 10,000 to 3,500,000. Suitable PVPs may be purchased from ISP Corp. under the tradename Plasdone.

It should be understood that the expression "a hydrophilic polymer" and the like is intended to encompass a single hydrophilic polymer as well as a mixture of two or more hydrophilic polymers.

The choice of materials for the thermoplastic substrate polymer and the thermoplastic matrix polymer depends on the materials chosen for the prefabricated shaped article. Typically, if the prefabricated shaped article is made of a polyurethane, a hydrophilic polyurethane will be chosen as the thermoplastic substrate polymer, and the coating composition will preferably contain a hydrophilic polyurethane as the thermoplastic matrix polymer.

If the prefabricated shaped article is made of a polyolefin, polyolefins will typically be preferred as a thermoplastic substrate polymer and often in combination with more polar polymers or polymers with functional groups, which can introduce compatibility with the final hydrophilic lubricious coating.

In order to improve and obtain a proper surface anchoring between different layers on prefabricated shaped articles there will be several strategies. In some cases di- or triblock copolymers with one or more polyolefinic groups together with more polar PS block(s) can give an optimal surface anchoring between layers. Otherwise the substrate polymer can be modified during reactive polymer blending where functional groups on the polymers can be utilized to combine non-polar polymers with polar or hydrophilic polymers.

Reactive polymer blending can also be used to obtain covalent bonding between photo-initiators and non-polar, polar or hydrophilic functional polymers in order to improve surface anchoring during a photo-curing after a co-extrusion of the coatings.

When the term "polymer" is used herein, e.g. connection with the expressions "thermoplastic matrix polymer" and "hydrophilic polymer", it typically implies that the weight average molecular weight is more than 10 kDa. The molecular weight limit range provided for "polymers" is hence complementary to the limit given for "low molecular weight", i.e. up to 10 kDa".

Photo-Initiators

The presence of one or more photo-initiators in the coating composition is mandatory. The one or more photo-initiators are typically present in an amount of in the range of 0.001-10 w/w-%, such as in the range of 0.01-5 w/w-%, in particular in the range of 0.1-4 w/w-%.

The main function of the photo-initiator(s) is to ensure good cross-linking of the thermoplastic, hydrophilic coating to itself and to the substrate, in order to obtain good cohesion and adhesion to the substrate.

As will be understood from the following, the one or more photo-initiators may be present in the coating composition (a) as discrete molecules, (b) as photo-initiators covalently linked to a polymer, or (c) as a plurality of photo-initiator moieties covalently linked to a low molecular weight scaffold, or a combination thereof. This will be discussed in more detail below.

In one possible embodiment, which also will be described in more details in the following, the one or more photo-initiators are covalently linked to molecules of a polymer, e.g. the thermoplastic matrix polymer and/or to molecules of the hydrophilic polymer and/or a third polymer not being the thermoplastic matrix polymer or the hydrophilic polymer.

In one variant hereof, the one or more photo-initiator moieties are covalently linked to a polymer selected from the group consisting of polyurethanes, polyethylene glycols, poly(lactic acid)s, collagen, nylons (e.g. polycaprolactam, polylauryl lactam, polyhexamethylene adipamide and polyhexamethylene dodecanediamide), vinyl polymers (e.g. polyvinyl pyrrolidone and polyvinyl alcohol), and polysaccharides (e.g. amylose, dextran, chitosan, hyaluronic acid, amylopectin, hyaluronic acid and hemi-celluloses).

The one or more photo-initiators efficiently transform light from the UV or visible light source to reactive radicals which can abstract hydrogen atoms and other labile atoms from polymers and hence effect covalent cross-linking. Optionally, amines, thiols and other electron donors may be added. Radical photo-initiators can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991).

Upon excitation cleavable photo-initiators spontaneously break down to two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photo-initiators. Addition of electron donors is not required but may enhance the overall efficiency of cleavable photo-initiators according to a mechanism similar to that described for the non-cleavable photo-initiators below.

Recently a new class of β-keto ester based photo-initiators has been introduced by M. L Gould, S, Narayan-Sarathy, T. E. Hammond, and R. B. Fechter from Ashland Specialty Chemical, USA (2005): "Novel Self-Initiating UV-Curable Resins: Generation Three", Proceedings from RadTech Europe 05, Barcelona, Spain, Oct. 18-20 2005, vol. 1, p. 245-51, Vincentz. After base-catalyzed Michael addition of the ester to polyfunctional acrylates a network is formed with a number of quaternary carbon atoms, each with two neighbouring carbonyl groups. Upon UV or visible light excitation these photo-initiators predominantly cleave by a Norrish type I mechanism and cross-link further without any conventional photo-initiator present, and thick layers may be cured. Such self-initiating systems are within the scope of the present invention.

Excited non-cleavable photo-initiators do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. Benzophenones, thioxanthones, xanthones, anthraquinones, fluorenones, dibenzosuberones, benzils, and phenyl ketocoumarins are important examples of non-cleavable photo-initiators. Most amines with a C—H bond in α-position to the nitrogen atom and many thiols will work as electron donors.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition the strong UV absorption of the maleimide disappears in the polymer, i.e. maleimide is a photobleaching photo-initiator; this could make it possible to cure thick layers. Such maleimide-containing systems are within the scope of the present invention.

The preferred cleavable photo-initiators are benzoin ethers (including benzil dialkyl ketals) such as Irgacure 651 (Ciba); phenyl hydroxyalkyl ketones such as Darocur 1173, Irgacure 127, Irgacure 184, and Irgacure 2959 (all from Ciba), Esacure KIP 150 and Esacure One (both from Lamberti); phenyl aminoalkyl ketones such as Irgacure 369 (Ciba), Irgacure 379 (Ciba), and Chivacure 3690 (from Double Bond Chemical); methylthiophenyl morpholinoalkyl ketones such as Irgacure 907 (Ciba) and Chivacure 3482 (Double bond Chemicals); and mono- or dibenzoylphosphinoxides such as Irgacure 819 and Darocur TPO (both from Ciba).

The preferred non-cleavable photo-initiators are benzophenone; 4-benzoylbenzoic acid (=4-carboxybenzophenone) and esters thereof; 2-benzoylbenzoic acid (=2-carboxybenzophenone) and esters thereof; 4,4'-bis (dimethylamino)benzophenone (Michler's ketone); 2,4,6- trimethylbenzophenone; BTDA; Omnipol BP (IGM Resins), and other benzophenone derivatives; thioxanthones such as Omnipol TX (IGM Resins); xanthones; anthraquinones; fluorenones; dibenzosuberones; benzils and other α-diketo compounds such as camphorquinone; and phenyl ketocoumarins. The preferred optional electron donors are benzocaine (ethyl 4-aminobenzoate), PVP-DMAEMA, tribenzylamine, triethanolamine, 2-(N,N-dimethylamino)ethanol, and N,N-dimethylethylenediamine. The preferred acrylate-containing photo-initiators are Omnilane XP-144 LS-B (light sensitive trifunctional aliphatic urethane acrylate; from IGM/Bomar) and acrylated benzophenones.

The currently most preferred photo-initiators are those selected from the group Irgacure 2959, Irgacure 651, Esacure KIP 150, BTDA and derivatives thereof, 4-carboxybenzophenone and derivatives thereof, and 2-carboxybenzophenone and derivatives thereof.

In one embodiment, one or more identical photo-initiator moieties are present in the coating composition as discrete molecules, i.e. as molecules comprising only one photoactive group.

In one interesting embodiment, the one or more photo-initiator(s) include at least two different photo-initiators. More particular, the one or more photo-initiator(s) comprises at least one cleavable photo-initiator and at least one non-cleavable photo-initiator (see Example 8).

A blend of several photo-initiators may exhibit synergistic properties, as is e.g. described by J. P. Fouassier: "Excited-State Reactivity in Radical Polymerisation Photo-initiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photo-initiator to the other in the pairs [4,4'-bis(dimethylamino)benzophenone+benzophenone], [benzophenone+2,4,6-tri-methylbenzophenone], [thioxanthone+methylthiophenyl morpholinoalkyl ketone]. However, many other beneficial combinations may be envisaged.

Furthermore, it has recently been found that covalently linked Irgacure 2959 and benzophenone in the molecule 4-(4-benzoylphenoxyethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20 2005, vol. 2, p. 375-81, Vincentz. This shows that different photo-initiators may show significant synergistic effects when they are present in the same oligomer or polymer. Such covalently linked photo-initiators are within the scope of the present invention.

The preferred properties of the photo-initiator(s) are: (i) good overlap between the lamp emission spectrum and the photo-initiator absorption spectrum; (ii) small overlap or no overlap between the photo-initiator absorption spectrum and the intrinsic, combined absorption spectrum of the other components of the coating (i.e. the thermoplastic matrix polymer (e.g. a thermoplastic, hydrophilic polyurethane) and the hydrophilic polymer (e.g. a hydrophilic polymer with lubricant properties)); and good compatibility of the photo-initiator(s) with the thermoplastic matrix polymer (e.g. hydrophilic polyurethane) and preferably also with the hydrophilic polymer of the coating.

In another embodiment, one or more photo-initiators are present in the coating composition as photo-initiators moieties covalently linked to a polymer, e.g. molecules of the thermoplastic matrix polymer, molecules of the hydrophilic polymer, or molecules of a suitable third polymer type. Such a polymer, or polymers, may include one or more identical or different photo-initiator moieties and may therefore represent—in full or in part—the one or more photo-initiators.

The polymer part of the photo-reactive polymer is typically a thermoplastic polymer. Hence, in a particular embodiment, the one or more photo-initiator(s) comprises at least one thermoplastic polymer having photo-reactive groups attached thereto.

As discussed above, it is advantageous to include photo-active polymers or a plurality of photo-initiators covalently linked to a low molecular weight scaffold in the coating composition in order to ensure that the photo-initiation is homogeneously distributed within the coating composition.

In the embodiments where the photo-initiator moieties are covalently attached to molecules of the thermoplastic matrix polymer and/or molecules of the hydrophilic polymer, and it should be understood that only the photo-initiator moieties will contribute to the weight percentage of the one or more photo-initiators, whereas the thermoplastic matrix polymer and the molecules of the hydrophilic polymer will contribute to the weight percentage of thermoplastic matrix polymer and hydrophilic polymer, respectively.

Photoactive polymers may be tailor-made to give optimal compatibility with the thermoplastic matrix polymer and the hydrophilic polymer of the coating composition, optimal cross-linking geometry, and optimal thermoplasticity.

Photoinitiators Linked to a Polymer or Scaffold

A number of illustrative examples of the incorporation of the one or more photo-initiator(s) will be provided in the following so as to emphasis the diversity of means for incorporating the one or more photo-initiators into the coating composition in the form of photo-initiator moieties (illustrated by means of Irgacure 2959 and other commercially available photo-initiator molecules) covalently linked to a polymer (e.g. the thermoplastic matrix polymer or the hydrophilic polymer or a third polymer) or a scaffold.

Irgacure 2959 is a Norrish type I photo-initiator which contains a nucleophilic primary hydroxyl group:

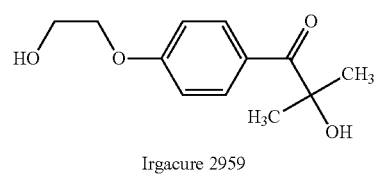 [SMILES: CC(C)(O)C(=O)c1ccc(OCCO)cc1]

Irgacure 2959

The hydroxyl group in Irgacure 2959 may be functionalized to an electrophilic acid derivative in several ways, so that it may react with free hydroxyl and amino groups like BTDA and other benzophenone derivatives, e.g.:

If stronger nucleophilicity is needed, Irgacure 2959 may be sulfonated and then transformed into the corresponding primary amine, e.g. by the Gabriel synthesis (see e.g. J. March: "Advanced Organic Chemistry. Reaction, Mechanisms, and Structure", 3. ed., p. 377-9, Wiley-Interscience, New York, 1985):

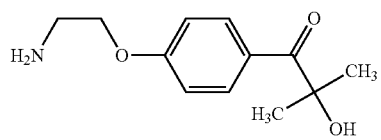

Irgacure 2959 amine

1. Synthesis of the Acid Derived from Cr(VI)-Oxidation of Irgacure 2959:

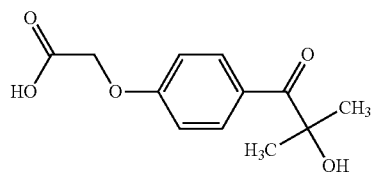

Irgacure 2959 acid

2. Synthesis of the Acid Derived from 1:1 Reaction Between Irgacure 2959 and Succinic Anhydride:

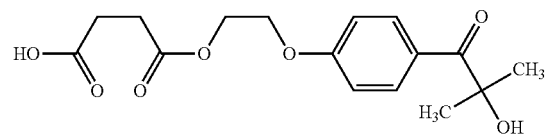

Irgacure 2959-succinic anhydride adduct

3. Synthesis of the Acid Derived from 1:1 Reaction Between Irgacure 2959 and Maleic Anhydride:

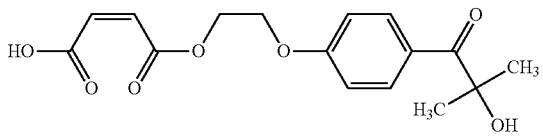

Irgacure 2959-maleic anhydride adduct

Conversely, electrophilic 2- or 4-benzoylbenzoyl chloride may be transformed to a nucleophile by slow addition to a large excess of ethylene glycol, ethanolamine or ethylenediamine in order to form the nucleophilic 1:1 ester or amide, which may e.g. react with polyanhydrides such as Gantrez AN 119 BF and poly(styrene-co-maleic anhydride) (SMA) (see further below), and with isocyanates:

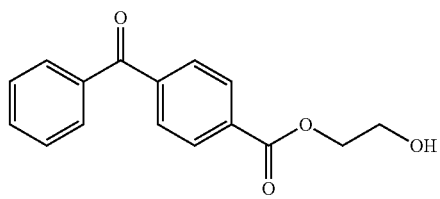

2-Hydroxyethyl 4-benzoylbenzoate

The functionalization of Irgacure 2959 or BTDA or other benzophenone derivatives on Polystyrene-block-polybutadiene-block-polystyrene (SBS) is interesting but not straightforward. For direct one-step coating the double bond of SBS could be hydroxylated and esterified with Irgacure 2959 acid, BTDA, 4-carboxybenzophenone, 2-carboxybenzophenone or others, e.g.:

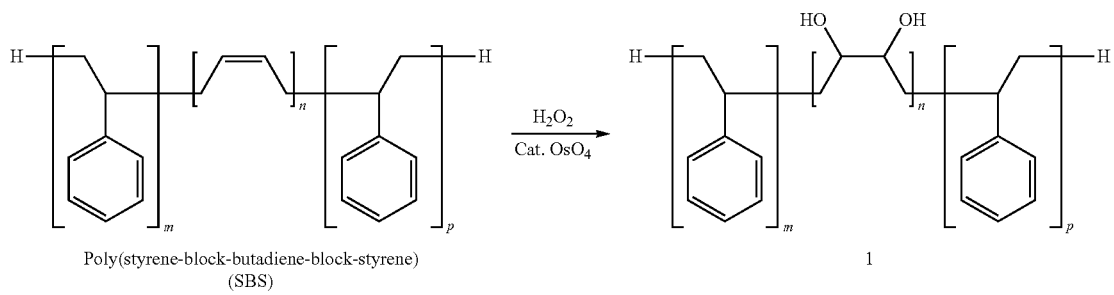

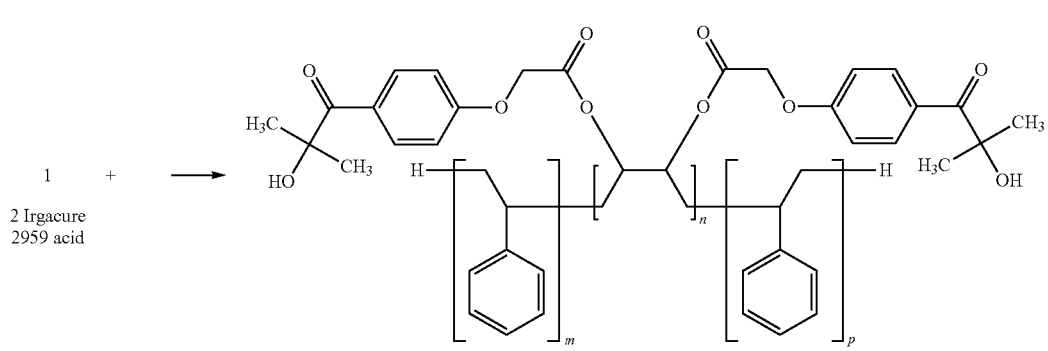

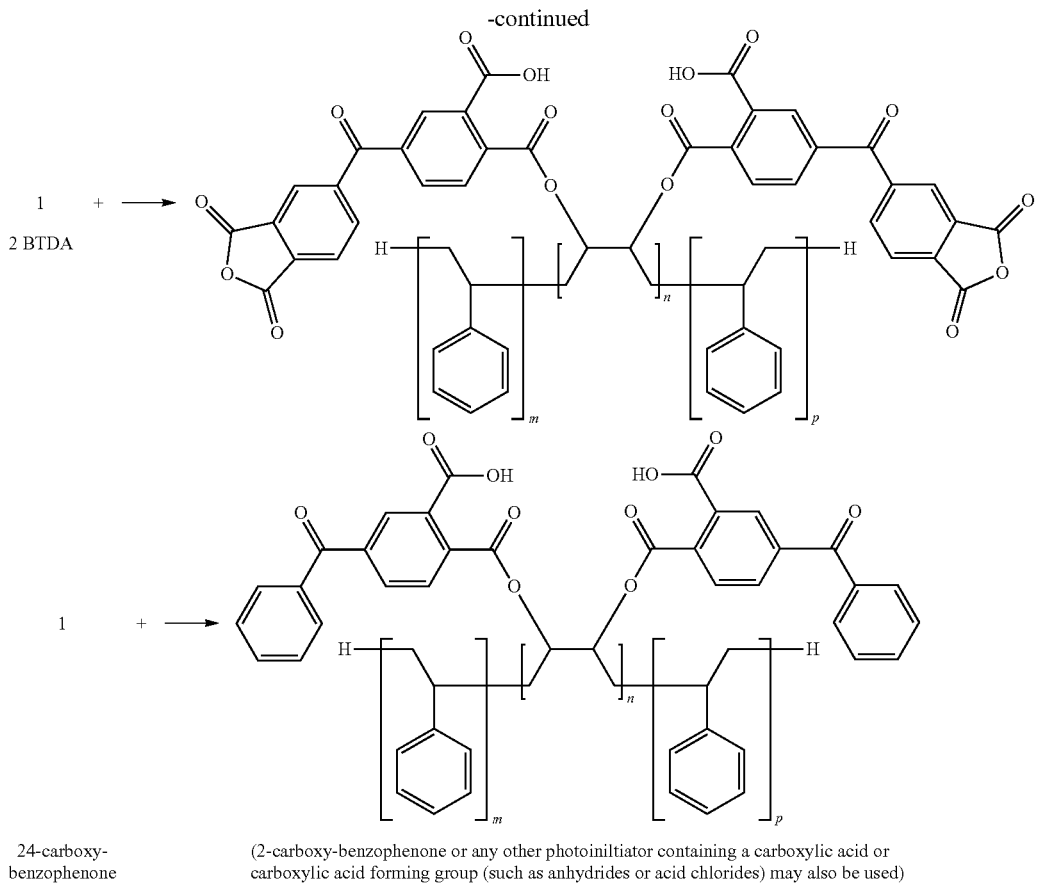

24-carboxy-benzophenone     (2-carboxy-benzophenone or any other photoiniltiator containing a carboxylic acid or carboxylic acid forming group (such as anhydrides or acid chlorides) may also be used)

The aromatic keto groups of the photo-initiators are crucial for the photoactivity, so it must be ensured that the vicinal diols do not form ketals (i.e. 1,3-dioxolane derivatives) in an acid catalyzed process with the keto groups, e.g. for Irgacure 2959:

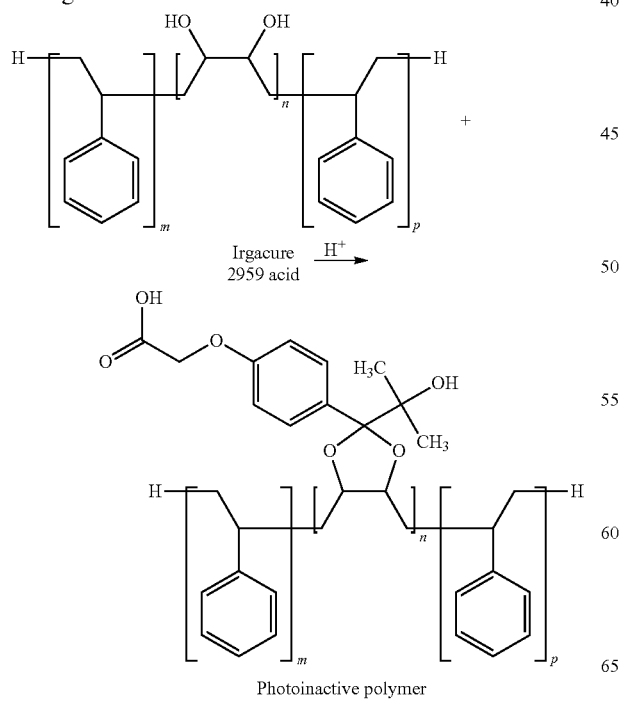

Photoinactive polymer

A coating on SBS may also consist of two layers: A basecoat containing a photo-initiator and a compound that is compatible with SBS, and a topcoat containing the thermoplastic polymer(s), hydrophilic polymer(s), and photo-initiator(s). Usually the concentration of photo-initiator should be higher in the basecoat than in the topcoat in order to get good through curing. After application of both the basecoat and the topcoat the coating must be photo-cured. There are various possibilities:

1. The basecoat may consist of a photo-initiator and a polybutadiene diacrylate (such as BAC-45 with a molecular weight around 3000 Da, but other molecular weights may also be used) from San Esters Corporation. The topcoat should then consist of thermoplastic polymer(s), hydrophilic polymer(s), photo-initiator(s) and (meth)acrylates. After application of both layers the coating should be photo-cured, whereby the primer coat and the topcoat are cross-linked by (meth)acrylate polymerization. San Esters Corporation indicate that the double bonds in SBS usually do not participate in acrylate polymerization (see http://www.sanesters.com/download/BAC-PRESENTATION.PPT).

2. The basecoat may consist of a hydroxyl-terminated polybutadiene, such as Krasol LBH 3000 (Sartomer) or similar, and photo-initiator(s) containing a carboxylic acid or a carboxylic acid forming group (such as an anhydride or an acid chloride). The hydroxyl-terminated polybutadiene and the photo-initiator may then react to form an ester during co-extrusion, injection moulding or dipping, or they may be made to react before application of the basecoat. The topcoat should consist of thermoplastic polymer(s), hydrophilic polymer(s), and photo-initiator(s). After application of both layers the coating should be photo-cured.

3. The basecoat may consist of a hydroxyl-terminated polybutadiene which is further epoxidized along the chain, such as Poly bd 600E or similar from Sartomer, and photo-initiator(s) containing a carboxylic acid or a carboxylic acid forming group (such as an anhydride or an acid chloride). The carboxylic acid or carboxylic acid forming group only reacts with free OH-groups and not with the epoxide itself, so an amine is often added in order to hydrolyze the epoxide ring, according to M. P. Stevens: "Polymer Chemistry. An Introduction", 3. ed., p. 327-8, Oxford University Press, New York, 1999. The hydrolysis may also be performed with aqueous $HClO_4$ or with $HO^-$ in DMSO, according to J. March: "Advanced Organic Chemistry. Reaction, Mechanisms, and Structure", 3. ed., p. 332, Wiley-Interscience, New York, 1985. The hydroxyl-terminated, ring-opened epoxidized polybutadiene may react with the photo-initiator to form an ester during co-extrusion, injection moulding or dipping, or they may be made to react before application of the basecoat. The topcoat should consist of thermoplastic polymer(s), hydrophilic polymer(s), and photo-initiator(s). After application of both layers the coating should be photo-cured.

4. The basecoat may consist of a hydroxyl-terminated polybutadiene which is further epoxidized along the chain, such as Poly bd 600E or similar from Sartomer, and photo-initiator(s) containing a primary hydroxy group, such as Irgacure 2959. The primary hydroxy group can react with epoxides with an acid or a base catalyst to form a β-hydroxy ether, either before or during co-extrusion, injection moulding or dipping:

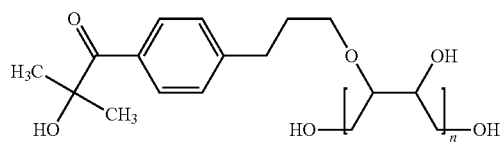

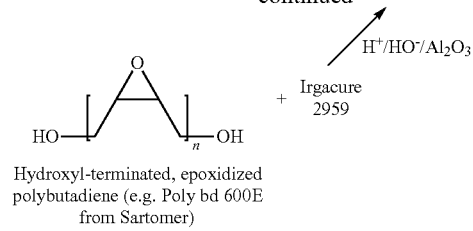

Hydroxyl-terminated, epoxidized polybutadiene (e.g. Poly bd 600E from Sartomer)

The hydroxyl-terminated, ring-opened epoxidized polybutadiene may react further with acidic photo-initiators to form an ester during co-extrusion, injection moulding or dipping, or they may be made to react before application of the basecoat. The topcoat should consist of thermoplastic polymer(s), hydrophilic polymer(s), and photo-initiator(s). After application of both layers the coating should be photo-cured.

5. The basecoat may consist of an isocyanate-terminated polybutadiene, such as Krasol NN-3A from Sartomer, and photo-initiator(s) containing either a carboxylic acid group (in which case the reaction product is an amide after decarboxylation of the initial reaction product) or a hydroxyl group (in which case the reaction product is a urethane). The isocyanate-terminated polybutadiene and the photo-initiator may react to form the product during co-extrusion, injection moulding or dipping, or they may be made to react before application of the basecoat. The topcoat should consist of thermoplastic polymer(s), hydrophilic polymer(s), and photo-initiator(s). After application of both layers the coating should be photo-cured.

HPEU, PEO, poly(1,2-propylene oxide), poly(tetramethylene oxide), sugars, gelatins, hydroxypropyl methylcellulose, starch-graft-polyacrylonitrile, starch-graft-poly(acrylic acid), PVOH, poly(ethyleneimine) and other thermoplastic matrix polymers or hydrophilic polymers, which are terminated with hydroxyl or amino groups, may react with electrophilic photo-initiators such as BTDA, 2- and 4-benzoylbenzoyl chloride, and Irgacure 2959 acid chloride to form the corresponding photo-active esters or amides. For example, BTDA may react with HPEU to form the following polymers:

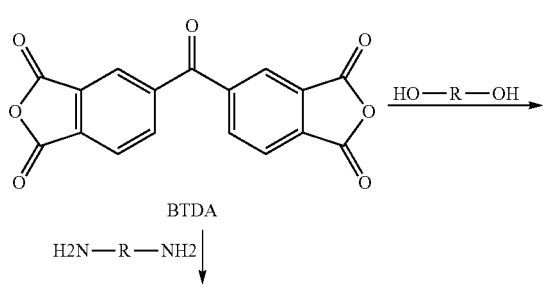

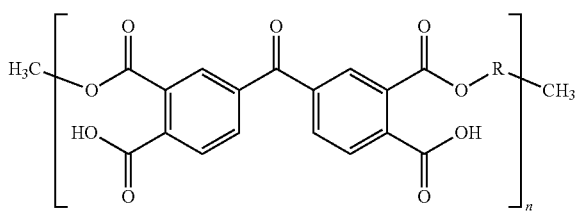

Photoactive poly(ester urethane acid)

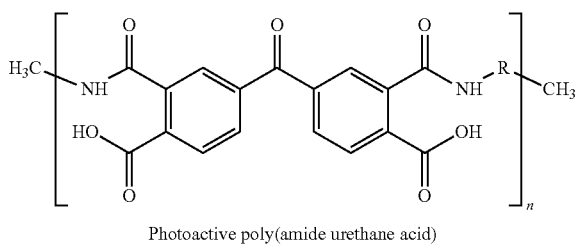

Photoactive poly(amide urethane acid)

The cross-linking reaction of the photoactive BTDA-based poly(ester urethane acid) will be:

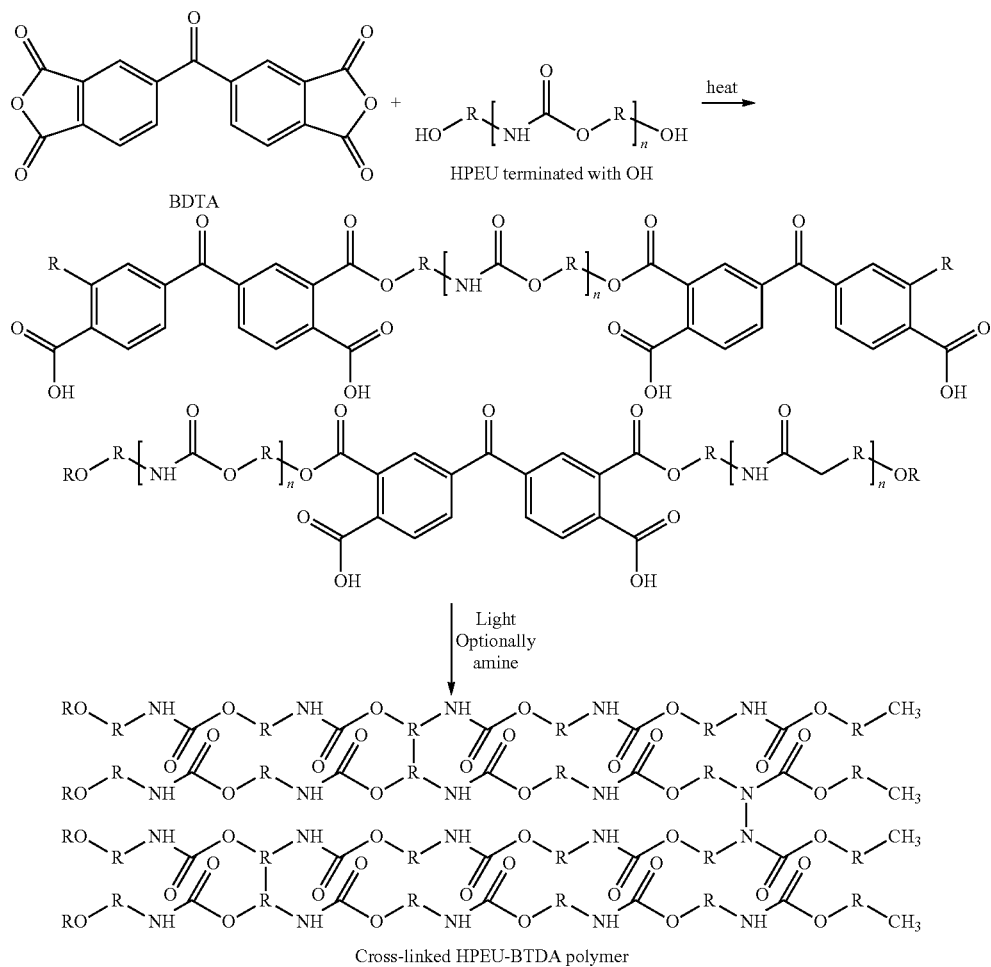

Poly(amide acids) are formed from BTDA and diamine at room temperature. They should have greater hydrolytic stability than poly(ester acids) and hence be preferred over the esters. The acid groups make the properties of the polyamide acids pH dependent: At increasing pH their viscosity (and solubility) should increase in water, and at low pH (i.e. as neutral species) they should be soluble in polar organic solvents such as DMSO, DMA, DMF, and NMP; together with pyridine these solvents are also best for the synthesis of amide acids.

Jeffamine D-230 (hydrophobic; a=2-3, b=c=0) shown below as diamine (from Huntsman) will reacted willingly with BTDA:

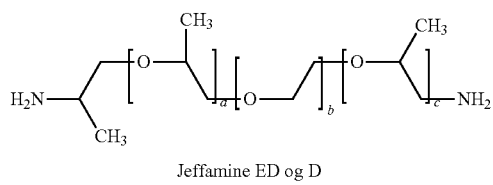

Jeffamine ED og D

Polyanhydrides might be functionalized with Irgacure 2959 (from Ciba):

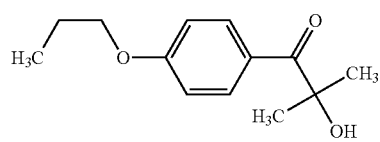

Irgacure 2959

As mentioned above, BTDA may react with the hydroxyl end groups of PEO (Polyox) and other polyethers or with amino groups in poly(ethyleneimine) or other hydrophilic polymers. Upon photo-curing of Polyox a stable, cross-linked, hydrophilic polymer network is formed, which becomes very slippery when wet:

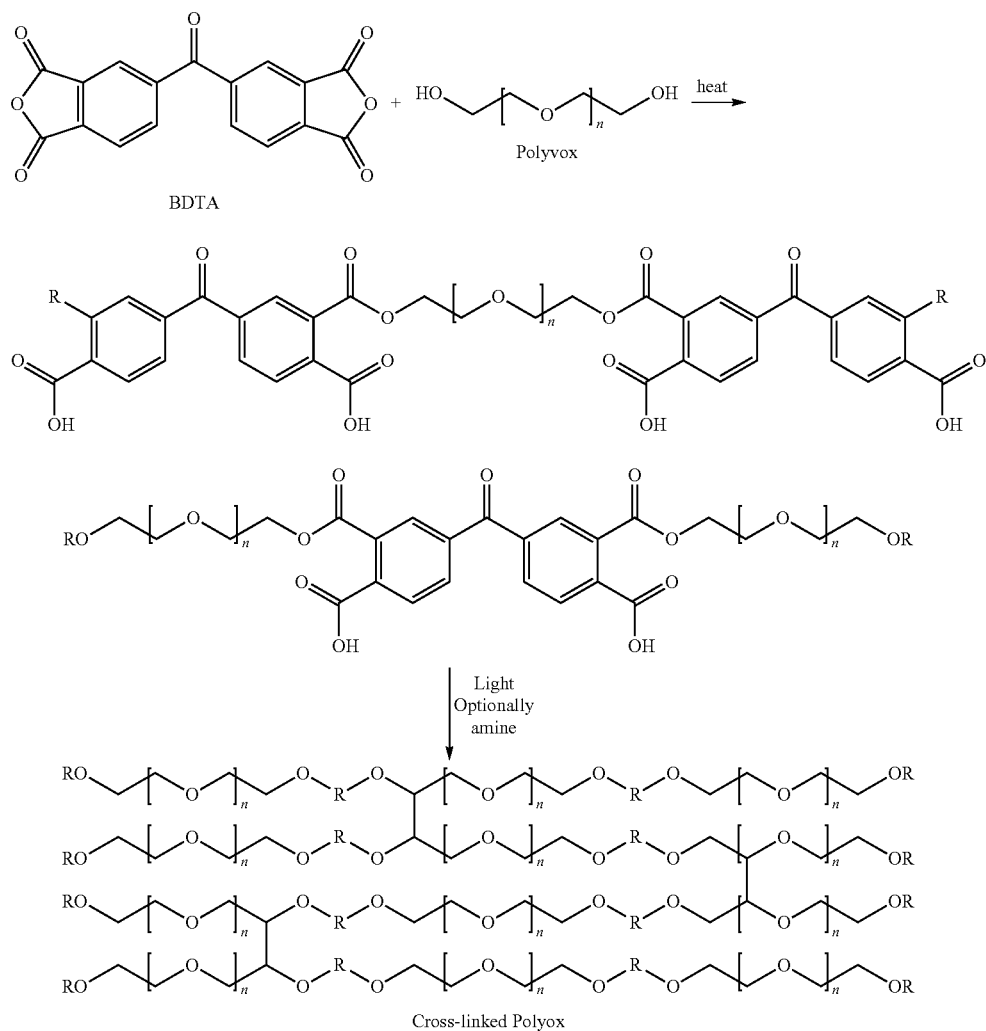

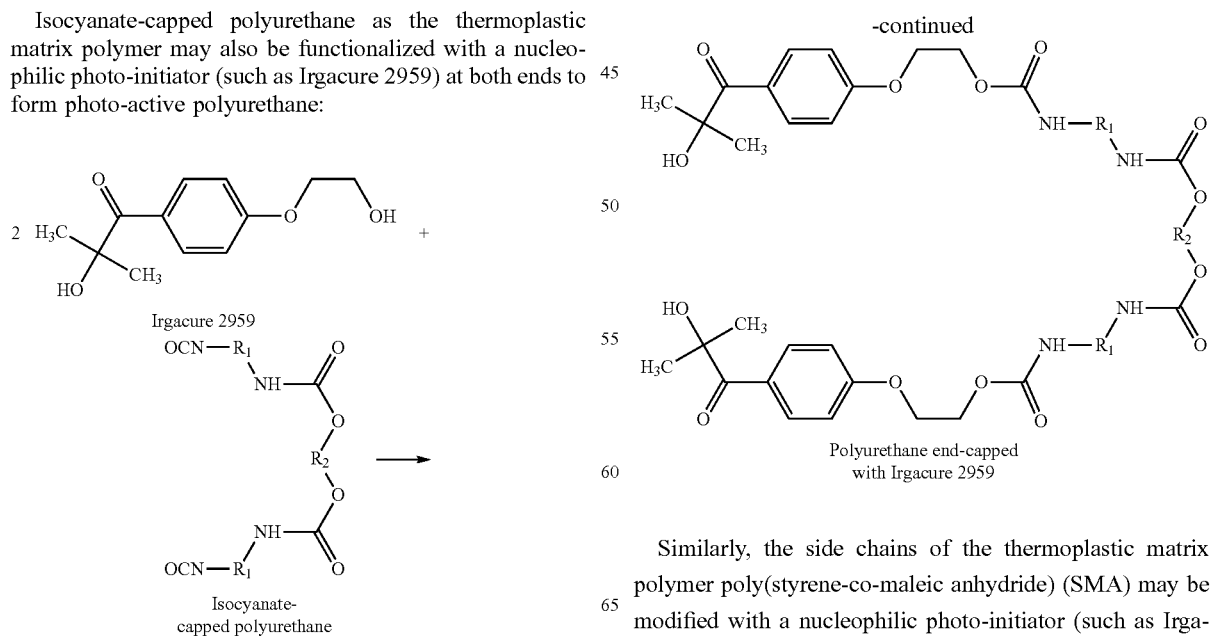

Isocyanate-capped polyurethane as the thermoplastic matrix polymer may also be functionalized with a nucleophilic photo-initiator (such as Irgacure 2959) at both ends to form photo-active polyurethane:

Similarly, the side chains of the thermoplastic matrix polymer poly(styrene-co-maleic anhydride) (SMA) may be modified with a nucleophilic photo-initiator (such as Irgacure 2959 or modified benzophenones):

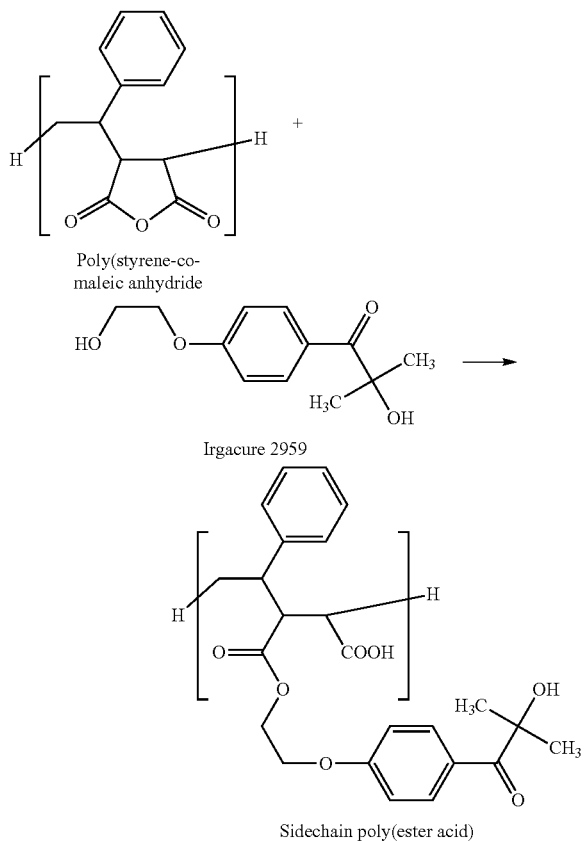

Poly(styrene-co-maleic anhydride)

Irgacure 2959

Sidechain poly(ester acid)

The hydrophilic polymer Gantrez AN-119 [=poly(maleic anhydride-alt-methyl vinyl ether)] may also be functionalized with Irgacure 2959 at the side chains:

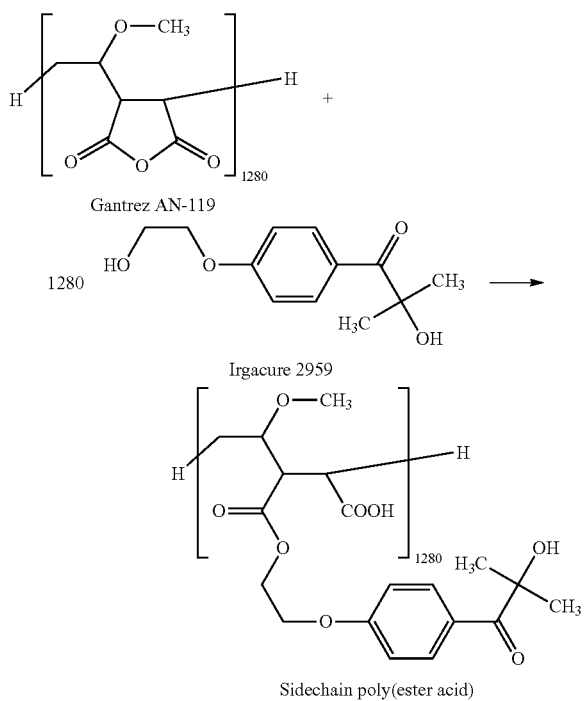

Gantrez AN-119

Irgacure 2959

Sidechain poly(ester acid)

Acidic components of the thermoplastic matrix polymer and the hydrophilic polymer may be transformed to the corresponding acid chlorides, sulphonyl chlorides or phosphonyl chlorides by treatment with $SOCl_2$ or $PCl_5$. Alternatively, the acids may be treated with a dehydrating agent, such as N,N'-dicyclohexylcarbodiimide, to species resembling acid anhydrides in reactivity towards nucleophiles. Such acid chlorides, sulphonyl chlorides and phosphonyl chlorides and the corresponding anhydrides are activated towards reaction with nucleophilic photo-initiators [such as Irgacure 2959, 2- or 4-hydroxybenzophenone, N-(2-hydroxyethyl)-2-benzoylbenzamide, N-(2-hydroxyethyl)-4-benzoylbenzamide, N-(2-aminoethyl)-2-benzoylbenzamide, and N-(2-aminoethyl)-4-benzoylbenzamide] to form the respective esters, amides, sulphonyl esters, sulphonamides, phosphonyl esters, and phosphonamides. The acidic components of the thermoplastic matrix polymer and the hydrophilic polymer include homo- and copolymers of (meth) acrylic acid; maleic acid; fumaric acid; crotonic acid; tiglic acid; itaconic acid; monoalkyl esters of dicarboxylic acids; S-vinylsulphonic acid; vinylbenzenesulphonic acid; 2-acrylamido-2-methylpropanesulphonic acid (AMPS); 2-sulphoethyl methacrylate; P-vinylphosphonic acid; carboxyl-containing carbohydrates, such as pectin, alginates, CMC, furcellaran, carrageenans, gum arabic, gum tragacanth, and xanthan gum; gelatin; and starch-graft-poly(acrylic acid).

Photoactive esters and amides may be formed with excess photo-active nucleophiles and electrophiles by transesterification, transamidation or acidolysis of esters from the thermoplastic matrix polymer and the hydrophilic polymer. Catalysts (such as manganese or zinc salts) may be added, and a vacuum may be applied if the photoinactive component to be removed has a lower boiling point than the photoactive component, so as to remove the photoinactive component from the equilibrium. There are three possibilities of reaction, as the polymer side of the ester may be both the acyl part (as e.g. in polyacrylates) and the alkoxyl part (as e.g. in poly(vinyl acetate)):

Polymer-CO—OR+HO-Photo-initiator→Polymer-CO—O-Photo-initiator+HO—R (transesterification)

Polymer-CO—OR+$H_2N$-Photo-initiator→Polymer-CO—NH-Photo-initiator+HO—R (transamidation)

Polymer-O—COR+HOOC-Photo-initiator→Polymer-O—CO-Photo-initiator+HOOC—R (acidolysis)

"Polymer-CO—OR" may be e.g. poly[alkyl (meth)acrylate], poly(alkyl crotonate), poly(alkyl tiglate), poly(dialkyl maleate), poly(dialkyl fumarate), and poly(dialkyl itaconate). "Polymer-O—COR" may be e.g. poly(vinyl acetate). "HO-Photo-initiator" may be e.g. Irgacure 2959, 2- or 4-hydroxybenzophenone, N-(2-hydroxyethyl)-2-benzoylbenzamide, and N-(2-hydroxyethyl)-4-benzoylbenzamide. "$H_2N$-Photo-initiator" may be e.g. N-(2-aminoethyl)-2-benzoylbenzamide and N-(2-aminoethyl)-4-benzoylbenzamide. "HOOC-Photo-initiator" may be e.g. 2- or 4-benzoylbenzoic acid and Irgacure 2959 acid.

Several radical polymerized monoblock, diblock and triblock copolymers are suitable as thermoplastic matrix polymers and hydrophilic polymers (see above). Each hydrophobic block in those diblock and triblock copolymers [e.g. homo- and copolymers of styrenes, such as styrene, α-methylstyrene, vinyltoluene, vinylpyridine, ethylstyrene, tert-butylstyrene, isopropylstyrene, dimethylstyrene, and other alkylated styrenes; (meth)acrylic esters, such as methyl acrylate, ethyl acrylate, propyl acrylate, n-butyl acrylate, isobutyl acrylate, 2-ethylhexyl acrylate, tert-butyl acrylate, methyl methacrylate, ethyl methacrylate, n-butyl methacrylate, and isobutyl methacrylate; butadiene; chloroprene; vinyl halides, such as vinyl chloride; vinyl nitriles, such as acrylonitrile and methacrylonitrile; vinyl esters, such as vinyl acetate, vinyl versatate and vinyl propionate; ethylene; propylene; 1-butene; and isobutylene] and each hydrophilic block [e.g. homo- and copolymers of N-vinylpyrrolidone; (meth)acrylic acid; maleic acid; fumaric acid; crotonic acid; tiglic acid; itaconic acid; monoalkyl esters of dicarboxylic acids; (meth)acrylamide; N-methylol(meth)acrylamide, and other N-alkylacrylamides; N,N-dialkyl(meth)acrylamides, such as N,N-dimethyl(meth)acrylamide; salts and acidic forms of S-vinylsulphonic acid, vinylbenzenesulphonic acid, 2-acrylamido-2-methylpropanesulphonic acid (AMPS), 2-sulphoethyl methacrylate, and P-vinylphosphonic acid; amides of vinylamine, such as N-vinylformamide or N-vinylacetamide; vinylpyridine; vinylimidazole; aminoalkyl (meth)acrylates, such as dimethylaminoethyl (meth)acrylate and di-tert-butylaminoethyl (meth)acrylate; and N,N-dimethyl-N-methacryloyloxyethyl-N-(3-sulphopropyl) ammonium betaine (SPE)] may suitably be copolymerized with a small amount of a radical polymerizable photo-initiator in such a way that the photo-initiator is left unchanged during radical polymerization. Such radical polymerizable photo-initiators include esters or amides of an alcohol or amine derivative of a photo-initiator (such as a Norrish type I photo-initiator like Irgacure 2959 and/or a hydrogen abstraction photo-initiator like 4-hydroxybenzophenone) with polymerizable electrophiles like (meth)acrylic acid, maleic acid, fumaric acid, itaconic acid, crotonic acid, tiglic acid, N-acryloylglycine (or their derivatives, such as anhydrides and acid chlorides), 2-vinyl-4,4-dimethyl-5-oxazolone, 2-(2-propenyl)-4,4-dimethyl-5-oxazolone, 2-vinyl-4,4-diethyl-5-oxazolone, or 2-vinyl-4,4-tetramethylene-5-oxazolone. Radical polymerizable photo-initiators also include esters or amides of an acid derivative of the photo-initiator (such as Irgacure 2959 acid and/or 2- or 4-benzoylbenzoyl chloride) and an alcohol or amine derivative of a polymerizable acid (such as 2-hydroxyethyl methacrylate or 2-hydroxyethyl acrylate) or with 2-vinyloxazoline or 2-(2-propenyl)oxazoline (which react with the carboxylic acid group to form a radical polymerizable ester).

Benzophenones may be formed in situ by Friedel-Crafts benzoylation of an electron-rich aromatic moiety with benzoyl chloride and a Lewis acid as catalyst, e.g. AlCl$_3$. Aromatic anhydrides, such as phthalic anhydride, pyromellitic dianhydride (1,2,4,5-benzenetetracarboxylic acid dianhydride) and BTDA, are less reactive than benzoyl chloride but may also be used. If the para position of the aromatic moiety is vacant, then the para compound is the main product because of the size of the benzoyl group (see e.g. 3. March: "Advanced Organic Chemistry. Reaction, Mechanisms, and Structure", 3. ed., p. 484-7, Wiley-Interscience, New York, 1985). However, the method may also be used with aromatic moieties which do not have vacant para positions. The aromatic moiety may be part of homo- or copolymers of vinylpyridine, styrene, α-methylstyrene, vinyltoluene, alkoxystyrene, aryloxystyrene, ethylstyrene, tert-butylstyrene, isopropylstyrene, dimethylstyrene, and other alkylated styrenes. Any aromatic diisocyanates or aromatic diols that have been employed in the production of HPEU may also be benzoylated. The aromatic moiety may be present in either the thermoplastic matrix polymer or in the hydrophilic polymer or in both. The aromatic ring of the benzoyl chloride may also itself be substituted; electron donating substituents on the benzoyl chloride will increase the rate of reaction. As an example, with ordinary polystyrene the following reaction occurs:

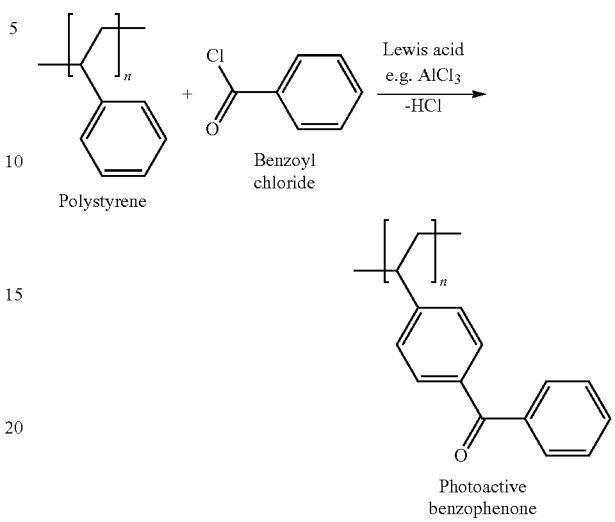

Ethers such as PEO, poly(1,2-propylene oxide), or poly(tetramethylene oxide) may be acyloxylated by reaction with a tert-butyl peroxyester of a carboxyl-containing photo-initiator to give the ether ester and tert-butyl alcohol (see J. March: "Advanced Organic Chemistry. Reaction, Mechanisms, and Structure", 3. ed., p. 636-7, Wiley-Interscience, New York, 1985). The ether may be present in either the thermoplastic matrix polymer or in the hydrophilic polymer or in both. As an example, the coupling with a benzophenone derivative (2-benzoylbenzoyl chloride) is shown here:

The reaction may also be carried out with BTDA or with an acid chloride derivative of a Norrish type I photo-initiator, such as Irgacure 2959 acid chloride.

Ethers such as PEO, poly(1,2-propylene oxide), or poly(tetramethylene oxide) may alkylate (i.e. add to) photo-initiator double bonds in the presence of peroxides to give the corresponding alkylated ethers. The best results are obtained with electron-deficient alkenes such as maleic anhydride (see C. Walling, E. S. Huyser: "Free radical additions to olefins to form carbon-carbon bonds", *Organic Reactions*, 13, 91-149). The ether may be present in either the thermoplastic matrix polymer or in the hydrophilic polymer or in both. A nucleophilic photo-initiator (such as Irgacure 2959) may e.g. acquire an electron-deficient double bond by esterification with maleic anhydride.

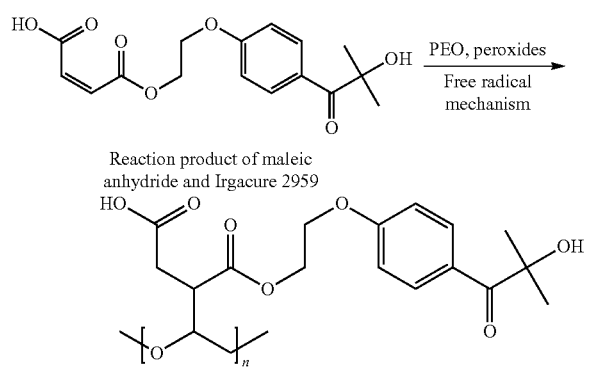

Reaction product of maleic anhydride and Irgacure 2959

PEO forms a strong water-soluble complex with urea (see N. Clinton and P. Matlock: "Ethylene oxide polymers and copolymers", in Encyclopaedia of Polymer Science and Engineering, 2. edition, eds. H. F. Mark, N. M. Bikales, C. G. Overberger, vol. 6, p. 252 (1986)). An electrophilic photo-initiator (such as 2- or 4-benzoylbenzoyl chloride, BTDA or Irgacure 2959 acid chloride) may react with N-(2-hydroxyethyl)urea to form the corresponding photo-initiator ester urea, which will make a strong non-covalent complex with PEO. Alternatively, polyureas terminated with amino groups may react with electrophilic photo-initiators (such as 2- or 4-benzoylbenzoyl chloride or Irgacure 2959 acid chloride) to form the corresponding photo-initiator amide polyureas, which will make a strong non-covalent complex with PEO. Polyureas terminated with isocyanate groups may react with nucleophilic photo-initiators (such as Irgacure 2959) to form the corresponding photo-initiator urethane polyureas, which will make a strong non-covalent complex with PEO.

In a still further embodiment, a plurality of photo-initiator moieties are covalently linked to a low molecular weight scaffold, e.g. the photo-initiators may be covalently linked to a low molecular scaffold, e.g. star-shaped, or a dendrimer.

The term "low molecular weight" refers to a scaffold (without the photo-initiator moieties) having a molecular weight of up to 10 kDa.

In applications where the potential presence of a small amount of residual monomer is not prohibitive, a range of acrylate monomers and oligomers may be added to the coating, e.g. polybutadiene diacrylate (San Esters), Omnilane JL-103M (acrylamidomethyl substituted cellulose ester polymer; from IGM/Bomar), Omnilane BR 3641AA (1.3-functional aliphatic urethane acrylate, adhesion promoter), Omnilane BDE-1029 (14-functional dendritic polyester acrylate blend). Such compounds may cross-link by reaction with radicals from photo-curing, e.g. PVP-centered radicals:

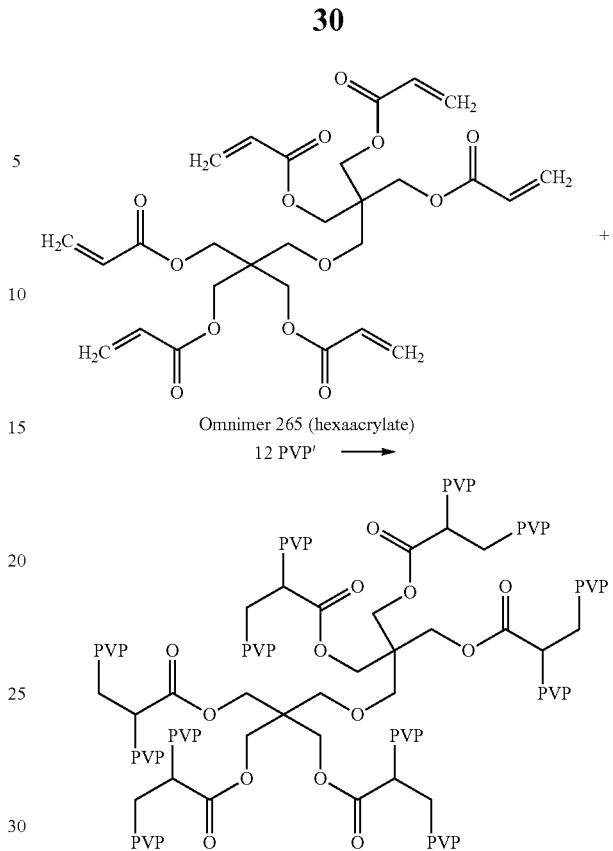

As it will be evident from the description above, the present invention takes advantage of a covalent cross-linking method which does not require cross-linking by means of (meth)acrylate monomers, and the coating composition does therefore in the most interesting embodiments not comprise (meth)acrylic monomers. Residual acrylates may be acutely toxic, genotoxic, carcinogenic, or they may cause allergy, skin rashes, sensitization or, at best, be only locally irritating. Hence systems with residual acrylates or other reactive monomers are best avoided.

Detailed procedure for the preparation of a medical device element

Step (i)

In an initial step of the method, the prefabricated shaped article and/or the thermoplastic substrate polymer are provided.

As it is clear from the section "Thermoplastic substrate polymer", the substrate polymer is typically a commercial product traded in a suitable physical form, e.g. as pellets, chips, granules, etc. Hence, pre-treatment or preparation is normally not necessary.

If a mixture of two or more substrate polymers is used, it is typically desirable to homogenize the polymers, either in a melted form or by dissolving the polymers in a common solvent followed by solvent removal by conventional procedures and involving conventional equipment, such as spray coating, roller drying or precipitation in a non-solvent. Preferably, the solvent solution is cast into a film and the solvent removed from the film by any conventional technique. Reduced pressure and/or elevated temperature may be used to aid solvent removal. The resulting homogeneous blend may be chipped or pelletized prior to melt processing.

It is further clear from the section "Prefabricated shaped article" that the shaped article is often available from commercial sources, or is readily prepared as will be known by the skilled person within the relevant art. Alternatively, but also very interestingly, the shaped article may be prepared immediately prior to its use in the method of the invention, in certain embodiments even in the same process line as the one where the method is applied. Moreover, the prefabricated shaped article may be pre-treated and even pre-coated prior to use in the method of the invention.

Step (ii)

The coating composition for the preparation of the medical device element may be prepared by dissolving the constituents thereof in a common solvent. The solvent may then be removed to leave a homogeneous blend of the matrix polymer, the hydrophilic polymer, the one or more photo-initiators, and any additives, which is ready for extrusion. Any conventional procedure or equipment may be used for solvent removal, such as spray coating, roller drying or precipitation in a non-solvent such as acetone or carbon tetrachloride. Preferably the solvent solution is cast into a film and the solvent removed from the film by any conventional technique. The cast film may then be heated in a convection oven at a temperature from ambient to about 70° C. Reduced pressure may be used to aid solvent removal. The resulting homogeneous blend may be chipped or pelletized prior to melt processing or powder coating.

In another embodiment, one or more of the matrix polymer and the hydrophilic polymer, preferably the matrix polymer, is/are in-situ polymerized in the formation of the coating, i.e. either in step (iii) or in step (iv).

Typically, a mix of monomers or prepolymers corresponding to the matrix polymer or the hydrophilic polymer or both are mixed with the other constituents of the coating composition. The homogeneous mixture of the monomers or the prepolymers is typically heated and reacted to completion (e.g. 99-100% conversion). The reaction of the monomers or the prepolymers can take place in a continuous process such as in a twin-screw extruder or similar. The reaction may also be carried out as a batch process with or without stirring. The mixture or resulting homogeneous blend may after a cooling step be chipped or pelletized prior to melt processing or powder coating.

This pelletized coating composition may subsequently be extruded, injection moulded or powder coated on the pre-fabricated shaped article or the thermoplastic substrate polymer as described for step (iii) below.

In one embodiment, monomers or pre-polymers corresponding to the matrix polymer are mixed with the other constituents of the coating composition.

For example, a mixture containing an organic isocyanate, low molecular weight polyethylene glycols, chain extenders and a suitable amount of catalysts is mixed with a hydrophilic polymer, one or more photo-initiators and other additives.

The organic diisocyanate reactant may be any aliphatic, alicyclic, aliphatic-alicyclic, aromatic or aliphatic-aromatic compound consisting of 4 to 26 carbon atoms, more usually 6 to 20 carbon atoms and preferably 8 to 15 carbon atoms. Representative diisocyanates are tetramethylene diisocyanate, hexamethylene diisocyanate, trimethylhexamethylene diisocyanate, dimer acid diisocyanate, isophorone diisocyanate, diethylbenzene diisocyanate, decamethylene-1,10-diisocyanate, cyclohexylene-1,2-diisocyanate, cyclohexylene 1,4-diisocyanate and methylenebis(cyclohexyl-4-isocyanate); and aromatic isocyanates such as 2,4- and 2,6-tolylene diisocyanate, 4,4-diphenylmethane diisocyanate, 1,5-naphthalene diisocyanate, dianisidine diisocyanate, toluidine diisocyanate, xylylene diisocyanate, and tetrahydronapthalene-1,5-diisocyanate.

The poly(oxyalkylene) glycols are typically derived from $C_2$-$C_4$ alkylene oxides such as oxyethylene, oxytrimethylene, propylene glycol, oxybutylene, oxyisobutylene, butylene glycol and oxytetramethylene (or the blend of poly (tetraoxymethylene) and other polyether glycols) and further include random or block copolymer polyols obtained by adding ethylene oxide to 1,2-propylene oxide or by adding ethylene oxide to a poly(oxypropylene) chain. Furthermore the hydrophilic polyols may also be branched or introduce branching such as in Tegomer® D 3403.

Chain extender examples include diols such as ethylene glycol, diethylene glycol, triethylene glycol, 1,4-butanediol, hexamethylene glycol, thiodiglycol, 2,2-dimethylpropane-1, 3-diol, 1,4-bis(hydroxymethyl)benzene, bis(hydroxyethyl) disulphide, cyclohexanedimethanol and hydroquinone; diamines such as ethylenediamine, hexamethylenediamine and 1,4-butane diamine; dihydrazides such as carbodithydrazide, oxalic hydrazide, hydrazine and substituted hydrazines. The preferred chain extenders are ethylene glycol, diethylene glycol and other alkylene glycols of 2 to 6 carbon atoms.

Suitable catalysts include tin salts and organotin esters such as stannous octoate and dibutyl tin dilaurate, tertiary amines such as triethylene diamine (DABCO™), N,N,N', N'-tetramethyl-1,3-butanediamine and other recognized catalysts for urethane reactions.

In one particular embodiment the photo-initiator may contain functional groups such as hydroxyl, carboxyl or amine groups either as mono, di or multifunctional and may be polymerized into the matrix polymer. Monofunctional photo-initiators will terminate the polymerization of polyurethanes and give end-functional polyurethanes. Continuous polymerization processes will be of particular interest, such as polymerization in a twin-screw extruder or similar continuous processes.

The advantages of in-situ polymerization are that several process steps such as drying, compounding, pelletizing and hence some types of characterization are avoided. Furthermore the material is ideally mixed and the degradation is diminished because the pelletized coating composition can be used directly without any further treatment.

One example of in-situ polymerization of the matrix polymer in the formation of the coating will be described in more detail in the following.

Since PVP does not react with any of the components used to prepare an HPEU, a coating composition comprising PVP and a hydrophilic polyetherurethane may be prepared by adding the PVP to the recipe for HPEU synthesis. Alternatively, the components of the composition may be blended by melt compounding, such as in a Brabender mixer, or with a single or twin screw extruder. In such an instance, the HPEU and PVP are mixed in a suitable solvent wherein the ratio of HPEU to PVP may be from 99:1 to 30:70 by weight. The preferred ratio is about 50:50 by weight. Suitable solvents are DMSO, DMF, DMAC and NMP. These high boiling solvents may be used alone but are preferably mixed with a low boiling solvent such as THF, methylene chloride or methyl ethyl ketone. Most preferably, a solvent mixture containing a 3:2 ratio of DMAC to THF is used. The composition may be about 1% to 20%, preferably about 4 to 12% by weight in the solvent. It is evident that, if the HPEU is prepared by emulsion polymerization as described above, water may serve as the solvent and the PVP merely added thereto.

Photo-initiators, either with low molecular weights, oligomeric, polymeric or with functional groups can be blended and eventually during the hot melt blending be grafted by chemically bonding onto the thermoplastic matrix polymers.

Step (iii)

This step involves extruding, injection moulding or powder coating the coating composition of step (ii) on the prefabricated shaped article or together with the thermoplastic substrate polymer of step (i) so as to provide the medical device element of said prefabricated shaped article and/or substrate polymer having thereon a layer of said coating composition, wherein, when both of said prefabricated shaped article and substrate polymer are present, said prefabricated shaped article has thereon a layer of said substrate polymer.

Three main embodiments are encompassed by this step.

In a first main embodiment, only a prefabricated shaped article is provided in step (i), and step (iii) involves extruding, injection moulding or powder coating the coating composition of step (ii) on the prefabricated shaped article of step (i) so as to provide the medical device element of said prefabricated shaped article having thereon a layer of said coating composition.

In a second main embodiment, only a thermoplastic substrate polymer is provided in step (i), and step (iii) involves extruding or injection moulding the coating composition of step (ii) together with the thermoplastic substrate polymer of step (i) so as to provide the medical device element of said thermoplastic substrate polymer having thereon a layer of said coating composition.

In a third main embodiment, a prefabricated shaped article as well as a thermoplastic substrate polymer are provided in step (i), wherein step (iii) involves extruding or injection moulding the coating composition of step (ii) on the prefabricated shaped article together with the thermoplastic substrate polymer of step (i) so as to provide the medical device element of said prefabricated shaped article and said thermoplastic substrate polymer, said prefabricated shaped article having thereon a layer of said thermoplastic substrate polymer and said thermoplastic substrate polymer having thereon a layer of said coating composition.

The three main embodiments will be discussed in the following.

In a first variant of the first main embodiment, a melt of the coating composition is extruded onto a surface of a prefabricated shaped article (see, e.g., Example 5).

In a second variant of the first main embodiment, a melt of the coating composition is injection moulded onto a surface of a prefabricated shaped article.

In a third variant of the first main embodiment, the coating composition is powder coated onto a surface of a prefabricated shaped article.

In one variant of the second main embodiment, a melt of the thermoplastic substrate polymer and a melt of the coating composition are extruded to give a shaped article having a coating of the coating composition on the surface of the substrate polymer.

In another variant of the second main embodiment, a melt of the thermoplastic substrate polymer and a melt of the coating composition are injection moulded to give a shaped article having a coating of the coating composition on the surface of the substrate polymer. This interesting variant can be accomplished in a two step injection moulding process wherein in the outer layer of the coating composition is first moulded followed by the moulding of the thermoplastic substrate polymer.

In one variant of the third main embodiment, a melt of the substrate polymer and a melt of the coating composition are extruded onto a surface of a prefabricated shaped article (see, e.g., Example 5).

In another variant of the third main embodiment, a melt of the substrate polymer and a melt of the coating composition are injection moulded onto a surface of a prefabricated shaped article. This interesting variant can be accomplished in a two step injection moulding process wherein in the outer layer of the coating composition is first moulded using a solid core followed by the moulding of the thermoplastic substrate polymer using the prefabricated shaped article as the core.

The coating composition may be extruded/co-extruded with the substrate polymer using any conventional and commercially available extrusion equipment. Suitable co-extrusion apparatus may be purchased, for example, from Genca Cable Company, Clearwater, Fla., or from Wayne Machine and Die Company, Totowa, N.J., or, if desired, custom co-extrusion apparatus can be designed for fabrication of any specific medical device element.

Alternatively, the composition may be crosshead-extruded or co-extruded onto a prefabricated shape article, e.g. polymeric article. Extrusion of a skin layer is a conventional process in which a melt of a thermoplastic material (here the thermoplastic substrate polymer or the coating composition) is metered through a die directly onto a solid, continuous, shaped surface.

Moreover, (co)extrusion and injection moulding may be conducted as described in U.S. Pat. Nos. 5,061,424 and 6,447,835.

The coating composition may also injection moulded so as to provide a coating on a thermoplastic substrate polymer or prefabricated shaped article. The injection moulding variants may one or two process steps. In one variant corresponding to the second variant of the first main embodiment (see above), the coating composition is injected at high pressure into a mould, which is the inverse of the shape of the final product, using a solid core of the prefabricated shaped article. In a second variant (corresponding to the second variant of the second main embodiment (see above), step (iii) can be accomplished in two sub-steps, namely by first moulding the coating composition using a solid core, removing the solid core, and subsequently moulding the thermoplastic substrate polymer, optionally using a slightly smaller solid core. In a third variant (corresponding to the second variant of the third main embodiment (see above), step (iii) can be accomplished in two sub-steps, namely by first moulding the coating composition using a solid core, removing the solid core, and subsequently moulding the thermoplastic substrate polymer, using the prefabricated solid article as the solid core. In a fourth variant (corresponding to the second variant of the second main embodiment (see above), step (iii) can be accomplished in two sub-steps, namely by first moulding the thermoplastic substrate polymer using a cavity of one size, removing the cavity, and subsequently moulding the coating composition onto the thermoplastic substrate polymer using a slightly larger cavity. In a fifth variant (corresponding to the second variant of the third main embodiment (see above), can be accomplished in two sub-steps, namely by first moulding the thermoplastic substrate polymer using a cavity of one size and the prefabricated shaped article as the core, removing the cavity, and subsequently moulding the coating composition onto the thermoplastic substrate polymer using a slightly larger cavity.

With regard to powder coating which generally follows conventional principles, the pelletized compound containing hydrophilic polymers, photo-initiators and the thermoplastic matrix polymers can be milled to a particle size in the range of 5 to 250 micrometers. Usually a powder coating composition with a particle size distribution in the range of 10 to 100 micrometers is preferred.

The powder coating compositions are typically applied by spraying or by the use of a fluidized bed system. In case of a metal substrate (prefabricated shaped article), application of the coating by electrostatic spraying is preferred. In case of spraying the powder coating can be applied in a single sweep or in several passes to provide a film having the preferred thickness.

After applying the powder by spraying or by using a fluidized bed system or any other powder coating application technology known in the industry, the thermoplastic powder is heated to about 80 to 200° C., depending on the type of substrate, to form a uniform coating layer about 5 to 250 micrometers thick, usually about 10 to 100 micrometers thick.

Within the various embodiments of the invention, the thermoplastic matrix polymers in the compound may be either polymerized "in situ" with polymerizable photo-initiators, or the thermoplastic matrix polymers may be modified with photo-initiators after polymerisation, so as to obtain covalent bonding between the polymers and the photo-initiators. The hydrophilic polymers may also contain photoactive groups, either by copolymerization of hydrophilic monomers with monomers containing photo-initiators, or the photoactive group may be covalently bound by a chemical reaction between the hydrophilic polymers and the photo-initiators.

The thickness of the dry layer of the coating composition is typically 2.5-500 µm, preferably 2.5-125 µm.

The thickness of the substrate polymer (if present) is typically 5-1000 µm, more typically 10-50 µm or 100-500 µm.

The medical device element obtained by the method is dry and in general non-sticky until humidified by finger-touch or wetted with a liquid, at which time it develops a slippery, lubricious surface. The chains of the hydrophilic polymer (e.g. PVP) are believed to be substantially trapped in the matrix polymer both by means of physical entrapment and by covalent bonding.

The method of the invention is particularly useful for the preparation of medical device elements having the shape of a rod or tubing. For example, a catheter thus prepared becomes instantly lubricious when it comes into contact with a water-containing fluid and thereby contributes greatly to the comfort of a patient undergoing catheterization. An extruded rod in the form of a guide-wire becomes lubricious when wet and thus slides easily.

After extrusion or injection moulding, it may be necessary to cool the medical device element, e.g. by cold air or in a water bath.

This being said, the currently most preferred embodiments of the step (iii) are those involving (co)extrusion.
Step (iv)

In a subsequent step, the coating composition is irradiated with UV or visible light so as to covalently cross-link the coating composition. UV or visible light is defined as light having a wavelength of 100-750 nm. Particularly relevant wavelength ranges are 100-250 nm and 250-400 nm (both UV light), and 400-750 nm (visible light). In the present context, the terms "photo-curing", "photo-cure" and the like refer to curing by means of UV or visible light. Curing by means of UV light is preferred, although curing by means of blue light (visible light wavelength range) is equally applicable.

The UV or visible light may be applied by means of a polychromatic or monochromatic UV or visible light source, preferably with high intensity and with an emission spectrum that matches the absorbance spectrum of the photo-initiator(s) as well as possible. In the absence of reactive monomers, the cross-linking of the coating takes place only by the bimolecular combination of radicals derived from the UV (or visible light) irradiated photo-initiators. Hence, if the light intensity is doubled, the concentration of radicals is also doubled, but the amount of cross-linking reactions is quadrupled. This is why a high light intensity is preferred. Suitable polychromatic light sources include: (i) deuterium lamps, (ii) mercury lamps, possibly doped with iron, gallium or other elements that significantly affects the output spectrum, (iii) xenon arc lamps, both pulsed and unpulsed, and (iv) halogen lamps (emit mainly visible light). Suitable monochromatic light sources include: (v) gas and solid state lasers (possibly frequency doubled, tripled, quadrupled or in other ways frequency manipulated), both pulsed and unpulsed, and (vi) light emitting diodes in the UV and visible area, both pulsed and unpulsed.

An optimal irradiation period and light intensity can easily be found by the skilled person by routine experiments, e.g. as described in Example 6. For practical reasons (e.g. in the large scale production of the medical device), the irradiation period should preferably not exceed 300 sec, and in particular should not exceed 600 sec.

Currently most preferred embodiments of the method of the present invention include:

I. A method for the preparation of a medical device element, said method comprising the steps of:
(i) providing a thermoplastic substrate polymer;
(ii) providing a coating composition comprising a thermoplastic matrix polymer selected from hydrophilic polyurethane polymers and amphiphilic block-copolymers, a hydrophilic polymer selected from polyethylene oxide, and two or more different photo-initiators;
(iii) co-extruding the coating composition of step (ii) and the thermoplastic substrate polymer of step (i) so as to provide the medical device element of said substrate polymer having thereon a layer of said coating composition;
(iv) irradiating the coating composition with UV or visible light so as to covalently cross-link said coating composition.

II. A method for the preparation of a medical device element, said method comprising the steps of:
(i) providing a thermoplastic substrate polymer;
(ii) providing a coating composition comprising a thermoplastic matrix polymer selected from hydrophilic polyurethane polymers and amphiphilic block-copolymers, a hydrophilic polymer selected from polyethylene oxide, and one or more photo-initiator(s) covalently linked to a polymer or a scaffold;
(iii) co-extruding the coating composition of step (ii) and the thermoplastic substrate polymer of step (i) so as to provide the medical device element of said substrate polymer having thereon a layer of said coating composition;
(iv) irradiating the coating composition with UV or visible light so as to covalently cross-link said coating composition.

III. A method for the preparation of a medical device element, said method comprising the steps of:
(i) providing a prefabricated shaped article and optionally a thermoplastic substrate polymer;
(ii) providing a coating composition comprising a thermoplastic matrix polymer selected from hydrophilic polyurethane polymers and amphiphilic block-copolymers, a hydrophilic polymer selected from polyethylene oxide, and two or more different photo-initiator(s);
(iii) co-extruding the coating composition of step (ii) on the prefabricated shaped article and, if present, the thermoplastic substrate polymer of step (i) so as to provide the medical device element of said prefabricated shaped article and, if present, said substrate polymer having thereon a layer of said coating composition, wherein, when said substrate polymer is present, said prefabricated shaped article has thereon a layer of said substrate polymer;
(iv) irradiating the coating composition with UV or visible light so as to covalently cross-link said coating composition.
IV. A method for the preparation of a medical device element, said method comprising the steps of:
(i) providing a prefabricated shaped article and optionally a thermoplastic substrate polymer;
(ii) providing a coating composition comprising a thermoplastic matrix polymer selected from hydrophilic polyurethane polymers and amphiphilic block-copolymers, a hydrophilic polymer selected from polyethylene oxide, and one or more photo-initiator(s) covalently linked to a polymer or a scaffold;
(iii) co-extruding the coating composition of step (ii) on the prefabricated shaped article and, if present, the thermoplastic substrate polymer of step (i) so as to provide the medical device element of said prefabricated shaped article and, if present, said substrate polymer having thereon a layer of said coating composition, wherein, when said substrate polymer is present, said prefabricated shaped article has thereon a layer of said substrate polymer;
(iv) irradiating the coating composition with UV or visible light so as to covalently cross-link said coating composition.
V. A method for the preparation of a medical device element, said method comprising the steps of:
(i) providing a thermoplastic substrate polymer;
(ii) providing a coating composition comprising a thermoplastic matrix polymer selected from hydrophilic polyurethane polymers and amphiphilic block-copolymers, a hydrophilic polymer selected from polyethylene oxide, and one or more different photo-initiator(s), e.g. two or more different photo-initiators, where such photo-initiator(s) may be covalently linked to a polymer or to a scaffold;
(iii) injection moulding the coating composition of step (ii) and the thermoplastic substrate polymer of step (i) so as to provide the medical device element of said substrate polymer having thereon a layer of said coating composition;
(iv) irradiating the coating composition with UV or visible light so as to covalently cross-link said coating composition.
VI. A method for the preparation of a medical device element, said method comprising the steps of:
(i) providing a prefabricated shaped article and optionally a thermoplastic substrate polymer;
(ii) providing a coating composition comprising a thermoplastic matrix polymer selected from hydrophilic polyurethane polymers and amphiphilic block-copolymers, a hydrophilic polymer selected from polyethylene oxide, and one or more different photo-initiator(s), e.g. two or more different photo-initiators, where such photo-initiator(s) may be covalently linked to a polymer or to a scaffold;
(iii) injection moulding the coating composition of step (ii) on the prefabricated shaped article and, if present, the thermoplastic substrate polymer of step (i) so as to provide the medical device element of said prefabricated shaped article and, if present, said substrate polymer having thereon a layer of said coating composition, wherein, when said substrate polymer is present, said prefabricated shaped article has thereon a layer of said substrate polymer;
(iv) irradiating the coating composition with UV or visible light so as to covalently cross-link said coating composition.

Novel Medical Devices

It is believed that the medical device elements resulting from the method described above represent products which are novel per se.

Hence, the present invention also relates to novel medical devices comprising a medical device element of a thermoplastic substrate polymer having thereon a layer of a covalently cross-linked coating composition of (a) a thermoplastic matrix polymer and (b) a hydrophilic polymer; wherein said coating composition is (co)extruded or injection moulded with said thermoplastic substrate polymer, or said coating composition is powder coated on said thermoplastic substrate polymer; and wherein the covalent cross-linking of the coating composition is the result of the presence of one or more photo-initiators in the coating composition and the exposure of the coating composition to UV or visible light.

The present invention further relates to novel medical devices comprising a medical device element of a prefabricated shaped article having thereon a layer of a covalently cross-linked coating composition of (a) a thermoplastic matrix polymer and (b) a hydrophilic polymer; wherein said coating composition is extruded, injection moulded or powder coated on said prefabricated shaped article; and wherein the covalent cross-linking of the coating composition is the result of the presence of one or more photo-initiators in the coating composition and the exposure of the coating composition to UV or visible light.

The present invention still further relates to novel medical devices comprising a medical device element of a prefabricated shaped article having thereon a layer of a thermoplastic substrate polymer, where said thermoplastic substrate polymer has thereon a layer of a covalently cross-linked coating composition of (a) a thermoplastic matrix polymer and (b) a hydrophilic polymer; wherein said coating composition is (co)extruded, injection moulded or powder coated on said prefabricated shaped article and said thermoplastic substrate polymer; and wherein the covalent cross-linking of the coating composition is the result of the presence of one or more photo-initiators in the coating composition and the exposure of the coating composition to UV or visible light.

In interesting embodiments of the above, said one or more photo-initiators are covalently linked to molecules of the thermoplastic matrix polymer and/or to molecules of the hydrophilic polymer.

Following the discussion further above, the coating composition does not comprise low-molecular weight residues of (meth)acrylic monomers.

The materials useful as the prefabricated shaped article, the thermoplastic substrate polymer and as constituents of the coating compositions are as described above for the method of the invention.

Hence, in one embodiment, the thermoplastic substrate polymer is selected from the group consisting of polyurethanes, and PVC.

In a further embodiment, the thermoplastic matrix polymer is a polyurethane polymer, in particular a hydrophilic polyurethane polymer.

In a still further embodiment, the hydrophilic polymer is selected from the group consisting of poly(vinyl lactams) [e.g. PVP], PEO, polyoxazolines, PVOH, and polyacrylates. The currently most preferred hydrophilic polymer is PEO.

EXAMPLES

| Trade name/trivial name/abbreviation | Chemical name |
|---|---|
| | Abbreviations |
| 2-BBCl | 2-Benzoylbenzoyl chloride |
| BDO | 1,4-Butanediol |
| BTDA | 3,3',4,4'-Benzophenonetetracarboxylic acid dianhydride |
| Chivacure 3482 | 2-Methyl-1-[4-(alkylthio)phenyl]-2-(4-morpholinyl)-1-propanone (alkyl chain not revealed) |
| Chivacure 3690 | 2-Benzyl-2-(dimethylamino)-1-[4-(alkylmethylamino)phenyl]-1-butanone (alkyl chain not revealed) |
| CMC | Carboxymethylcellulose |
| Darocur 1173 | 2-Hydroxy-2-methylpropiophenone; 2-hydroxy-2-propyl phenyl ketone |
| Darocur TPO | Diphenyl(2,4,6-trimethylbenzoyl) phosphine oxide |
| DMAC | N,N-Dimethylacetamide |
| DMAEMA | N,N-Dimethylaminoethyl methacrylate |
| DMF | N,N-Dimethylformamide |
| DMSO | Dimethylsulfoxide |
| EEA | Copoly(ethylene/ethyl acrylate) |
| EMA | Copoly(ethylene/methyl acrylate) |
| EnBA | Copoly(ethylene/n-butyl acrylate) |
| EO | Ethylene oxide |
| Esacure KIP 150 | Oligo{2-hydroxy-2-methyl-1-[4-(1-methylvinyl)phenyl]propanone} |
| Esacure One | "Difunctional α-hydroxy ketone" (structure not revealed) |
| EVA | Copoly(ethylene/vinyl acetate) |
| EVA g-MAH | Copoly(ethylene/vinyl acetate)-graft-poly(maleic anhydride) |
| EVOH | Copoly(ethylene/vinyl alcohol) |
| GMA | Glycidyl methacrylate (2,3-epoxypropyl methacrylate) |
| HPEU | Hydrophilic polyetherurethane |
| Irgacure 127 | Bis(4-(2-hydroxy-2-propylcarbonyl)phenyl)methane |
| Irgacure 184 | 1-Hydroxy-1-cyclohexyl phenyl ketone |
| Irgacure 2959 | 2-Hydroxy-2-propyl 4-(hydroxyethoxy)phenyl ketone |
| Irgacure 369 | 2-Benzyl-2-(dimethylamino)-1-[4-(4-morpholinyl)phenyl]-1-butanone |
| Irgacure 379 | 2-(4-Methylbenzyl)-2-(dimethylamino)-1-[4-(4-morpholinyl)phenyl]-1-butanone |
| Irgacure 651 | Benzil α,α-dimethyl ketal; α,α-dimethoxy-α-phenylacetophenone; 2,2-dimethoxy-1,2-diphenyl-1-ethanone |
| Irgacure 819 | Phenylbis(2,4,6-trimethylbenzoyl) phosphine oxide |
| Irgacure 907 | 2-Methyl-1-[4-(methylthio)phenyl]-2-(4-morpholinyl)-1-propanone |
| LDPE | Low density polyethylene |
| LLDPE | Linear low density polyethylene |
| MAH | Maleic anhydride |
| MDI | Methylene-4,4'-diphenyldiisocyanate |
| NMP | N-Methylpyrrolidone |
| NVP | N-Vinyl pyrrolidone |
| Omnilane XP-144 LS-B | "Medium molecular weight, trifunctional, aliphatic polyether urethane acrylate oligomer with backbone-grafted photo-initiator" (photo-initiator not revealed but may be benzoin[§]) |
| Omnipol BP | Poly(tetramethylene glycol) 250 diester of 4-benzoylphenoxyacetic acid |
| Omnipol TX | Poly(tetramethylene glycol) 250 diester of 2-thioxanthonyloxyacetic acid |
| PE | Polyethylene |
| PE g-MAH | Polyethylene-graft-poly(maleic anhydride) |
| Pebax | Polyether-block-polyamide |
| PEG | Poly(ethylene glycol) |
| PEO | Poly(ethylene oxide) |
| PMDA | Pyromellitic acid dianhydride; 1,2,4,5-benzenetetracarboxylic acid dianhydride |
| PO | 1,2-Propylene oxide |
| PP | Polypropylene |
| PS | Polystyrene |
| PVC | Poly(vinyl chloride) |
| PVOH | Poly(vinyl alcohol) |
| PVP | Poly(vinyl pyrrolidone) |
| PVP-DMAEMA | Copoly(vinyl pyrrolidone/N,N-dimethylaminoethyl methacrylate) |
| SBS | Polystyrene-block-polybutadiene-block-polystyrene |
| SEBS | Polystyrene-block-poly(ethylene/butylene)-block-polystyrene |
| SEEPS | Polystyrene-block-hydrogenated poly(isoprene/butadiene)-block-polystyrene |
| SEPS | Polystyrene-block-poly(ethylene/propylene)-block-polystyrene |
| SIS | Polystyrene-block-polyisoprene-block-polystyrene |
| SMA | Poly(styrene-co-maleic anhydride) |
| THF | Tetrahydrofuran |
| VLDPE | Very low density polyethylene |

[§]See J. A. Leon, I. V. Khudyakov from Bomar Specialties, USA (2005): "UV-Light Sensitive (LSR) Urethane Acrylate Oligomers", Proceedings from RadTech Europe 05, Barcelona, Spain, Oct. 18-20, 2005, vol. 2, p. 359-64, Vincentz.

Materials

The hydrophilic polyurethane Tecogel 2000 (lots CD53RA015 and PM-03-36D with a water absorption of 500% and 1800%, respectively) were from Noveon; unless otherwise stated lot CD53RA015 was used. The hydrophilic polyurethane Tecogel 500 and the hydrophobic polyurethane Estane 58212 were also from Noveon. The phenoxy resins PKHB (M, 9.5 kDa), PKHH (M, 16 kDa), and PKCP80 (phenoxyresin modified with caprolactone; $M_w$ 39 kDa) were from InChem. Corp.

The PEO's WSR N-80 (MW 200 kDa) and N-301 (MW 4 MDa) were from Dow. MPEG 350 and PEG 400 was from Clariant. PVP K-25 and PVP K-90 were from ISP Corp. (Wayne, N.J.). PEG 35000 ("Polyglykol Hoechst 35000 Schuppen", batch E06389543; MW 35 kDa) was from Hoechst.

The photo-initiator Esacure KIP 150 was from Lamberti Spa (Gallarate, Italy). The photo-initiators Irgacure 127, Irgacure 651, and Irgacure 2959 were from Ciba Specialty Chemicals (Basel, Switzerland). 97% BTDA was from Alfa Aesar. 4-Benzoylbenzoic acid, 2-benzoylbenzoic acid and tert-butyl peroxybenzoate were from Aldrich. CuCl was from Fluka.

Gantrez AN 119 BF (polyanhydride, reactive) and Gantrez ES 225 (alcoholyzed polyanhydride, non-reactive) were from ISP. PMDA (pyromellitic acid dianhydride; 1,2,4,5-benzenetetracarboxylic acid dianhydride) was from Aldrich. SMA 1000 (acid no. 465-495 mg KOH/g sample, MW 5500 g/mol), SMA 2000 (acid no. 335-375 mg KOH/g sample, MW 7500 g/mol), and SMA 3000 (acid no. 265-305 mg KOH/g sample, MW 9500 g/mol) were from Atofina. Joncryl 804 was from BASF.

1-Methylimidazole and pyridine were from Merck. Ethyl acetate, 2-propanol and acetone were from Bie & Berntsen (Denmark). DMSO and thionyl chloride were from Aldrich. Benzene was from Fluka. MIBK was from Baker. Acetic acid was from Merck. Dichloromethane was from Appli-Chem. Jeffamine D-230 was from Huntsman.

All percentages and parts given are weight/weight-% unless otherwise stated.

Example 1

Preparation 60 parts Tecogel 2000 and 40 parts Polyox N-80 were compounded together in a Brabender compounder at 120° C. for 10 minutes. During the last 5 minutes 0-1 part Esacure KIP 150 (see the table below) was added to the blend. After compounding, the blends were hot melt pressed at 120° C. for 20 seconds into thin sheets with a thickness of 150-200 µm. The sheets were hot press laminated at 120° C. for 90 seconds onto substrates of the polyurethane Tecogel 500, which is less hydrophilic than Tecogel 2000. The laminates were UV cured for 4 minutes with a UVASPOT 400/T F-lamp (450 W; arc about 1 inch long; substrate placed about 26 cm from the bulb; Dr. K. Honle GmbH UV-Technologie, Planegg b. München, Germany) at a temperature of approximately 65° C. where the blends were limpid and hence transparent to the UV light.

Results and Discussion

The friction and the adhesion to the substrate were evaluated subjectively after swelling in water for at least 24 hours. The adhesion between the two layers (coating and substrate) was given a score from 1 to 4:
1. Complete delamination
2. Poor adhesion, a lot of water blisters
3. Good adhesion, few water blisters
4. Very good adhesion, smooth surface

| % Esacure KIP 150 | Score of UV cured preparation | Score of not UV cured preparation |
|---|---|---|
| 0.0 | 2 | 2 |
| 0.1 | 2 | 2 |
| 0.5 | 4 | 2 |
| 1.0 | 3 | 2 |

The adhesion between the two layers increased upon UV curing with a photo-initiator concentration above 0.1%. A few blisters were observed at 1.0% photo-initiator. This insufficient curing at the interface between the two layers could be caused by the high concentration and the pronounced absorption of the UV light at the top of the layer, i.e. at the surface. The friction was also lower for the UV cured layers containing the photo-initiator (data not shown). The UV cross-linking of the water-soluble Polyox N-80 bound it to the polyurethane and prevented it from dissolving and from being washed out, i.e. the friction could be maintained for a longer period of time.

Example 2

Preparation

Tecogel 2000 was hot melt compounded with different concentrations of Polyox N-80. The blends contained 1% of Esacure KIP 150. The preparation of the samples and the UV curing were as described in Example 1. The blends were laminated onto substrates of Tecogel 500 or Estane 58212.

Results and Discussion

The adhesion to the substrate was evaluated subjectively after swelling in water for at least 24 hours.

| w/w-ratio Polyox N-80: Tecogel 2000 | Tecogel 500 UV cured | Tecogel 500 Not UV cured | Estane 58212 UV cured | Estane 58212 Not UV cured |
|---|---|---|---|---|
| 20:80 | 4 | 2 | 2 | 1 |
| 40:60 | 4 | 2 | 2 | 1 |
| 60:40 | 4 | 1 | 1 | 1 |
| 80:20 | 4 | 1 | 1 | 1 |

The adhesion to Tecogel 500 was greatly improved by UV curing and was unaffected by the concentration of Polyox N-80. The adhesion to Estane 58212 did not improve with UV curing, since Tecogel 2000 and Estane 58212 were not compatible and all the samples either delaminated or had blisters.

Example 3

Preparation 59.5% Tecogel 2000, 40% Polyox N-80, and 0.5% Esacure KIP 150 were hot melt compounded. The preparation of the samples and the UV curing were as described in Example 1.

The blend was laminated onto different substrates. The substrates were primarily based on Estane 58212 but different types and amounts of phenoxy resins were added as compatibilizers, cf. the table below.

Results and Discussion

The adhesion to the substrate was evaluated subjectively after swelling in water for at least 24 hours.

| Substrate | UV cured | Not UV cured |
|---|---|---|
| Estane 58212 | 1 | 1 |
| Phenoxy resin, PKHB | 3 | 1 |
| Phenoxy resin, PKHH | 4 | 1 |
| Phenoxy resin, PKCP80 | 3 | 1 |
| 90% Estane 58212 + 10% PKHB | 3 | 1 |
| 60% Estane 58212 + 40% PKHB | 4 | 1 |
| 90% Estane 58212 + 10% PKHH | 3 | 1 |
| 60% Estane 58212 + 40% PKHH | 4 | 1 |
| 90% Estane 58212 + 10% PKCP80 | 4 | 1 |
| 60% Estane 58212 + 40% PKCP80 | 4 | 1 |

The addition of a phenoxy resin compatibilizer to the polyurethane Estane 58212 made it possible to UV bond the Tecogel 2000 blend to the substrates, but without UV curing, good adhesion was not obtained.

Example 4

Preparation 59.5% Tecogel 2000 was hot melt compounded with 40% Polyox N-80 and 0.5% of either Esacure KIP 150, Irgacure 127 or Irgacure 651 as photo-initiator. The preparation of the samples was as described in Example 1. The UV curing was done with a Fusion 600I H-lamp (600 W/inch, arc about 20 cm long, substrate placed about 26 cm from the bulb) at 100% intensity for 4 minutes.

The blends were hot press laminated onto substrates of Tecogel 500, Estane 58212, and 90% Estane 58212 with 10% phenoxy resin PKHH.

Results and Discussion

The adhesion to the substrate was subjectively evaluated after swelling in water for at least 24 hours.

| Photo-initiator | Tecogel 500 | | Estane 58212 | | 90% Estane 58212 + 10% PKHH | |
|---|---|---|---|---|---|---|
| | UV cured | Not UV cured | UV cured | Not UV cured | UV cured | Not UV cured |
| Esacure KIP 150 | 3 | 2 | 4 | 2 | 4 | 2 |
| Irgacure 127 | 4 | 3 | 3 | 2 | 2 | 1 |
| Irgacure 651 | 3 | 1 | 4 | 1 | 4 | 1 |

All three photo-initiators improved the adhesion to all three substrates, although Irgacure 127 was less effective than Esacure KIP 150 and Irgacure 651 in effecting adhesion to substrates containing Estane 58212. The addition of phenoxy resin did not improve the bonding between the layers. Furthermore, a comparison between (a) the sample with Esacure KIP 150 on Estane 58212 that was UV cured with the Fusion lamp, and (b) the corresponding sample from Example 3 that was cured with the weaker lamp from Dr. Hönle showed, that the higher UV intensity used with the former sample was very beneficial for the adhesion of the coating on the substrate.

Example 5

Preparation 59.5% of either of two different lots of Tecogel 2000 with different water absorption capacity (CD53RA015 and PM-03-36D) were hot melt compounded with 40% Polyox N-80 and 0.5% Irgacure 651.

The preparation of the samples was as described in Example 1. The UV curing was done with a Fusion 600I H-lamp at 100% intensity for 2 minutes. The blends were hot press laminated onto substrates of Tecogel 500.

Results and Discussion

The adhesion to the substrate was evaluated subjectively after swelling in water for at least 24 hours.

| Ratio of Tecogel 2000 types CD53RA015:PM-03-36D | UV cured | Not UV cured |
|---|---|---|
| 100:0 | 4 | 2 |
| 40:60 | 2 | 1 |
| 20:80 | 2 | 1 |

Adding the extremely hydrophilic polyurethane PM-03-36D to the blend made it more difficult to UV bond the layer to the substrate. To get good adhesion the two layers need to be compatible with each other, so that during lamination there will be good mixing of the polymer chains at the interface. This would give a better cross-linking of the polymer chains from the two layers.

Example 6

| Ingredients | Compound A | Compound B | Compound C | Compound D |
|---|---|---|---|---|
| Tecogel 2000 | 59.7% | 39.8% | 19.9% | |
| Tecogel 500 | | | | 99.5% |
| PolyOx N-80 | 39.8% | 59.7% | 79.6% | |
| Irgacure 651 | 0.5% | 0.5% | 0.5% | 0.5% |

These ingredients were compounded together with a twin-screw extruder. The ingredients were fed to the extruder by gravimetric feeders, extruded into strands and pelletized. The extruder profile was:

| | zone 1 | zone 2 | zone 3 | zone 4 | zone 5 | zone 6 | zone 7 | zone 8 | zone 9 | Die |
|---|---|---|---|---|---|---|---|---|---|---|
| ° C. | 80 | 90 | 100 | 110 | 120 | 130 | 140 | 150 | 150 | 150 |

Two single screw extruders were then connected to a single crosshead dual tube die. Extruder #1 was charged with Compound D, and extruder #2 was charged with Compound A, B or C. The blends were extruded onto a prefabricated tube of Estane 58212 (see FIG. 1). Extruder #1 then extruded Compound D as the inner layer and extruder #2 extruded Compound A, B or C as the outer layer. The ratios of inner to outer layer was varied by adjusting the output of either extruder by increasing or lowering the screw speed. The thickness of the layers was adjusted by varying either the output or the haul-off speed.

The two extruders had the same temperature profile.

| | zone 1 | zone 2 | zone 3 | zone 4 | zone 5 | Head | Die |
|---|---|---|---|---|---|---|---|
| ° C. | 40 | 105 | 155 | 175 | 175 | 195 | 200 |

After extrusion, the coated tube was cut into 35 cm long samples and UV cured for 0, 60, 120, or 180 seconds with a Fusion 600I H-lamp at 100% intensity. The UV cured samples were swelled in a 0.9% saline solution for at least 24 hours. The adhesion of the layers to the tube were subjectively evaluated as in Example 1.

The period of the UV treatment of Compounds A, B and C is shown in FIG. 6. The adhesion to the tube was improved for all three compounds when they were UV cured. Compound C with the lowest amount of polyurethane in the outer layer needed the longest UV treatment to adhere properly to the tube. FIG. 2 shows delamination from the tube after swelling due to insufficient UV curing. FIG. 3 shows swelled layers bonded to the tube due to proper UV curing.

Figure 7:
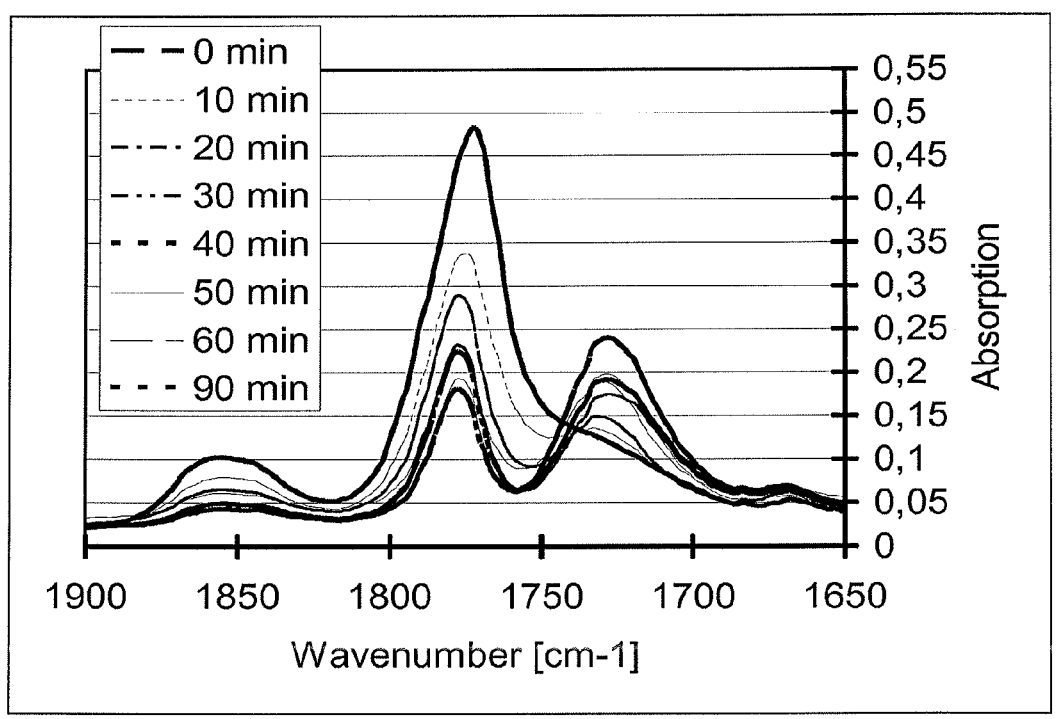
FIG. 7 shows the progress of the reaction between Gantrez AN 119 BF, MPEG 350 and Irgacure 2959 at 100° C., as measured by FT-IR (see Example 7 for details).

Example 7: Coatings Consisting of Polyox with and without 20% Irgacure 2959 as Photo-Initiator, Bound and Unbound to Gantrez AN 119 BF Preparation of Sample 7A: Irgacure 2959 Bound to Polymer at 100° C. and then Compounded with Polyox 7.8 g Gantrez AN 119 BF (50 mmol anhydride), 15.5 g MPEG 350 (44 mmol), and 1.7 g Irgacure 2959 (7.6 mmol) were mixed and compounded in a Brabender mixer at 100° C. for 90 minutes. No work-up was performed; this was Mixture 1. The progress of the reaction with time was monitored by FT-IR as the decrease of the anhydride peaks at 1854-5 $cm^{-1}$ and 1772-6 $cm^{-1}$ and the simultaneous increase in the ester/carboxylic acid peak at 1726 $cm^{-1}$; see FIG. 7.

After about 90 minutes a substantial amount of the anhydride had reacted, and the level of remaining anhydride only decreased slowly, so the reaction was stopped at this time.

83.745 parts Polyox N-301 and 9.305 parts Polyox N-80 were premixed and melted by slow addition to a Brabender mixer at 120° C. After complete addition of Polyox, the mixture was compounded for 2 minutes, and 6.95 parts of Mixture 1 was added. The resulting mixture was compounded for 2 minutes at atmospheric pressure, then for 2 minutes in vacuum. This was Mixture 2, which contained 0.47 w/w-% Irgacure 2959.

Mixture 2 was hot pressed at 100° C. for a minute to form a circular slice with thickness 1 mm. A quarter of the slice was further hot pressed at 100° C. without distance pieces to a slice that was as thin as possible. The thickness was not measured routinely but was between 150 and 200 μm.

The thin slice of Mixture 2 was laminated on a sheet of Estane 58212, which had previously been wiped clean with ethanol, at 100° C. and 50 bars for about 30-45 seconds (no distance pieces used).

The sample was divided into two sections, that were both heated to 60-80° C. for 5-10 minutes until they were transparent. One sample was then immediately UV cured for 1 minute and the other for 5 minutes at a distance of about 26 cm from a Fusion 1600 H-lamp running at 100% intensity.

Preparation of Sample 7B: Irgacure 2959 Bound to Polymer at 120° C. and then Compounded with Polyox 7.8 g Gantrez AN 119 BF (50 mmol anhydride), 15.5 g MPEG 350 (44 mmol), and 1.7 g Irgacure 2959 (7.6 mmol) were mixed and compounded in a Brabender mixer at 120° C. for 90 minutes. The rest of the procedure was identical to that described for sample 7A. The samples contained 0.47% Irgacure 2959.

Preparation of Sample 7C: MPEG 350 Bound to Polymer and then Compounded with Polyox 7.2 g Gantrez AN 119 BF (46 mmol anhydride) and 17.8 g MPEG 350 (51 mmol) were mixed and heated for 24 hours at 90° C. in a heat cupboard. No work-up was performed; this was Mixture 3.

84.6 parts Polyox N-301 and 9.4 parts Polyox N-80 were premixed and melted by slow addition to a Brabender mixer at 120° C. After complete addition of Polyox, the mixture was compounded for 2 minutes, and 6.0 parts of Mixture 3 was added. The resulting mixture was compounded for 2 minutes at atmospheric pressure, then for 2 minutes in vacuum. This was Mixture 4, which contained no photo-initiator.

Mixture 4 was hot pressed, laminated and UV cured for 1 and 5 minutes, as described for sample 7A. The samples were subjectively evaluated as described for sample 7A.

Preparation of Sample 7D: MPEG 350 Bound to Polymer and Compounded with Polyox in One Step 1.5 parts Gantrez AN 119 BF, 3.0 parts MPEG 350, 85.95 parts Polyox N-301, and 9.55 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained no photo-initiator.

Preparation of Sample 7E: Irgacure 2959 not Bound to Polymer 3.04 parts Gantrez ES 225 (non-reactive homologue of Gantrez AN 119 BF), 3.00 parts MPEG 350, 0.48 parts Irgacure 2959, 84.13 parts Polyox N-301, and 9.35 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained 0.48% Irgacure 2959.

Preparation of Sample 7F: MPEG 350 not Bound to Polymer 3.04 parts Gantrez ES 225, 3.00 parts MPEG 350, 84.56 parts Polyox N-301, and 9.40 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained no photo-initiator.

Results and Discussion for Samples 7A-F

The samples were immersed in deionized water for at least 24 hours. The adhesion of the UV cured coatings to the Estane 58212 substrate was scored as described in Example 1. At the same time the cohesion of the gels was scored on a subjective scale from 1 to 6:
1=No cross-linking; coating dissolved
2=Very weak, loose gel which cannot be handled without breaking
3=Somewhat stable gel
4=Rather stable gel
5=Almost stable gel
6=Entirely stable and cohesive gel The results are shown here:

| Sample | Contains photo-initiator? | Reactive polymer? | 1 min. UV curing | | 5 min. UV curing | |
| --- | --- | --- | --- | --- | --- | --- |
| | | | Gel cohesion (1-6) | Adhesion to substrate (1-4) | Gel cohesion (1-6) | Adhesion to substrate (1-4) |
| 7A-100 | Yes | Yes | 1 | 1 | 3 | 1 |
| 7B-120 | Yes | Yes | 2 | 1 | 2.5 | 1 |
| 7C | No | Yes | 1 | 1 | 1 | 1 |
| 7D | No | Yes | 1 | 1 | 1 | 1 |
| 7E | Yes | No | 3.5 | 1 | 5.5 | 1 |
| 7F | No | No | 1 | 1 | 1 | 1 |

The sample with unbound photo-initiator (7E) gave a stronger gel than the samples with photo-initiator bound to the Gantrez polymer (7A-B) after both 1 and 5 minutes UV curing. Sample 7E gave an especially strong gel after 5 minutes UV curing. Furthermore, there was no significant difference between 7A and 7B, indicating that the formation of the polymer-bound photo-initiator was robust towards temperature changes during production. Gels with no photo-initiator (7C-D and 7F) had no cohesion. Hence photo-initiator was necessary to cross-link the coating in this system. None of the gels stuck to the substrate polymer.

In this and the later examples several measurements were made on systems that had not been UV cured. In all tested cases the gels were non-cohesive and non-adhesive, so the data were not shown.

Example 8: Coatings Consisting of Polyox and Tecogel 2000 with and without Irgacure 2959 and BTDA as Photo-Initiators Preparation of Sample 8A: Irgacure 2959 Bound to BTDA (Double Photo-Initiator System)

7.93 g 97% BTDA (23.9 mmol), 14.71 g MPEG 350 (42.0 mmol), and 2.36 g Irgacure 2959 (10.5 mmol) were mixed and heated for 24 hours at 90° C. in a heat cupboard. No work-up was performed; this was Mixture 5.

51.4 parts Polyox N-301, 5.7 parts Polyox N-80, and 38.1 parts Tecogel 2000 were premixed and melted by slow addition to a Brabender mixer at 120° C. After complete addition, the mixture was compounded for 10 minutes, and 4.8 parts of Mixture 5 was added. The resulting mixture was compounded for 2 minutes at atmospheric pressure, then for 2 minutes in vacuum. This was Mixture 6.

Mixture 6 was hot pressed, laminated and UV cured for 1 and 5 minutes, as described for sample 7A. The samples were subjectively evaluated as described for sample 7A. The samples contained 1.48% BTDA and 0.45% Irgacure 2959.

Preparation of Sample 8B: Photoactive Irgacure 2959 Bound to Photoinactive PMDA 5.98 g 97% PMDA (26.6 mmol), 16.39 g MPEG 350 (46.8 mmol), and 2.63 g Irgacure 2959 (11.7 mmol) were mixed and heated for 24 hours at 90° C. in a heat cupboard. No work-up was performed; this was Mixture 7.

51.4 parts Polyox N-301, 5.7 parts Polyox N-80, and 38.1 parts Tecogel 2000 were premixed and melted by slow addition to a Brabender mixer at 120° C. After complete addition, the mixture was compounded for 10 minutes, and 4.8 parts of Mixture 7 was added. The resulting mixture was compounded for 2 minutes at atmospheric pressure, then for 2 minutes in vacuum. This was Mixture 8.

Mixture 8 was hot pressed, laminated and UV cured for 1 and 5 minutes, as described for sample 7A. The samples were subjectively evaluated as described for sample 7A. The samples contained 0.50% Irgacure 2959.

Preparation of Sample 8C: Photoactive BTDA Bound to Photoinactive MPEG 350

7.54 g 97% BTDA (22.7 mmol) and 17.47 g MPEG 350 (49.9 mmol) were mixed and heated for 24 hours at 90° C. in a heat cupboard. No work-up was performed; this was Mixture 9.

52.2 parts Polyox N-301, 5.8 parts Polyox N-80, and 38.7 parts Tecogel 2000 were premixed and melted by slow addition to a Brabender mixer at 120° C. After complete addition, the mixture was compounded for 10 minutes, and 3.3 parts of Mixture 9 was added. The resulting mixture was compounded for 2 minutes at atmospheric pressure, then for 2 minutes in vacuum. This was Mixture 10.

Mixture 10 was hot pressed, laminated and UV cured for 1 and 5 minutes, as described for sample 7A. The samples were subjectively evaluated as described for sample 7A. The samples contained 0.97% BTDA.

Preparation of Sample 8D: Photoinactive MPEG 350 Bound to Photoinactive PMDA 5.65 g 97% PMDA (25.1 mmol) and 19.35 g MPEG 350 (55.3 mmol) were mixed and heated for 24 hours at 90° C. in a heat cupboard. No work-up was performed; this was Mixture 11.

51.4 parts Polyox N-301, 5.7 parts Polyox N-80, and 38.1 parts Tecogel 2000 were premixed and melted by slow addition to a Brabender mixer at 120° C. After complete addition, the mixture was compounded for 10 minutes, and 4.8 parts of Mixture 11 was added. The resulting mixture was compounded for 2 minutes at atmospheric pressure, then for 2 minutes in vacuum. This was Mixture 12.

Mixture 12 was hot pressed, laminated and UV cured for 1 and 5 minutes, as described for sample 7A. The samples were subjectively evaluated as described for sample 7A. The samples contained no photo-initiator.

Results and Discussion for Samples 8A-D

The samples were immersed in deionized water for at least 24 hours. The adhesion and cohesion of the UV cured coatings to the Estane 58212 substrate was scored as described in Example 7.

The results are shown here:

| Sample | Contains Irgacure 2959? | Contains BTDA? | 1 min. UV curing | | 5 min. UV curing | |
|---|---|---|---|---|---|---|
| | | | Gel cohesion (1-6) | Adhesion to substrate (1-4) | Gel cohesion (1-6) | Adhesion to substrate (1-4) |
| 8A | Yes | Yes | 6 | 3 | 6 | 3 |
| 8B | Yes | No | 6 | 1 | 6 | 1 |
| 8C | No | Yes | 6 | 3 | 5 | 3 |
| 8D | No | No | 1 | 1 | 6 | 1 |

Excellent gels resulted after 1 or 5 minutes UV curing when either or both of the photo-initiators Irgacure 2959 or BTDA were present in the recipe (samples 8A-C). Furthermore, when BTDA was present (samples 8A and 8C), the gels adhered strongly to the substrate, whereas PMDA-bound Irgacure 2959 alone (sample 8B) did not bind to the substrate. By contrast, the gel observed in sample 8D without photo-initiator was neither cohesive nor adhesive after 1 minute UV curing. However, after 5 minutes UV curing sample 8D produced an excellent coating, even if it did not stick to the substrate. Comparing Examples 7 and 8 it hence appeared that gels containing Tecogel 2000 were able to UV cure slowly in the absence of added photo-initiators, but if photo-initiator(s) were added, it was possible to increase the UV curing speed and to control the adhesion of the gels to the substrate.

Example 9: Coatings Consisting of Polyox with and without Tecogel 2000 with and without Unbound Irgacure 2959

Preparation of Sample 9A: Unbound Irgacure 2959 in a Gel Consisting of POLYOX 0.48 parts Irgacure 2959, 89.57 parts Polyox N-301, and 9.95 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained 0.48% Irgacure 2959.

Preparation of Sample 9B: Gel Consisting of Polyox 90 parts Polyox N-301 and 10 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained no photo-initiator.

Preparation of Sample 9C: Unbound Irgacure 2959 in a Gel Consisting of Polyox and Tecogel 2000

0.48 parts Irgacure 2959, 53.74 parts Polyox N-301, 5.97 parts Polyox N-80, and 39.81 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained 0.48% Irgacure 2959.

Preparation of Sample 9D: Gel Consisting of Polyox and Tecogel 2000

54 parts Polyox N-301, 6 parts Polyox N-80, and 40 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained no photo-initiator.

Results and Discussion for Samples 9A-D

The results are shown here:

| Sample | Contains Irgacure 2959? | Contains Tecogel? | 1 min. UV curing | | 5 min. UV curing | |
|---|---|---|---|---|---|---|
| | | | Gel cohesion (1-6) | Adhesion to substrate (1-4) | Gel cohesion (1-6) | Adhesion to substrate (1-4) |
| 9A | Yes | No | 3 | 1 | 4.5 | 1 |
| 9B | No | No | 1 | 1 | 1 | 1 |
| 9C | Yes | Yes | 6 | 3 | 6 | 3 |
| 9D | No | Yes | 2.5 | 3 | 2.5 | 3 |

In samples without Tecogel 2000 (9A-B) the presence of Irgacure 2959 (9A) gave a cohesive gel after UV curing, whereas the photo-initiator-free preparation 9B did not form any kind of cohesive gel after 1 or 5 minutes UV curing. Hence Irgacure 2959 gave cohesion to the gel which, however, did not stick to the substrate. With Tecogel 2000 in the samples (9C-D) all gels adhered strongly to the substrate, but the gels in sample 9C with Irgacure 2959 were superior relative to the gels from the photo-initiator-free preparation 9D.

In Example 8B Irgacure 2959 bound to PMDA in the presence of MPEG 350 produced an excellent gel which did not, however, adhere to the Estane 58212 substrate as sample 9C did, although the amounts of photo-initiator in the two preparations were almost identical. Hence the binding of Irgacure 2959 to PMDA and/or the presence of MPEG 350 may have decreased the ability of Irgacure 2959 to abstract hydrogen from the polyurethane substrate, resulting in poorer adhesion.

Samples 8D and 9D were also similar in the respect that both recipes contained Tecogel 2000 but no photo-initiator. However, in sample 8D a gel with excellent cohesion but no adhesion to the substrate was formed after 5 minutes UV curing, whereas sample 9D gave a very weak but adhesive gel after both 1 and 5 minutes. Hence it seemed that the MPEG 350-PMDA ester present in sample 8D was able to cross-link the gel with low efficiency but without binding the gel to the substrate, whereas the hydrophilic Tecogel 2000 polyurethane in sample 9D only barely made the gel cohesive but did manage to bind to the hydrophobic polyurethane substrate, possibly through urethane-urethane hydrogen bond formation.

Example 10: Coatings Consisting of SMA-Bound Irgacure 2959 and Polyox with and without Tecogel 2000

Synthesis of the Irgacure 2959 ester of SMA 1000 (Compound 1)

1.124 g SMA 1000 (4.81 mmol anhydride based on an average acid number of 480 mg KOH/g sample) and 1.373 g Irgacure 2959 (6.12 mmol) were dissolved in 12 g acetone. When 0.503 g 1-methylimidazole (6.13 mmol) was added as combined catalyst and base, the solution turned yellow. The mixture was placed in an airtight, pressure-resistant vial at 70° C.

The disappearance of anhydride groups was followed between 1770 and 1860 $cm^{-1}$ by FT-IR and indicated that the reaction was essentially complete after 63 hours (data not shown). Upon cooling the solution became unclear, and a little precipitate was observed. The solution was acidified with HCl to pH 1-2, and the SMA 1000 acid ester of Irgacure 2959 was extracted with ethyl acetate. After drying of the ethyl acetate phase and evaporation of the solvent a viscous, yellowish oil remained. The compound was dissolved in methanol, transferred to a tared Petri dish, put into a ventilated heat cupboard and dried at 70° C. for 80 min to a sticky, yellow compound; this was Compound 1. No further work-up was done. The yield was 2.00 g. The maximum theoretical amount of Irgacure 2959 in the polymer was 49 w/w-%. However, the maximum amount of Irgacure 2959 present in the preparation was determined by UV-Vis spectroscopy to be 22 w/w-%, on the assumption that the extinction coefficients of free and bound Irgacure 2959 were identical. This was an upper estimate, because no correction was made for a possible background absorption at the wavelength of maximum absorbance of Irgacure 2959 (274-5 nm in methanol and 1,3-dioxolane).

Preparation of Sample 10A: Irgacure 2959 Bound to SMA 1000 in a Gel Consisting of Polyox 0.91 parts Compound 1, 89.18 parts Polyox N-301, and 9.91 parts Polyox N-80 were compounded in a Brabender mixer at 120° C. for 2 minutes at atmospheric pressure, then for 2 minutes in vacuum. This mixture contained maximum 0.20% Irgacure 2959. The mixture was hot pressed, laminated and UV cured for 1 and 5 minutes, as described for sample 7A.

Synthesis of the Irgacure 2959 Ester of SMA 2000 (Compound 2)

1.428 g SMA 2000 (4.52 mmol anhydride based on an average acid number of 355 mg KOH/g sample) and 1.151 g Irgacure 2959 (5.13 mmol) were dissolved in 12 g acetone. When 0.421 g 1-methylimidazole (5.13 mmol) was added, the solution turned yellow. The mixture was placed in an airtight, pressure-resistant vial at 70° C. The disappearance of anhydride groups was followed between 1770 and 1860 $cm^{-1}$ by FT-IR, which indicated that the reaction was 60-65% complete after 63 hours (data not shown). Hence the reaction was slower than with SMA 1000. The solution was acidified with HCl to pH 1-2, and the SMA 2000 acid ester of Irgacure 2959 was filtered off, dissolved in acetone, transferred to a tared Petri dish, put into a ventilated heat cupboard and dried at 70° C. for 170 min to a pale yellow, mainly hard crystalline substance with a few softer areas; this was Compound 2. No further work-up was done. The yield was 1.88 g. The maximum theoretical amount of Irgacure 2959 in the polymer was 41.5 w/w-%. However, the maximum amount of Irgacure 2959 present in the preparation was determined by UV-Vis spectroscopy to be 11 w/w-%.

Preparation of Sample 10B: Irgacure 2959 Bound to SMA 2000 in a Gel Consisting of Polyox 1.12 parts Compound 2, 88.99 parts Polyox N-301, and 9.89 parts Polyox N-80 were compounded in a Brabender mixer at 120° C. for 2 minutes at atmospheric pressure, then for 2 minutes in vacuum. This mixture contained 0.12% Irgacure 2959. The mixture was hot pressed, laminated and UV cured for 1 and 5 minutes, as described for sample 7A. The samples were subjectively evaluated as described for sample 7A.

Synthesis of the Irgacure 2959 Ester of SMA 3000 (Compound 3)

1.647 g SMA 3000 (4.18 mmol anhydride based on an average acid number of 285 mg KOH/g sample) and 0.991 g Irgacure 2959 (4.42 mmol) were dissolved in 12 g acetone. When 0.363 g 1-methylimidazole (4.42 mmol) was added, the solution turned yellow. The mixture was placed in an airtight, pressure-resistant vial at 70° C. The disappearance of anhydride groups was followed between 1770 and 1860 $cm^{-1}$ by FT-IR, which indicated that the reaction was 60-65% complete after 63 hours (data not shown). Hence the reaction was slower than with SMA 1000 but about as fast as with SMA 2000. The solution was acidified with HCl to pH 1-2, and the SMA 3000 acid ester of Irgacure 2959 was extracted with methyl isobutyl ketone. After drying of the methyl isobutyl ketone phase and evaporation of the solvent a yellow substance remained. The compound was dissolved in acetone, transferred to a tared Petri dish, put into a ventilated heat cupboard and dried at 70° C. overnight to a pale yellow, transparent, brittle glass; this was Compound 3. No further work-up was done. The yield was 2.22 g. The maximum theoretical amount of Irgacure 2959 in the polymer was 36 w/w-%. However, the maximum amount of Irgacure 2959 present in the preparation was determined by UV-Vis spectroscopy to be 25 w/w-%

Preparation of Sample 10C: Irgacure 2959 Bound to SMA 3000 in a gel Consisting of POLYOX 1.33 parts Compound 3, 88.80 parts Polyox N-301, and 9.87 parts Polyox N-80 were compounded in a Brabender mixer at 120° C. for 2 minutes at atmospheric pressure, then for 2 minutes in vacuum. This mixture contained maximum 0.33% Irgacure 2959. The mixture was hot pressed, laminated and UV cured for 1 and 5 minutes, as described for sample 7A. The samples were subjectively evaluated as described for sample 7A.

Preparation of Sample 10D: Irgacure 2959 Bound to SMA 1000 in a Gel Consisting of POLYOX and Tecogel 2000

0.91 parts Compound 1, 53.51 parts Polyox N-301, 5.94 parts Polyox N-80, and 39.64 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained maximum 0.20% Irgacure 2959.

Preparation of Sample 10E: Irgacure 2959 Bound to SMA 2000 in a Gel Consisting of Polyox and Tecogel 2000

1.12 parts Compound 2, 53.40 parts Polyox N-301, 5.93 parts Polyox N-80, and 39.55 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained maximum 0.12 Irgacure 2959.

Preparation of Sample 10F: Irgacure 2959 Bound to SMA 3000 in a Gel Consisting of Polyox and Tecogel 2000

1.33 parts Compound 3, 53.28 parts Polyox N-301, 5.92 parts Polyox N-80, and 39.47 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained maximum 0.33% Irgacure 2959.

Results and Discussion for Samples 10A-F

The results are shown here:

|  |  |  | 1 min. UV curing | | 5 min. UV curing | |
|---|---|---|---|---|---|---|
| Sample | SMA type | Contains Tecogel? | Gel cohesion (1-6) | Adhesion to substrate (1-4) | Gel cohesion (1-6) | Adhesion to substrate (1-4) |
| 10A | 1000 | No | 2 | 1 | 4.5 | 1 |
| 10B | 2000 | No | 1 | 1 | 1 | 1 |
| 10C | 3000 | No | 4.5 | 1 | 6 | 3 |
| 10D | 1000 | Yes | 4.5 | 3 | 6 | 2 |
| 10E | 2000 | Yes | 2 | 3 | 2 | 3 |
| 10F | 3000 | Yes | 6 | 3 | 4.5 | 3 |

Within the samples with a pure Polyox coating (10A-C) as well as within the samples with Tecogel 2000 added to the coating (10D-F) the cohesion of the gels follows the same pattern: SMA 3000 (0.33% Irgacure 2959)>SMA 1000 (0.20% Irgacure 2959)>SMA 2000 (0.12% Irgacure 2959). This order follows the concentration of Irgacure 2959 in the samples, whereas the order of the SMA polymers seems to be random. Hence the concentration of Irgacure 2959 must be at least 0.3% in order to achieve a good UV cross-linking of the gels, whereas the effect of the SMA type appears to be smaller.

When sample 10C was UV cured for 5 minutes a superb gel resulted which, in addition, adhered strongly to the substrate, even though no Tecogel 2000 was present. This effect may be due to the still relatively low concentration of Irgacure 2959 in sample 10C, which allows for better through curing, or the effect may be due to an especially good compatibility of the SMA-bound Irgacure 2959 with both substrate and Polyox.

Sample 10F produced an excellent Tecogel-containing gel with strong adhesion to the substrate after just 1 minute UV curing, but so did samples 8A, 8C and 9C, so this was not a unique feature of the SMA-bound Irgacure 2959.

Example 11: Coatings Consisting of Polyox and Irgacure 2959 Bound to Aliphatic, Hydrophobic Polyurethanes Compounds 4 and 5 were custom synthesized by Bomar Specialties Co (Winsted, Conn.) and distributed in Europe by IGM Resins (Waalwijk, the Netherlands). Compound 4 was an aliphatic, trifunctional polyether urethane of medium molecular weight, which was functionalised with Irgacure 2959 at all three ends. The content of Irgacure 2959 in Compound 4 was 33.0 w/w-%, as indicated by Bomar. Compound 5 was an aliphatic, linear polyether urethane of medium molecular weight, which was functionalised with Irgacure 2959 at both ends. The content of Irgacure 2959 in Compound 5 was 15.5 w/w-%, as indicated by Bomar. Neither compound contained any acrylate groups, as determined by FT-IR (data not shown).

Preparation of Sample 11A: 1% Compound 4 in a Gel Consisting of Polyox 1 part Compound 4, 89.1 parts Polyox N-301, and 9.9 parts Polyox N-80 were compounded in a Brabender mixer at 120° C. for 2 minutes at atmospheric pressure, then for 2 minutes in vacuum. This mixture contained 0.33% Irgacure 2959. The mixture was hot pressed, laminated and UV cured for 1 and 5 minutes, as described for sample 7A. The samples were subjectively evaluated as described for sample 7A.

Preparation of Sample 11B: 5% Compound 4 in a Gel Consisting of Polyox 5 parts Compound 4, 85.5 parts Polyox N-301, and 9.5 parts Polyox N-80 were compounded in a Brabender mixer at 120° C. for 2 minutes at atmospheric pressure, then for 2 minutes in vacuum. This mixture contained 1.65% Irgacure 2959. The mixture was hot pressed, laminated and UV cured for 1 and 5 minutes, as described for sample 7A. The samples were subjectively evaluated as described for sample 7A.

Preparation of Sample 11C: 10% Compound 4 in a Gel Consisting of Polyox 10 parts Compound 4, 81 parts Polyox N-301, and 9 parts Polyox N-80 were compounded in a Brabender mixer at 120° C. for 2 minutes at atmospheric pressure, then for 2 minutes in vacuum. This mixture contained 3.30% Irgacure 2959. The mixture was hot pressed, laminated and UV cured for 1 and 5 minutes, as described for sample 7A. The samples were subjectively evaluated as described for sample 7A.

Preparation of Sample 11D: 1% Compound 5 in a Gel Consisting of Polyox 1 part Compound 5, 89.1 parts Polyox N-301, and 9.9 parts Polyox N-80 were compounded in a Brabender mixer at 120° C. for 2 minutes at atmospheric pressure, then for 2 minutes in vacuum. This mixture contained 0.16% Irgacure 2959. The mixture was hot pressed, laminated and UV cured for 1 and 5 minutes, as described for sample 7A. The samples were subjectively evaluated as described for sample 7A.

Preparation of Sample 11E: 5% Compound 5 in a Gel Consisting of Polyox 5 parts Compound 5, 85.5 parts Polyox N-301, and 9.5 parts Polyox N-80 were compounded in a Brabender mixer at 120° C. for 2 minutes at atmospheric pressure, then for 2 minutes in vacuum. This mixture contained 0.78% Irgacure 2959. The mixture was hot pressed, laminated and UV cured for 1 and 5 minutes, as described for sample 7A. The samples were subjectively evaluated as described for sample 7A.

Preparation of Sample 11F: 10% Compound 5 in a Gel Consisting of Polyox 10 parts Compound 5, 81 parts Polyox N-301, and 9 parts Polyox N-80 were compounded in a Brabender mixer at 120° C. for 2 minutes at atmospheric pressure, then for 2 minutes in vacuum. This mixture contained 1.55% Irgacure 2959. The mixture was hot pressed, laminated and UV cured for 1 and 5 minutes, as described for sample 7A. The samples were subjectively evaluated as described for sample 7A.

Results and Discussion for Samples 11A-F

The results are shown here:

| Sample | % Irgacure 2959 | Compound number | 1 min. UV curing | | 5 min. UV curing | |
|---|---|---|---|---|---|---|
| | | | Gel cohesion (1-6) | Adhesion to substrate (1-4) | Gel cohesion (1-6) | Adhesion to substrate (1-4) |
| 11A | 0.33 | 4 | 4 | 1 | 5 | 3 |
| 11B | 1.65 | 4 | 5 | 1 | 5 | 3 |
| 11C | 3.30 | 4 | 5 | 1 | 5 | 3 |
| 11D | 0.16 | 5 | 2 | 1 | 2 | 1 |
| 11E | 0.78 | 5 | 5 | 1 | 5 | 1 |
| 11F | 1.55 | 5 | 5 | 1 | 5 | 1 |

Samples 11A-C produced strong gels that adhered well to the substrate after 5 minutes UV curing. Samples 11E-F also produced strong gels after 5 minutes UV curing, but these gels did not adhere to the substrate. These experiments clearly demonstrated that the geometry of the photoactive polymer was more important for the adhesion to the substrate than the sheer concentration of photo-initiating groups in the gel. That is, the trifunctional photoactive polyurethane Compound 4 adhered strongly to the substrate polymer whereas the difunctional Compound 5 did not. It also appeared that 0.16% Irgacure 2959 in the gel was not enough to induce efficient cross-linking of the gel, even after 5 minutes UV curing (sample 11D), as this result was also found for sample 10B.

Example 12: Coatings Consisting of Polyox with and without Tecogel 2000 with BTDA-Jeffamine Condensation Polymers as Photo-Initiator Synthesis of BTDA-Jeffamine D-230 Condensation Polymer (Compound 6)

Figure 8:
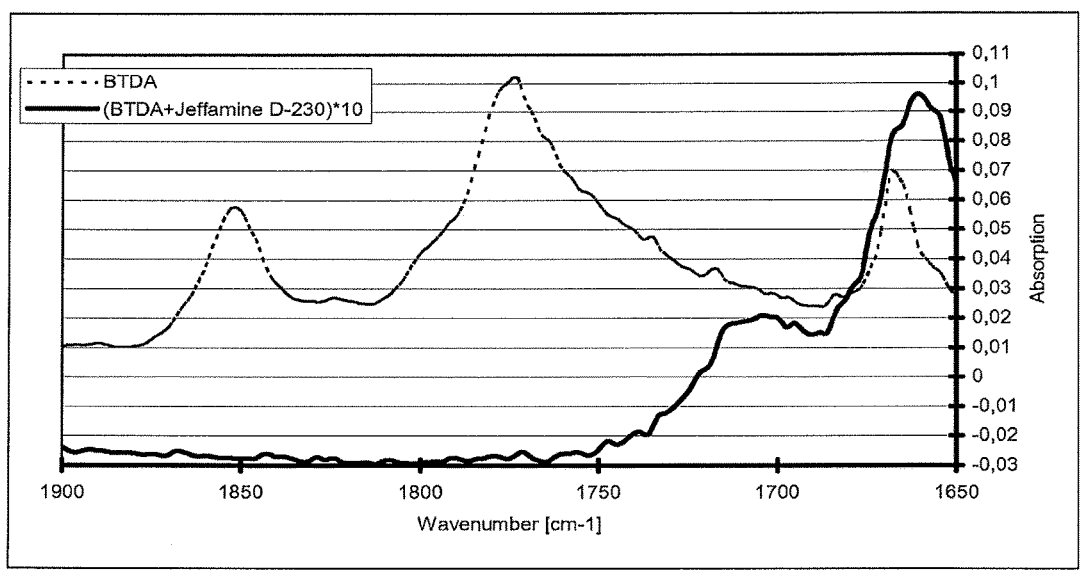
FIG. 8 shows the instantaneous reaction between 3,3',4,4'-benzophenonetetracarboxylic acid dianhydride (BTDA) and the diamine Jeffamine D-230 (see Example 12 for details).

1.77 g 97% BTDA (5.33 mmol) was dissolved in 12 g DMSO by magnetic stirring and heating to 60° C. 1.23 g Jeffamine D-230 (5.35 mmol) was added with perceptible heat evolution. FT-IR recorded within minutes after mixing indicated that the reaction between the dianhydride and the diamine was instantaneous; see FIG. 8.

The solution was acidified with HCl to pH 1-2, and the BTDA-Jeffamine D-230 condensation polymer was extracted with dichloromethane. The dichloromethane phase was dried and the dichloromethane evaporated; this was Compound 6. The compound contained maximum 11.4° A) BTDA, but this could not be verified by UV-Vis spectroscopy because of a large background absorption at the maximum absorption of BTDA (257 nm in ethanol).

Preparation of Sample 12A: BTDA/Jeffamine D-230 Condensation Polymer as Photo-Initiator in a Gel Consisting of Polyox 1.73 parts Compound 6, 88.44 parts Polyox N-301, and 9.83 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained maximum 0.20% BTDA.

Preparation of Sample 12B: BTDA/Jeffamine D-230 Condensation Polymer as Photo-Initiator in a Gel Consisting of Polyox and Tecogel 2000

1.73 parts Compound 6, 53.06 parts Polyox N-301, 5.90 parts Polyox N-80, and 39.31 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A. The samples contained maximum 0.20% BTDA.

Results and Discussion for Samples 12A-B

The results are shown here:

| Sample | Contains Tecogel? | 1 min. UV curing | | 5 min. UV curing | |
|---|---|---|---|---|---|
| | | Gel cohesion (1-6) | Adhesion to substrate (1-4) | Gel cohesion (1-6) | Adhesion to substrate (1-4) |
| 12A | No | 3 | 1 | 4 | 1 |
| 12B | Yes | 4 | 3 | 5 | 3 |

A relatively strong gel was formed from samples 12A-B after 1 minute UV curing in spite of the low concentration of photo-initiator used, but the gel strength at 5 minutes UV curing was better. The Tecogel 2000-containing gel 12B was slightly stronger than the pure Polyox gel of sample 12A. Furthermore, the gel of sample 12B adhered strongly to the substrate, whereas the gel of sample 12A did not. In this respect sample 12B was similar to many of the other Tecogel 2000-containing samples with photo-initiator, which also adhered well to the substrate.

Example 13: Coatings Consisting of Polyox with and without Tecogel 2000 with Benzophenone Bound to Boltorn or Joncryl Polyols as Photo-Initiator Synthesis of 4-benzoylbenzoyl chloride 5.00 g 4-benzoylbenzoic acid (22.1 mmol), 10.0 mL thionyl chloride (16.31 g, 137 mmol) and one drop of DMF in a 100 mL round-bottom flask was refluxed for 75 minutes in an oil bath kept at 100° C. The stream of gaseous $SO_2$ and HCl, that was formed during the reaction, was directed via rubber tubing and a glass pipette onto the surface of a vigorously stirred 1 M NaOH solution, where most of the gas was absorbed and transformed to sulphite and chloride. Care was taken not to let the tip of the glass pipette touch the surface of the sodium hydroxide solution because of the risk of back suction of sodium hydroxide into the system.

After 75 minutes reflux the oil bath was removed, and the reaction mixture was cooled to room temperature. The condenser was removed and the setup rearranged, so a piece of rubber tubing from the round-bottom flask was directed to the entrance of a membrane pump, and the exit from the membrane pump was directed via rubber tubing and a glass pipette towards the stirred 1 M NaOH solution. The glass pipette should be at a larger distance from the NaOH solution than during the first part of the experiment, because the air flow through the pump was much larger than the spontaneous flow of gaseous $SO_2$ and HCl from the first part of the experiment. Then suction was applied and the unreacted $SOCl_2$ removed, first for 10 minutes at room temperature and later with gentle heating of the reaction mixture in the still warm oil bath for another 10 minutes. The flask with the pale, yellow, solid 4-benzoylbenzoyl chloride was stoppered until it was used in the next step of the synthesis. The membrane pump was flushed free of residual $SOCl_2$ by direct suction of 500 mL of deionized water through the pump and into one of two small holes in the lid of a plastic bucket in a fume hood.

Synthesis of the Boltorn H-20 Ester of 4-Benzoylbenzoic Acid (Compound 7)

2.43 g Boltorn H-20 (22.1 mmol OH based on an average OH-number of 510 mg KOH/g sample) was dissolved in 50 mL pyridine (48.9 g; 0.618 mol) in a 250 mL round-bottom flask with a directly attached distillation head. The mixture was dried by distillation by means of a heating mantle with magnetic stirrer, since water forms a low boiling azeotrope with pyridine (azeotrope by 93.6° C.; azeotrope contains 75.5 mol-% water). As soon as the water was removed, the distillation temperature increased to the boiling point of pure pyridine, i.e. 115.3° C.; from this point an additional 4-5 mL pyridine/water was collected in a measuring cylinder through a small funnel.

A 100 mL dropping funnel, which had been dried in a heat cupboard at 130° C., was placed on the 100 mL round-bottom flask containing 4-benzoylbenzoyl chloride (see above). The warm, dried solution of Boltorn H-20 was transferred to the dropping funnel, and a nitrogen bubbler was attached to exclude moisture. 10-15 mL of the Boltorn solution was added at such a rate that only a small amount of gaseous HCl was formed above the liquid; this should re-enable magnetic stirring in the flask. The rest of the solution was added at such a rate that the temperature of the outside of the flask did not exceed about 40° C., as judged by the bare hand (no external cooling or heating was applied). The reaction mixture became brown. If necessary, the solution was cooled in an ice bath. Towards the end of Boltorn addition the reaction mixture became thicker because of the precipitation of apparently light brown pyridinium chloride. After about an hour the heat evolution had stopped, and the reaction mixture had reverted to room temperature as a sign that the reaction was complete.

Excess concentrated HCl was added to protonate all pyridine to make it water soluble, and the Boltorn ester was extracted from the aqueous phase into 3×50 mL $CH_2Cl_2$. The organic extract was dried overnight with $MgSO_4$ and the $CH_2Cl_2$ evaporated. The Boltorn H-20 ester of 4-benzoylbenzoic acid was a light tan, hard solid. This was Compound 7.

Preparation of Sample 13A: Boltorn H-20 Ester of 4-Benzoylbenzoic Acid as Photo-Initiator in a Gel Consisting of Polyox 1.45 parts Compound 7, 88.695 parts Polyox N-301, and 9.855 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Synthesis of the Boltorn H-30 Ester of 4-Benzoylbenzoic Acid (Compound 8)

2.48 g Boltorn H-30 (22.1 mmol OH based on an average OH-number of 500 mg KOH/g sample) was dissolved in 50 mL pyridine (48.9 g; 0.618 mol), dried and made to react with 4-benzoylbenzoyl chloride produced from 5.00 g 4-benzoylbenzoic acid, as described in the synthesis of the Boltorn H-20 ester of 4-benzoylbenzoic acid (Compound 7). The Boltorn H-30 ester of 4-benzoylbenzoic acid was a light tan wax. This was Compound 8.

Preparation of Sample 13B: Boltorn H-30 Ester of 4-Benzoylbenzoic Acid as Photo-Initiator in a Gel Consisting of Polyox 1.46 parts Compound 8, 88.69 parts Polyox N-301, and 9.85 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Synthesis of 2-benzoylbenzoyl chloride, batch #1 (abbreviated "2-BBCl-1")

The synthesis of 2-BBCl-1 was carried out like the synthesis of 4-benzoylbenzoyl chloride (see above). However, 2-BBCl-1 was a yellow oil and not a solid like 4-benzoylbenzoyl chloride.

Synthesis of the Boltorn H-20 Ester of 2-Benzoylbenzoic Acid (Compound 9)

2.43 g Boltorn H-20 (22.1 mmol OH based on an average OH-number of 510 mg KOH/g sample) was dissolved in 50 mL pyridine (48.9 g; 0.618 mol), dried and made to react with 2-BBCl-1 produced from 5.00 g 2-benzoylbenzoic acid as described above. The Boltorn H-20 ester of 2-benzoylbenzoic acid was a light tan, hard solid. This was Compound 9.

Preparation of Sample 13C: Boltorn H-20 Ester of 2-Benzoylbenzoic Acid as Photo-Initiator in a Gel Consisting of Polyox 1.45 parts Compound 9, 88.695 parts Polyox N-301, and 9.855 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Synthesis of the Boltorn H-30 Ester of 2-Benzoylbenzoic Acid (Compound 10)

2.48 g Boltorn H-30 (22.1 mmol OH based on an average OH-number of 500 mg KOH/g sample) was dissolved in 50 mL pyridine (48.9 g; 0.618 mol), dried and made to react with 2-BBCl-1 produced from 5.00 g 2-benzoylbenzoic acid as described above. The Boltorn H-30 ester of 2-benzoylbenzoic acid was a light tan, hard solid. This was Compound 10.

Preparation of Sample 13D: Boltorn H-30 Ester of 2-Benzoylbenzoic Acid as Photo-Initiator in a Gel Consisting of Polyox 1.46 parts Compound 10, 88.69 parts Polyox N-301, and 9.85 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Synthesis of the Joncryl 804 ester of 2-Benzoylbenzoic Acid (Compound 11)

10.15 g Joncryl 804 (7.96 mmol OH based on an average OH-number of 44 mg KOH/g sample) was dissolved in 75 mL pyridine (73.35 g; 0.927 mol), dried and made to react with 2-BBCl-1 produced from 1.80 g 2-benzoylbenzoic acid (7.96 mmol) which was made as described above, however only with 3.6 mL thionyl chloride instead of 10.0 mL. The synthesis of the Joncryl 804 ester of 2-benzoylbenzoic acid was like the synthesis of the Boltorn H-20 ester of 4-benzoylbenzoic acid (Compound 7). The Joncryl 804 ester of 2-benzoylbenzoic acid was an almost transparent wax. This was Compound 11.

Preparation of Sample 13E: Joncryl 804 Ester of 2-Benzoylbenzoic Acid as Photo-Initiator in a Gel Consisting of Polyox 6.45 parts Compound 11, 84.19 parts Polyox N-301, and 9.36 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13F: 2-Benzoylbenzoic Acid not Bound to Boltorn H-20 in a Gel Consisting of Polyox 0.24 parts 2-benzoylbenzoic acid, 1.21 parts Boltorn H-20, 88.695 parts Polyox N-301, and 9.855 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13G: 2-Benzoylbenzoic Acid not Bound to Joncryl 804 in a Gel Consisting of Polyox 1.00 part 2-benzoylbenzoic acid, 5.45 parts Joncryl 804, 84.19 parts Polyox N-301, and 9.36 parts Polyox N-80 were compounded in a Brabender mixer at 120° C. for 2 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13H: Boltorn H-20 Ester of 4-Benzoylbenzoic Acid as Photo-Initiator in a Gel Consisting of Polyox and Tecogel 2000

1.45 parts Compound 7, 53.22 parts Polyox N-301, 5.91 parts Polyox N-80, and 39.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13I: Boltorn H-30 Ester of 4-Benzoylbenzoic Acid as Photo-Initiator in a Gel Consisting of Polyox and Tecogel 2000

1.46 parts Compound 8, 53.21 parts Polyox N-301, 5.91 parts Polyox N-80, and 39.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13J: Boltorn H-20 Ester of 2-Benzoylbenzoic Acid as Photo-Initiator in a Gel Consisting of Polyox and Tecogel 2000

1.45 parts Compound 9, 53.22 parts Polyox N-301, 5.91 parts Polyox N-80, and 39.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13K: Boltorn H-30 Ester of 2-Benzoylbenzoic Acid as Photo-Initiator in a Gel Consisting of Polyox and Tecogel 2000

1.46 parts Compound 10, 53.21 parts Polyox N-301, 5.91 parts Polyox N-80, and 39.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13L: Joncryl 804 Ester of 2-Benzoylbenzoic Acid as Photo-Initiator in a Gel Consisting of Polyox and Tecogel 2000

6.45 parts Compound 11, 50.52 parts Polyox N-301, 5.61 parts Polyox N-80, and 37.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13M: 4-Benzoylbenzoic Acid not Bound to Boltorn H-30 in a Gel Consisting of Polyox and Tecogel 2000

0.24 parts 4-benzoylbenzoic acid, 1.21 parts Boltorn H-30, 53.22 parts Polyox N-301, 5.91 parts Polyox N-80, and 39.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Preparation of Sample 13N: 2-Benzoylbenzoic Acid not Bound to Joncryl 804 in a Gel Consisting of Polyox and Tecogel 2000

1.00 part 2-benzoylbenzoic acid, 5.45 parts Joncryl 804, 50.52 parts Polyox N-301, 5.61 parts Polyox N-80, and 37.42 parts Tecogel 2000 were compounded in a Brabender mixer at 120° C. for 10 minutes at atmospheric pressure, then for 2 minutes in vacuum. The mixture was hot pressed, laminated and UV cured for 1 and 5 minutes, as described for sample 7A. The samples were subjectively evaluated as described for sample 7A.

Results and Discussion for Samples 13A-N

The results are shown here:

| Sample | Photo-initiator? | PI bound? | Polymer? | Tecogel? | 1 min. UV curing Cohesion (1-6) | 1 min. UV curing Adhesion (1-4) | 5 min. UV curing Cohesion (1-6) | 5 min. UV curing Adhesion (1-4) |
|---|---|---|---|---|---|---|---|---|
| 13A | 4-BBA | Yes | H-20 | No | 5.5 | 1 | 5.5 | 3 |
| 13B | 4-BBA | Yes | H-30 | No | 4 | 1 | 4.5 | 4 |
| 13C | 2-BBA | Yes | H-20 | No | 6 | 1 | 6 | 1 |
| 13D | 2-BBA | Yes | H-30 | No | 6 | 1 | 6 | 1 |
| 13E | 2-BBA | Yes | J804 | No | 6 | 1 | 6 | 1 |
| 13F | 2-BBA | No | H-20 | No | 1 | 1 | 6 | 1 |
| 13G | 2-BBA | No | J804 | No | 6 | 1 | 6 | 2 |
| 13H | 4-BBA | Yes | H-20 | Yes | 5.5 | 3 | 5 | 4 |
| 13I | 4-BBA | Yes | H-30 | Yes | 4 | 3 | 6 | 3 |
| 13J | 2-BBA | Yes | H-20 | Yes | 6 | 1 | 6 | 1 |
| 13K | 2-BBA | Yes | H-30 | Yes | 6 | 3 | 6 | 3 |
| 13L | 2-BBA | Yes | J804 | Yes | 6 | 3 | 6 | 3 |
| 13M | 4-BBA | No | H-30 | Yes | 5.5 | 3 | 5.5 | 3 |
| 13N | 2-BBA | No | J804 | Yes | 6 | 1 | 6 | 4 |

4-BBA: 4-Benzoylbenzoic acid.
2-BBA: 2-Benzoylbenzoic acid.
PI: Photo-initiator.
H-20: Boltorn H-20.
H-30: Boltorn H-30.
J804: Joncryl 804.

Comparing the samples 13A-E, which all had bound photo-initiators, it was clear that only 4-BBA (13A-B) could secure good adhesion of the coating to the substrate after 5 minutes UV curing of a Polyox-coating without Tecogel 2000, whereas 2-BBA could not (13C-D). On the other hand 2-BBA formed stronger Polyox gels than 4-BBA. Sample 13F with unbound 2-BBA and H-20 did not form a strong gel after 1 minute UV curing, as opposed to all other photo-initiator combinations in pure Polyox; apparently H-20 worked best with the photo-initiator bound to it. Joncryl 804 made very strong gels with both bound and unbound 2-BBA but could not stick to the substrate.

In the gels with Tecogel 2000 there was again a clear tendency that bound or unbound 2-BBA formed stronger gels than bound or unbound 4-BBA (compare samples 13H—N). As opposed to the pure Polyox gels, however, with Tecogel 2000 present all bound photo-initiators gave strong adhesion to the polyurethane substrate after just 1 minute UV curing; except for 2-BBA with H-20 (sample 133), which failed entirely to give an adhesive coating, just as when no Tecogel was present (sample 13C). Apparently the overall performance of photo-initiators derived from Boltorn H-20 was slightly lower than those derived from Boltorn H-30. The unbound 2-BBA with Joncryl 804 (sample 13N) only managed to bind tightly to the substrate after 5 minutes UV curing, whereas the corresponding bound photo-initiator (sample 13L) made the gel bind strongly to the substrate after just 1 minute UV curing.

Example 14: Model Coatings Consisting of Polyox and/or a Thermoplastic Matrix Polymer with Covalently Bound Photo-Initiator Synthesis of Benzoyloxylated Polyox WSR N-80 in Benzene 2.00 g Polyox WSR N-80, 2.2 mg CuCl, and 200 mL benzene were placed in a three-necked 500 mL round-bottomed flask with a condenser, a dropping funnel and a stopper and purged with $N_2$, leaving the flask under a $N_2$ blanket. 885 μL tert-butyl peroxybenzoate in 24 mL benzene was added drop-wise from the dropping funnel during vigorous magnetic stirring. During the addition the solution acquired a bluish colour.

After 72 hours the bluish colour had almost vanished. 2.4 mL 2 M $Na_2CO_3$ was added during stirring, a distillation head was attached, and the water was removed azeotropically. Some frothing was observed when about 5 mL benzene-water mixture had distilled, but nothing dramatic. A total of 55 mL liquid was distilled to make sure all water had gone. The solution was cooled, the salts filtered off, transferred the filtrate to a 500 mL beaker, and added 100 mL pentane. The yellow, rubbery product precipitated out on the walls and bottom of the beaker and was scraped off with a glass spatula, then dried. Yield: 2.17 g. A strong IR peak at 1724 $cm^{-1}$ confirmed the presence of ester groups in the compound.

Reference Synthesis of Benzoyloxylated Polyox WSR N-80 in Methyl Isobutyl Ketone/Acetic Acid 10.0 g Polyox WSR N-80 (227 mmol ether linkages), 2.0 mg CuCl (MW=99.00 g/mol; 20 μmol), 475 mL MIBK (bp 117-8° C.) and 25 mL acetic acid (bp 117-8° C.) were placed in a 1 L three-necked flask with a condenser, a dropping funnel and a stopper. Acetic acid was added to increase the solubility of copper salts (see J. K. Kochi, A. Bemis (1968): "Catalytic reactions of peroxides, direct initiation by cuprous species", Tetrahedron, 24, 5099-5113).

The flask was flushed with $N_2$ and then heated to reflux under a $N_2$ blanket. 4 mL tert-butyl peroxybenzoate (density 1.034 g/mL; MW=194.23 g/mol; 21 mmol) was added drop-wise over 10-15 min. The addition of the peroxyester was accompanied by a colour change from yellowish to greenish because of the oxidation of Cu(I) to Cu(II). The progress of the reaction was followed by monitoring the disappearance of the peroxyester peak at 1756 $cm^{-1}$ by IR spectroscopy. After 19 hours the peroxyester peak had almost disappeared, and the greenish colour had changed back to yellow, as a further sign that all copper had been reduced to Cu(I) and no more peroxyester was present to oxidize it to Cu(II) (see D. J. Rawlinson, G. Sosnovsky (1972): "One-Step Substitutive Acyloxylation at Carbon. Part I. Reactions Involving Peroxides", Synthesis, International Journal of Methods in Synthetic Organic Chemistry, 1, 1-28).

The reaction mixture was poured into a 1 L beaker and slowly cooled in air to well below the melting point of Polyox (62-65° C.) and then in ice water, taking advantage of the fact that Polyox is much more soluble in boiling MIBK than in cold MIBK. The heavy, white, crystalline precipitate was filtered on a Büchner funnel, washed once with 50 mL cold 19:1 MIBK:acetic acid (v/v) to remove copper salts, two times with diethyl ether, and then dried. Yield: 6.17 g. IR spectroscopy revealed a small carbonyl peak at 1737 cm$^{-1}$, so basically the reaction did not give the desired product. Hence the reaction conditions must be carefully selected and optimized.

Synthesis of 2-Benzoylbenzoyl Chloride, Batch 2 (Abbreviated "2-BBCl-2")

74.8 g 4-benzoylbenzoic acid (331 mmol) and 150 mL thionyl chloride (245 g, 2.06 mol) were placed in a 500 mL round-bottomed flask fitted with a condenser and, on top of the condenser, tubing to lead gaseous HCl and $SO_2$ to above the surface of a vigorously stirred NaOH solution, where most of the gas was absorbed and transformed to sulphite and chloride. The NaOH solution contained more than 8.5 mol NaOH, i.e. more than the stoichiometric amount needed to neutralize 2.06 mol $SOCl_2$ according to: $SOCl_2 + 4 HO^- \rightarrow SO_3^{2-} + 2 Cl^- + 2 H_2O$.

10 drops of DMF were added to the reaction mixture, and heat was applied for 60 minutes to keep the mixture refluxing. The heating was removed and the reaction mixture cooled to room temperature. The condenser was removed and the setup rearranged, so a piece of rubber tubing from the round-bottomed flask was directed to the entrance of a membrane pump, and the exit from the membrane pump was directed via rubber tubing towards the stirred NaOH solution. The tubing should be at a larger distance from the NaOH solution than during the first part of the experiment, because the air flow through the pump was much larger than the spontaneous flow of gaseous $SO_2$ and HCl from the first part of the experiment. Then suction was applied and the unreacted $SOCl_2$ was removed by heating to 80° C. in vacuo for several days. The product (2-BBCl-2; MW=244.68 g/mol) was a yellow liquid, probably containing both the photochemically active 2-benzoylbenzoylchloride and the photochemically inactive pseudo-acid chloride (see M. S. Newman, C. Courduvelis (1966): "Reactions Proceeding by the [3.2.1] Bicyclic Path", *J. Am. Chem. Soc.*, 88(4), 781-4):

Yield: 83.58 g (342 mmol, 103%, the surplus probably being unremoved $SOCl_2$). The membrane pump was flushed free of residual $SOCl_2$ by direct suction of several liters of deionized water through the pump and into one of two small holes in the lid of a plastic bucket in a fume hood. The pump was then flushed with ethanol and dried.

Synthesis of Polyox WSR N-80 End-Functionalized with 2-BBCl-2

1.51 g Polyox WSR N-80 (7.55 µmol) was added to 165 mL benzene, heated to near the boiling point to effect dissolution, and cooled to room temperature again. 375 µL 2-BBCl-2 (>375 mg; MW=244.68 g/mol; >1.5 mmol, i.e. a large stoichiometric excess) was added at once during magnetic stirring. After an hour 3 mL 2 M $Na_2CO_3$ (6 mmol) was added in order to extract residual 2-benzoylbenzoyl chloride, 2-benzoylbenzoic acid and other acidic impurities. A major part of the Polyox precipitated out in spite of the presence of the superior solvent benzene, and the benzene phase became milky, so water was distilled off azeotropically at about 69° C. in order to precipitate salts and force modified Polyox back into solution. During this phase frothing occurred, which was excessive and uncontrollable in case of Polyox concentrations in benzene over 1 w/v-% but controllable at 1% and below. When all water was removed (after 25-30 mL distillate) the temperature at the top of the distillation head increased to 78-9° C. The resulting clear benzene solution was cooled, the salts were filtered off, and the solution was evaporated to near dryness. Yield: 1.7 g.

The UV-Vis spectrum of 5 g/L of the compound in benzene showed an absorbance of 0.6 at the global maximum at 322 nm. This corresponded to a theoretical absorbance of 51 at the global benzophenone maximum at about 252 nm, since the ratio between the extinction coefficients at 255 and 322 nm is 86 for benzophenone in ethanol (data not shown). However, unfortunately the 252 nm peak could not be observed in benzene, which has very strong absorption below 300 nm. Hence benzene was not an ideal solvent for the UV-Vis measurements but was chosen anyway because of its superior solvation of Polyox, PEG 35000 and Tecogel 2000. Instead the local maximum at 322 nm, which is also exhibited by benzophenone, was used to calculate the approximate concentration of benzophenone groups.

The absorbance of the Polyox 2-BBCl-2 ester corresponded to a benzophenone content of about 19% by weight of the polymer. This was very unrealistic and indicated that a contamination of some benzophenone derivative was present, but because of lack of time it was decided to treat the compound as if it had this concentration of photo-initiator anyway.

Interestingly, 2-benzoylbenzoic acid could not be used as a reference, because it had only a very small absorbance at 322 nm which, furthermore, did not obey Lambert-Beer's law at increasing concentrations; this possibly indicated a concentration dependent dimer formation including the acid hydroxyl group in the very non-polar benzene, since the effect was absent in the synthesized Polyox 2-benzoylbenzoate.

Synthesis of PEG 35000 End-Functionalized with 2-BBCl-2

35.0 g Polyglykol Hoechst 35000 Schuppen (batch E06389543) and 200 mL benzene were mixed in a 500 mL round-bottomed flask and heated until everything was dissolved. The rather viscous solution was cooled to room temperature, and 5 mL 2-BBCl-2 was added in small portions during vigorous stirring. After an hour the mixture was transferred to a beaker, rinsing the flask with a little benzene. The modified PEG 35000 was precipitated by addition of 100 mL pentane. The compound was filtered off, washed several times with pentane and dried. Yield: 35.3 g.

The UV-Vis spectrum of 2.55 g/L compound in benzene had an absorbance of 0.035 at 322 nm, corresponding to A=3 at 252 nm and a concentration of 2.2% benzophenone by weight of the polymer. This was unrealistic but because of lack of time it was decided to treat the compound as if it had this concentration of photo-initiator anyway, as also described above for WSR N-80 end-functionalized with 2-BBCl-2.

Synthesis of Tecogel 2000 End-Functionalized with 2-BBCl-2

10.0 g Tecogel 2000 was added to 400 mL hot benzene during vigorous stirring. The solution contained some cross-linked, insoluble material (as is sometimes the case), which was filtered off using a metal sieve with 212 µm hole size. 250 µL 2-BBCl-2 was added at once during stirring at room temperature. After an hour the solution was transferred to a beaker, and 200 mL hexane was added during vigorous magnetic stirring and stirring by hand, since the voluminous precipitate was so hard that it prevented proper mixture of benzene and hexane by magnetic stirring alone. The compound formed a hard cylinder on the Büchner funnel and was filtered off. The compound was dried at 80° C. for a day, during which time it formed a porous ball, probably because of the internal pressure from the evaporating solvents. Yield: 10.3 g. The material was extremely tough and had to be divided using a strong knife and a butcher's metal glove! The UV-Vis spectrum in benzene was very similar to the control, which had not been subjected to 2-BBCl-2, and showed no sign at 322 nm of any attached benzophenone groups.

Production of Samples for Solvent Casting and Compounding

Based on the UV-Vis data mentioned above, the following set of samples (labelled 17-26) were made so that the maximum absorbance at 252 nm should not exceed 0.6, which would mean good through cure:

500 W/inch Hg lamp at a speed of 40 m/min. They were swelled in 60° C. hot tap-water for at least 5 minutes. Then the stability of the coatings was subjectively evaluated by continuous finger rubbing under running water on the following scale. The following results were obtained:

| Solution | Score of UV cured preparation |
| --- | --- |
| 17 | 1 |
| 18 | 1 |
| 19 | 2 |
| 20 | 2 |
| 21 | 2 |
| 22 | 2 |
| 23 | 2 |
| 24 | 2 |
| 25 | 2 |
| 26 | 2 |

| | Percentage composition (w/w-%) | | | | | | | |
| --- | --- | --- | --- | --- | --- | --- | --- | --- |
| | Thermoplastic matrix polymer | | Hydrophilic polymers | | | | Photo-initiator Benzo-phenone | |
| Solution No.* | TG 2000 CD 53 RA 015 | TG-P (w. photo-initiator) | Polyox WSR N-80 | PO-P (w. photo-initiator) | PEG 35000 | PEG-P (w. photo-initiator) | | Type |
| 17 | 1 | 1 | 2.983 | 0.017 | 0 | 0 | 0 | A |
| 18 | 0 | 2 | 3 | 0 | 0 | 0 | 0 | B |
| 19 | 2 | 0 | 2.966 | 0.034 | 0 | 0 | 0 | C |
| 20 | 2 | 0 | 3 | 0 | 0 | 0 | 0.0065 | D |
| 21 | 2 | 0 | 3 | 0 | 0 | 0 | 0 | E |
| 22 | 1 | 1 | 0 | 0 | 2.855 | 0.1455 | 0 | A |
| 23 | 0 | 2 | 0 | 0 | 3 | 0 | 0 | B |
| 24 | 2 | 0 | 0 | 0 | 2.709 | 0.291 | 0 | C |
| 25 | 2 | 0 | 0 | 0 | 3 | 0 | 0.0065 | D |
| 26 | 2 | 0 | 0 | 0 | 3 | 0 | 0 | E |

A. Double positive: Half amount of photo-initiator on matrix polymer and half on hydrophilic polymer
B. Positive #1: Photo-initiator bound to thermoplastic matrix polymer
C. Positive #2: Photo-initiator bound to hydrophilic polymer
D. Positive #3: Unbound photo-initiator added
E. Negative: No photo-initiator added
*In each instance, 0.01 w/w-% of triethanolamine was added and 23.75 w/w-% water and 71.24 w/w-% of 2-propanol were used as the solvent system, the constituents thereby adding up to 100 w/w-%.

In some cases triethanolamine may act as an auxiliary electron donor for benzophenone and hence increase the cure speed. In order to ascertain whether it was necessary to add the amine here, sample 25 was compounded with and without 0.01% triethanolamine present, respectively, and UV cured at 10 or 40 m/min, respectively. At 10 m/min the coating was stable regardless of whether the amine was present or not, but at 40 m/min (with much less light) the coating without amine was completely unstable, whereas the coating with amine was stable. Hence triethanolamine was added to all samples.

Tecogel 2000 and TG-β (Tecogel 2000 modified with photo-initiator) were actually refluxed in the 3:1 2-propanol:water solvent (w:w) to form stock solutions, because of their otherwise very slow dissolution. All solutions contained 5% dry matter. 4 g of each solution was spread out across a circular sheet (area 20 cm$^2$) of the polyurethane substrate Estane 58212, which was glued to the bottom of a slightly conical aluminium container. The containers were then heated overnight at 60° C. in order to evaporate the solvent and leave a dry, homogeneous coating of about 100 μm thickness. The coatings were heated to about 65° C. (where they became transparent) and UV cured under a Fusion LH6

No clear conclusion could be drawn from the results obtained in this example although a tendency towards a preference for the variants with photo-initiator linked to one or both of the thermoplastic matrix polymer and the hydrophilic polymer was observed. It is envisaged that further optimisation of the relative ratios of the constituents and the loading of the photo-initiator will support this hypothesis.

Projected Synthesis 1: 2-Benzoylbenzoyloxylation of Polyox WSR N-80 tert-Butyl 2-benzoylperoxybenzoate may be synthesized as described by L. Thijs, S. N. Gupta, D. C. Neckers (1979): "Photochemistry of Perester Initiators", *J. Org. Chem.*, 44(23), 4123-8, or by adding 2-benzoylbenzoyl chloride slowly to tert-butyl hydroperoxide in pyridine solvent; adding diethyl ether (or toluene or ethyl acetate); acidifying to extract pyridine; washing the ether phase with aqueous carbonate or bicarbonate to remove residual SOCl$_2$, SO$_2$, HCl, 2-benzoylbenzoyl chloride and 2-benzoylbenzoic acid; drying the organic phase; and removing the solvent.

The resulting tert-butyl 2-benzoylperoxybenzoate may then be made to react with Polyox WSR N-80 in benzene and purified in the same manner as described for the synthesis of benzoyloxylated Polyox WSR N-80 in benzene.

To the knowledge of the inventors no literature describes this reaction being applied to a polyether like Polyox.

Projected Synthesis 2:

It has been described in the literature that when some small benzoyloxylated ethers (e.g. tetrahydrofuran, see G. Sosnovsky, S.-O. Lawesson (1964): "The Peroxyester Reaction", *Angew. Chem. Int. Edit.*, 3(4), 269-76; or dibutyl ether, see S.-O. Lawesson, C. Berglund (1961): "Studies on peroxy compounds. XVIII. The preparation of aldehydes and ketones from ethers", Arkiv för Kemi, 17(45), 465-73) are boiled with an excess of alcohol (e.g. Irgacure 2959), benzoic acid is eliminated to give an unsaturated ether which can then add the alcohol to give the acetal:

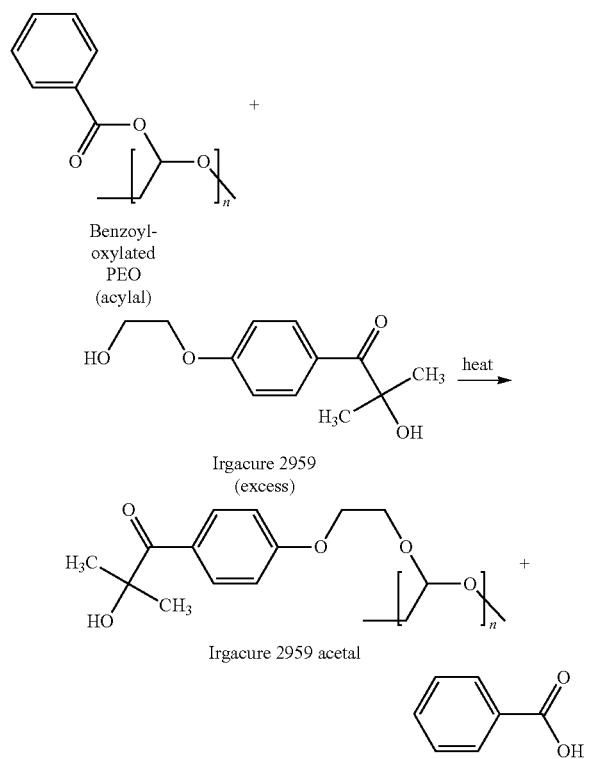

The reaction in this scheme may be performed in a range of inert solvents with high boiling points, e.g. ketones (such as MIBK or cyclohexanone), amides (such as DMF, DMAC, or NMP), DMSO, or the like.

Reference Example 1

| Ingredients | Compound A | Compound B | Compound C | Compound D |
|---|---|---|---|---|
| Tecogel 2000 | 75% | 50% | 75% | 50% |
| PVP K25 | 12.5% | 25% | | |
| PVP K90 | | | 12.5% | 25% |
| PEG 400 | 12.5% | 25% | 12.5% | 25% |

The ingredients were hot melt compounded in a Brabender compounder. PVP K25 and PVP K90 were from ISP Corp. In order to make the PVP processable and thermoplastic at 120° C. it was plasticized with PEG 400 prior to compounding. No photo-initiators were added. The blends were hot press laminated onto flat substrates of Tecogel 500. The adhesion and friction were evaluated after swelling in water for at least 24 hours on the scale defined in Example 1.

| | Adhesion after 24 hours | Friction after 24 hours |
|---|---|---|
| Compound A | 3 | High friction - Rough surface |
| Compound B | 1 | High friction - Very rough surface |
| Compound C | 3 | High friction - Rough surface |
| Compound D | 2 | High friction - Rough surface |

With 25% of 1:1 PVP:PEG 400 in 75% Tecogel 2000 it was possible to get good adhesion to Tecogel 500. If the content of 1:1 PVP:PEG400 was increased to 50%, delaminating and severe blistering was observed. The friction of all four blends had increased after 24 hours compared to the friction after 5 minutes.

Reference Example 2

| Ingredients | Compound E |
|---|---|
| Tecogel 2000 | 50.0% |
| PVP K25 | 33.3% |
| PEG 400 | 16.7% |

The ingredients were compounded together in a twin-screw extruder. PEG 400 was added to the extruder by a peristaltic pump, and Tecogel 2000 and PVP K25 were added by two gravimetric feeders. The blend was extruded into strands and pelletized.

Two single screw extruders were then connected to a single crosshead dual tube die. Extruder #1 was charged with a hydrophilic polyurethane, Tecophilic (Noveon), and extruder #2 was charged with Compound E. In this example, the materials were extruded onto a prefabricated tube of Estane 58212. Extruder #1 extruded Tecophilic as the inner layer, and extruder #2 extruded the outer layer. The ratios of inner to outer layer were varied by adjusting the output of either extruder by increasing or lowering the screw speed. The thickness of the layers was adjusted by varying either the output or the haul-off speed.

After extrusion the coated tube was swelled in water for at least 24 hours. It was observed (see FIGS. 4 (*a*) and (*b*)) that Compound E disintegrated when swelled, due to high water absorption and very low gel strength. The inner layer of Tecophilic had a tendency to bond poorly to the Estane 58212 tube. Delamination was observed on most of the tube.

Reference Example 3

| Ingredients (see FIG. 5 for compositions) |
|---|
| Tecogel 2000 |
| Tecogel 500 |
| Polyox N80 |

The ingredients were compounded together in a Brabender compounder in various ratios. The blends were hot press laminated onto flat substrates of Estane 58212. The adhesion was evaluated after swelling in water for at least 24 hours. The friction was evaluated after a dry-out period of 5 minutes.

The position of the symbols in FIG. 5 indicates the composition of the blends. ■-symbols represent blends that disintegrated when they were swelled in water: The water absorption was high but the gel strength was too low. The ●-symbols represent complete delamination, and separation of the layer from the substrate occurs. The ▼-symbols indicate good adhesion to the substrate with no or very few water blisters between the layers.

As illustrated in FIG. 5 high levels of the less hydrophilic Tecogel 500 gave good adhesion to the substrate, Area I, but the friction in this area was too high. Low frictions were observed on laminates with blends from Area II. However, these blends disintegrated or delaminated when they were swelled in water for 24 hours.

Hence, it was not possible to get a combination of low friction and good adhesion when laminating these blends on Estane 58212 without photo-initiator.

The invention claimed is:

1. A method for the preparation of a medical device element, the method comprising the steps of:
   (i) providing a prefabricated shaped article and/or a thermoplastic substrate polymer;
   (ii) providing a coating composition comprising a polymerized thermoplastic matrix polymer, a polymerized hydrophilic polymer and, optionally, a third polymerized polymer, and one or more photo-initiator(s), wherein the one or more photo-initiators are covalently linked to one of the polymerized thermoplastic matrix polymer, or the polymerized hydrophilic polymer, or the optional third polymerized polymer;
   (iii) extruding, injection molding or powder coating the coating composition of step (ii) on the prefabricated shaped article and/or the thermoplastic substrate polymer of step (i) so as to provide the medical device element of the prefabricated shaped article and/or the thermoplastic substrate polymer having thereon a layer of the coating composition, wherein, when both of the prefabricated shaped article and the thermoplastic substrate polymer are present, the prefabricated shaped article has thereon a layer of the thermoplastic substrate polymer; and
   (iv) irradiating the coating composition with UV or visible light, wherein the covalently linked photo-initiator(s) of the polymerized thermoplastic matrix polymer, or the polymerized hydrophilic polymer, or the optional third polymerized polymer generate free radicals to covalently cross-link one or more of the polymerized thermoplastic matrix polymer, or the polymerized hydrophilic polymer, or the optional third polymerized polymer of the coating composition via hydrogen or electron abstraction from one or more of the polymerized thermoplastic matrix polymer, or the polymerized hydrophilic polymer, or the optional third polymerized polymer, wherein the covalent cross-linking method does not require cross-linking by means of (meth)acrylate monomers and the coating composition does not comprise low-molecular weight residues of (meth)acrylic monomers.

2. The method according to claim 1, wherein the one or more photo-initiator(s) is at least two different photo-initiators.

3. The method according to claim 1, wherein said one or more photo-initiators are covalently linked to molecules of the polymerized thermoplastic matrix polymer and/or to molecules of the hydrophilic polymer.

4. The method according to claim 1, wherein the one or more photo-initiator moieties are covalently linked to a polymerized polymer selected from the group consisting of polyurethanes, polyethylene glycols, poly(lactic acid)s, collagen, nylons, vinyl polymers, and polysaccharides.

5. The method according to claim 1, wherein the polymerized thermoplastic matrix polymer is selected from the group consisting of polymerized hydrophilic polyurethane polymers and polymerized amphiphilic block-copolymers.

6. The method according to claim 1, wherein the polymerized hydrophilic polymer is a polymerized poly(ethylene oxide).

7. The method according to claim 1, wherein the polymerized thermoplastic substrate polymer is provided in step (i), and wherein step (iii) involves extruding or injection moulding the coating composition of step (ii) together with the polymerized thermoplastic substrate polymer of step (i) so as to provide the medical device element of said polymerized thermoplastic substrate polymer having thereon a layer of said coating composition.

8. The method according to claim 1, wherein the coating composition further includes the optional third polymerized polymer which is covalently linked to one or more photo-initiator(s).

* * * * *